(12) United States Patent
Kim et al.

(10) Patent No.: US 7,919,196 B2
(45) Date of Patent: Apr. 5, 2011

(54) EMITTING MATERIALS AND ORGANIC LIGHT EMITTING DEVICE USING THE SAME

(75) Inventors: Kong-Kyeom Kim, Daejeon Metropolitan (KR); Sung-Jin Yeo, Daejeon Metropolitan (KR); So-Yeon Choi, legal representative, Daejeon (KR); Hye-Young Jang, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 97 days.

(21) Appl. No.: 12/087,684

(22) PCT Filed: Jan. 12, 2007

(86) PCT No.: PCT/KR2007/000229
§ 371 (c)(1),
(2), (4) Date: Jul. 11, 2008

(87) PCT Pub. No.: WO2007/081179
PCT Pub. Date: Jul. 19, 2007

(65) Prior Publication Data
US 2009/0021149 A1    Jan. 22, 2009

(30) Foreign Application Priority Data

Jan. 13, 2006 (KR) .................. 10-2006-0003883

(51) Int. Cl.
*H01J 1/62* (2006.01)
(52) U.S. Cl. ............... 428/690; 313/504; 549/80
(58) Field of Classification Search ............ None
See application file for complete search history.

(56) References Cited

U.S. PATENT DOCUMENTS

| 6,165,383 A | 12/2000 | Chou |
| 6,534,199 B1 | 3/2003 | Hosokawa et al. |
| 2004/0067387 A1* | 4/2004 | Kim et al. ............. 428/690 |

FOREIGN PATENT DOCUMENTS

| JP | 2000-344691 | * 12/2000 |
| JP | 2004-067528 | 3/2004 |
| JP | 2004-224723 | 8/2004 |
| JP | 2005-008559 | 1/2005 |

* cited by examiner

*Primary Examiner* — D. Lawrence Tarazano
*Assistant Examiner* — Gregory Clark
(74) *Attorney, Agent, or Firm* — McKenna Long & Aldridge LLP

(57) ABSTRACT

The present invention provides a novel light emitting material and an organic light emitting device using the same.

22 Claims, 2 Drawing Sheets

Comparative compound 1

Compound 5

[Fig. 1]
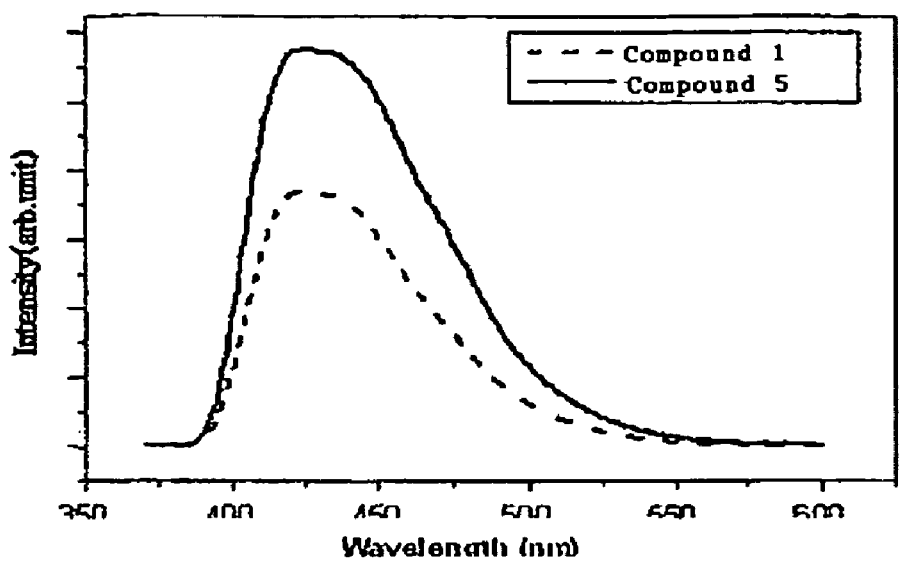
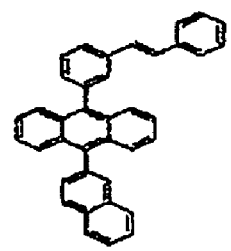
Comparative compound 1
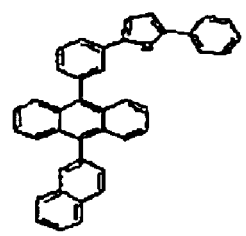
Compound 5
[Fig. 2]
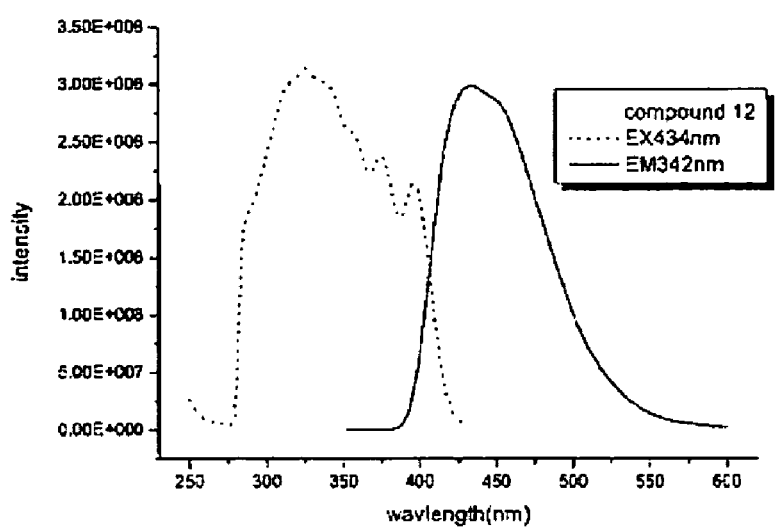

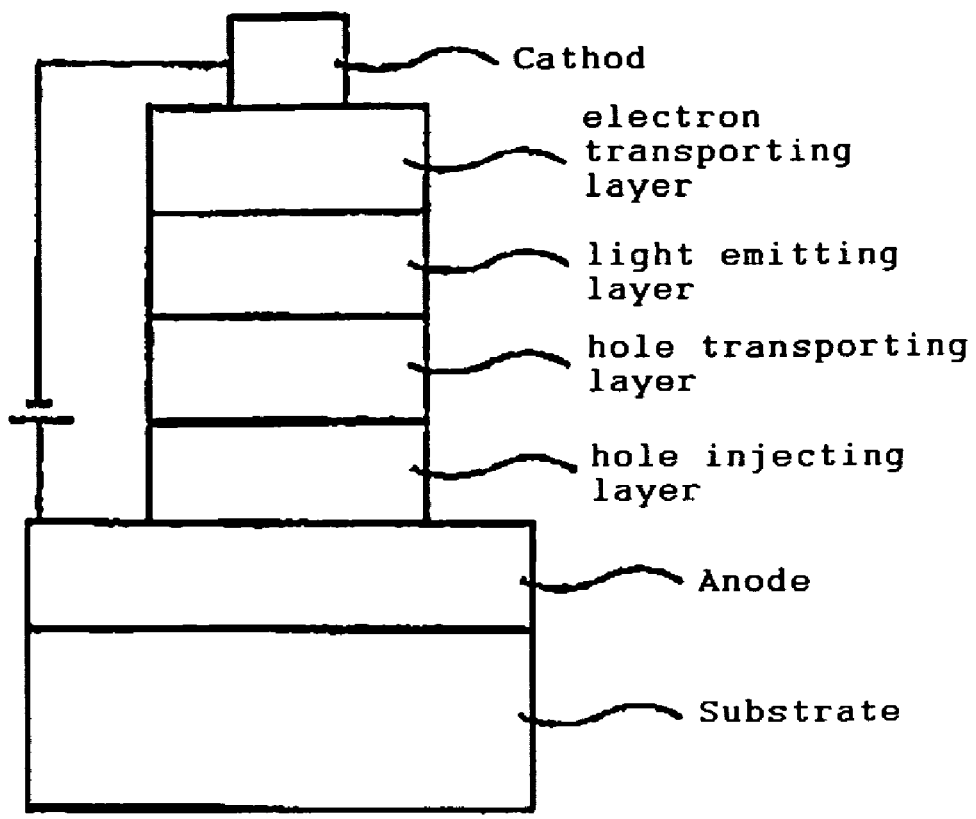
[Fig. 3]

EMITTING MATERIALS AND ORGANIC LIGHT EMITTING DEVICE USING THE SAME

TECHNICAL FIELD

The present invention relates to a novel structure of a light emitting material and to an organic light emitting device using the same.

This application claims the benefit of International Application Number PCT/KR/2007/000229 filed on Jan. 8, 2007 and Korean Application No. 10-2006-0003883 filed on Jan. 13, 2006, both of which are hereby incorporated by reference as if fully set forth herein.

BACKGROUND ART

In general, the term "organic light emitting phenomenon" refers to a phenomenon in which electric energy is converted to light energy by means of an organic material. The organic light emitting device using the organic light emitting phenomenon has a structure usually comprising an anode, a cathode, and an organic material layer interposed therebetween. Herein, the organic material layer may be mostly formed in a multilayer structure comprising the layers consisting of different materials, for example, a hole injecting layer, a hole transporting layer, a light emitting layer, an electron transporting layer, and an electron injecting layer, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, light is emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into light emitting materials and charge-transporting materials, for example, a hole injecting material, a hole transporting material, an electron transporting material and an electron injecting material, according to their functions. The light emitting materials can be classified into high molecular weight materials and low molecular weight materials, according to their molecular weights. The light emitting materials can be classified into fluorescent materials derived from the singlet excited state and phosphorescent materials derived from the triplet excited state. The light emitting materials can be divided into blue, green and red light emitting materials, and yellow and orange light emitting materials required for giving more natural colors, according to the colors of the emitted light.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host forming a light emitting layer is mixed in the light emitting layer, excitons which are generated in the light emitting layer are transported to the dopant, thus emitting a light with a high efficiency. Here, since the wavelength of the host is moved into the wavelength range of the dopant, a light having a desired wavelength can be obtained according to the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of stable and efficient materials. However, the development of stable and efficient organic material layer materials for the organic light emitting device has not yet been fully realized. Accordingly, the development of new materials is continuously desired.

DISCLOSURE OF INVENTION

Technical Problem

The present inventors have found a novel structure of a light emitting material, and then have found that the light emitting material efficiently serves as a light emitting material in an organic light emitting device.

Therefore, it is an object of the present invention to provide a novel structure of a light emitting material and an organic light emitting device using the same.

Technical Solution

The present invention provides a compound represented by the following formula 1:

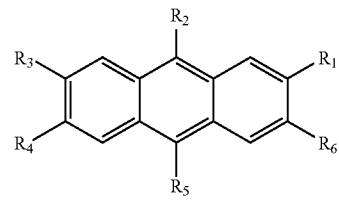

[Formula 1]

wherein $R_1$ to $R_6$ may be identical to or different from each other, and at least one thereof is represented by the following formula 2:

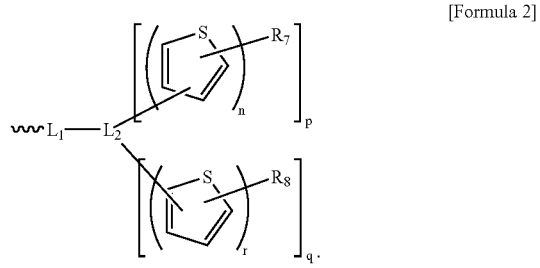

[Formula 2]

wherein n and p are each integers of 1 to 10, and q and r are each integers of 0 to 10, $L_1$ is a direct bond, or a substituted or unsubstituted $C_5$ to $C_{20}$ aryl group, or a substituted or unsubstituted $C_5$ to $C_{20}$ heterocyclic group, $L_2$ is a $C_5$ to $C_{20}$ aryl group, and $R_1$ to $R_6$, which are not represented by the formula 2, in the formula 1, and $R_7$ and $R_8$ in the formula 2 are each independently the identical or different substituents, and each selected from the group consisting of hydrogen; halogen; hydroxyl; mercapto; cyano; nitro; carbonyl; carboxyl; formyl; substituted or unsubstituted $C_1$-$C_{20}$ alkyl; substituted or unsubstituted $C_2$-$C_{10}$ alkenyl; substituted or unsubstituted $C_2$-$C_7$ alkynyl; substituted or unsubstituted $C_6$-$C_{32}$ aryl; substituted or unsubstituted heteroaryl; substituted or unsubstituted $C_3$-$C_7$ cycloalkyl in which a carbon atom in the ring may be substituted by an oxygen, nitrogen, or sulfur atom; $C_4$-$C_7$ cycloalkenyl in which a carbon atom in the ring may be substituted by an oxygen, nitrogen, or sulfur atom; substituted or unsubstituted $C_1$-$C_{20}$ alkoxy; substituted or unsubstituted $C_2$-$C_{10}$ alkenyloxy; substituted or unsubstituted $C_2$-$C_7$ alkynyloxy; substituted or unsubstituted aryloxy; substituted or unsubstituted $C_1$-$C_{20}$ alkylamine; substituted or unsubstituted $C_2$-$C_{10}$ alkenylamine; substituted or unsubstituted $C_2$-$C_7$ alkynylamine; substituted or unsubstituted arylamine; substituted or unsubstituted alkylarylamine; substituted or unsubstituted $C_1$-$C_{20}$ alkylsilyl; substituted or unsubstituted $C_2$-$C_{10}$ alkenylsilyl; substituted or unsubstituted $C_2$-$C_7$ alkynylsilyl; substituted or unsubstituted arylsilyl; substituted or unsubstituted alkylarylsilyl; substituted or unsubstituted $C_1$-$C_{20}$ alkylboranyl; substituted or unsubstituted $C_2$-$C_{10}$ alkenylboranyl; substituted or unsubstituted $C_2$-$C_7$ alkynylboranyl; substituted or unsubstituted arylboranyl; substituted or unsubstituted alkylarylboranyl; substituted or unsubstituted $C_1$-$C_{20}$ alkylthio; substituted or unsubstituted $C_2$-$C_{10}$ alkenylthio; substituted or unsubstituted $C_2$-$C_7$ alkynylthio; and substituted or unsubstituted arylthio groups.

Preferably, $R_1$ to $R_6$, which are not represented by the formula 2, in the formula 1, and $R_7$ and $R_8$ in the formula 2 are each independently the identical or different substituents, and each can be selected from the group consisting of hydrogen, cyano, nitro, substituted or unsubstituted $C_1$-$C_{20}$ alkyl, substituted or unsubstituted $C_2$-$C_{10}$ alkenyl, substituted or unsubstituted $C_3$-$C_7$ cycloalkyl, substituted or unsubstituted $C_4$-$C_7$ cycloalkenyl, substituted or unsubstituted $C_6$-$C_{32}$ aryl, substituted or unsubstituted heteroaryl, substituted or unsubstituted $C_1$-$C_{20}$ alkoxy, substituted or unsubstituted aryloxy, substituted or unsubstituted $C_1$-$C_{20}$ alkylamine, substituted or unsubstituted arylamine, substituted or unsubstituted alkylarylamine, substituted or unsubstituted $C_1$-$C_{20}$ alkylsilyl; substituted or unsubstituted $C_1$-$C_{20}$ alkylboranyl, substituted or unsubstituted arylboranyl, substituted or unsubstituted alkylarylboranyl, substituted or unsubstituted $C_1$-$C_{20}$ alkylthio, and substituted or unsubstituted arylthio groups.

$R_1$ to $R_6$, which are not represented by the formula 2, in the formula 1, and $R_7$ and $R_8$ in the formula 2 can be each independently mono- or poly-substituted with the identical or different substituents selected from the group consisting of:

halogen, hydroxyl, mercapto, cyano, nitro, amino, carbonyl, carboxyl, formyl, $C_1$-$C_{20}$ alkyl, $C_2$-$C_{10}$ alkenyl, $C_2$-$C_7$ alkynyl, aryl, heteroaryl, $C_3$-$C_7$ cycloalkyl, a saturated or unsaturated 3- to 7-membered heterocyclic ring, acryl, $C_1$-$C_{20}$ alkoxy, $C_2$-$C_{10}$ alkenyloxy, $C_2$-$C_7$ alkynyloxy, $C_1$-$C_{20}$ alkylamine, $C_2$-$C_{10}$ alkenylamine, $C_2$-$C_7$ alkynylamine, arylamine, alkylarylamine, $C_1$-$C_{20}$ alkylsilyl, $C_2$-$C_{10}$ alkenylsilyl, $C_2$-$C_7$ alkynylsilyl, alkoxysilyl, arylsilyl, alkylarylsilyl, $C_1$-$C_{20}$ alkylboranyl, $C_2$-$C_{10}$ alkenylboranyl, $C_2$-$C_7$ alkynylboranyl, arylboranyl, alkylarylboranyl, $C_1$-$C_{20}$ alkylthio, $C_2$-$C_{10}$ alkenylthio, $C_2$-$C_7$ alkynylthio, and arylthio groups.

Preferably, $R_1$ to $R_6$, which are not represented by the formula 2, in the formula 1, and $R_7$ and $R_8$ in the formula 2 may be each independently mono- or ploy-substituted with the identical or different substituents selected from the group consisting of:

cyano, nitro, formyl, methyl, ethyl, propyl, phenyl, naphthyl, biphenyl, anthracenyl, imidazolyl, thiazolyl, oxazolyl, thiophenyl, pyridyl, pyrimidyl, pyrrolyl, cyclobutenyl, cyclopentenyl, methoxy, ethoxy, propoxy, phenoxy, napththoxy, methylamine, ethylamine, propylamine, phenylamine, naphthylamine, methylphenylamine, ethylphenylamine, ethylnaphthylamine, dimethylboranyl, diethylboranyl, dipropylboranyl, diphenylboranyl, dinaphthylboranyl, phenylnaphthylboranyl, phenylmethylboranyl, naphthylmethylboranyl, naphthylethylboranyl, trimethylsilyl, triethylsilyl, tripropylsilyl, triphenylsilyl, trinaphthylsilyl, dimethylphenylsilyl, diethylphenylsilyl, diphenylmethylsilyl, methylthio, ethylthio, propylthio, butylthio, phenylthio and naphthylthio groups.

The substituted or unsubstituted $C_3$-$C_7$ cycloalkyl in which a carbon atom in the ring may be substituted by an oxygen, nitrogen, or sulfur atom, or the $C_4$-$C_7$ cycloalkenyl in which a carbon atom in the ring may be substituted by an oxygen, nitrogen, or sulfur atom, is a 5- or 6-membered substituted or unsubstituted, saturated or unsaturated ring.

$R_1$ to $R_6$, which are not represented by the formula 2, in the formula 1, and $R_7$ and $R_8$ in the formula 2 are each independently the identical or different substituent, and each can be selected from the group consisting of methyl, ethyl, propyl, butyl, isopropyl, n-butyl, t-butyl, isobutyl, n-pentyl, neo-pentyl, n-hexyl, ethenyl, propenyl, butenyl, pentenyl, hexenyl, 2-methyl-ethenyl, 2-methyl-propenyl, 2-methyl-butenyl, 2-methyl-pentenyl, 2-methyl-hexenyl, imidazolyl, thiazolyl, oxazolyl, thiophenyl, pyridyl, pyrimidyl, pyrrolyl, 2-methylimidazolyl, 2-methylthiazolyl, 2-methyloxazolyl, phenyl, naphthyl, anthracenyl, biphenyl, terphenyl, tetracenyl, 3-methyl-phenyl, 4-methyl-naphthyl, 9-methyl-anthracenyl, 4-methyl-tetracenyl, 2-methyl-imidazolyl, 2-methyl-oxazolyl, 2-methyl-thiazolyl, 2-methyl-furanyl, 2-methyl-thiophenyl, 2-methyl-pyrazolyl, 2-methyl-pyridyl, 2-methyl-pyrimidinyl, methoxy, ethoxy, propoxy, butoxy, pentoxy, hexoxy, isopropoxy, isobutoxy, t-butoxy, neo-pentoxy, phenoxy, napththoxy, biphenoxy, 3-methyl-phenoxy, 4-methyl-napththoxy, 2-methyl-biphenoxy, methylamine, ethylamine, propylamine, butylamine, pentylamine, hexylamine, heptylamine, isopropylamine, isobutylamine, t-butylamine, 2-pentylamine, neo-pentylamine, phenylamine, naphthylamine, biphenylamine, anthracenylamine, 3-methyl-phenylamine, 4-methyl-naphthylamine, 2-methyl-biphenylamine, 9-methyl-anthracenylamine, phenylmethylamine, phenylethylamine, naphthylmethylamine, naphthylethylamine, biphenylmethylamine, 3-methyl-phenyl methylamine, phenyl isopropylamine, naphthylisopropylamine, naphthylisobutylamine, biphenyl isopropylamine, trimethylsilyl, triethylsilyl, tributylsilyl, tri(isopropyl)silyl, tri(isobutyl)silyl, tri(t-butyl)silyl, tri(2-butyl)silyl, triphenylsilyl, tri-naphthylsilyl, tribiphenylsilyl, tri(3-methylphenyl)silyl, tri(4-methylnaphthyl)silyl, tri(2-methylbiphenyl)silyl, phenyl methylsilyl, phenyl ethylsilyl, naphthylmethylsilyl, naphthylethylsilyl, biphenyl methylsilyl, 3-methyl-phenyl methylsilyl, phenyl isopropylsilyl, naphthylisopropylsilyl, naphthylisobutylsilyl, biphenyl isopropylsilyl, dimethylboranyl, diethylboranyl, dipropylamine, dibutylamine, dipentylamine, diisopropylboranyl, diisobutylboranyl, di(t-butyl)boranyl, isopropylisobutylamine, diphenylboranyl, dinaphthylboranyl, dibiphenylboranyl, di(3-methylphenyl)boranyl, di(4-methylnaphthyl)boranyl, di(2-methylbiphenyl)boranyl, phenylmethylboranyl, phenylethylboranyl, naphthylmethylboranyl, naphthylethylboranyl, biphenyl-methylboranyl, 3-methyl-phenylmethylboranyl, phenylisopropylboranyl, methylthio, ethylthio, propylthio, butylthio, pentylthio, hexylthio, tri(isopropyl)thio, tri(isobutyl)thio, tri(t-butyl)thio, tri(2-butyl)thio, phenylthio, naphthylthio, biphenylthio, (3-methylphenyl)thio, (4-methylnaphthyl)thio and (2-methylbiphenyl)thio groups.

Preferably, $R_1$ to $R_6$, which are not represented by the formula 2, in the formula 1, and $R_7$ and $R_8$ in the formula 2 may be each independently the identical or different substituent, and each can be selected from the group consisting of methyl, ethyl, isopropyl, t-butyl, ethenyl, propenyl, 2-methylethenyl, 2-methyl-propenyl, imidazolyl, thiazolyl, oxazolyl, 2-methylimidazolyl, 2-methylthiazolyl, 2-methyloxazolyl, phenyl, naphthyl, biphenyl, terphenyl, anthracenyl, 3-methyl-phenyl, 4-methyl-naphthyl, methoxy, ethoxy, isopropoxy, isobutoxy, phenoxy, napthoxy, 3-methyl-phenoxy, 4-methyl-napththoxy, methylamine, ethylamine, isopropylamine, isobutylamine, t-butylamine, phenylamine, naphthylamine, 3-methyl-phenylamine, 4-methyl-naphthylamine, phenyl methylamine, phenyl ethylamine, naphthyl-methylamine, 3-methyl-phenyl methylamine, phenyl isopropylamine, trimethylsilyl, triethylsilyl, tri(isopropyl)silyl, tri(isobutyl)silyl, triphenyl silyl, trinaphthylsilyl, tri(3-methylphenyl)silyl, tri(4-methylnaphthyl)silyl, phenyl methylsilyl, phenyl ethylsilyl, 3-methyl-phenyl methylsilyl, phenyl isopropylsilyl, dimethylboranyl, diethylboranyl, diisopropylboranyl, diisobutylboranyl, diphenylboranyl, dinaphthylboranyl, di(3-methylphenyl)boranyl, di(4-methylnaphthyl)boranyl, phenyl-methylboranyl, phenylethylboranyl, 3-methyl-phenylmethylboranyl, phenylisopropylboranyl, methylthio, ethylthio, tri(isopropyl)thio, tri(isobutyl)thio, phenylthio, naphthylthio, (3-methylphenyl)thio and (4-methylnaphthyl)thio groups.

$R_1$ to $R_6$, which are not represented by the formula 2, in the formula 1, and $R_7$ and $R_8$ in the formula 2 may be each independently the identical or different substituent, and each can be selected from the group consisting of substituted or unsubstituted phenyl, substituted or unsubstituted naphthyl, substituted or unsubstituted biphenyl, substituted or unsubstituted terphenyl, and substituted or unsubstituted anthracenyl.

The substituted phenyl, naphthyl, biphenyl, terphenyl and anthracenyl can be substituted with at least one selected from the group consisting of cyano, nitro, formyl, substituted or unsubstituted $C_1$-$C_{20}$ alkyl, aryl, heteroaryl, $C_4$-$C_7$ cycloalkenyl, substituted or unsubstituted $C_1$-$C_{20}$ alkoxy, aryloxy, $C_1$-$C_{20}$ alkylamine, arylamine, alkylarylamine, $C_1$-$C_{20}$ silyl, arylsilyl, alkylarylsilyl, $C_1$-$C_{20}$ alkylboranyl, arylboranyl, alkylarylboranyl, $C_1$-$C_{20}$ alkylthio and arylthio groups.

Preferably, at least one of $R_1$ to $R_6$ is represented by the formula 2, and the remaining $R_1$ to $R_6$ can be selected from the group consisting of:

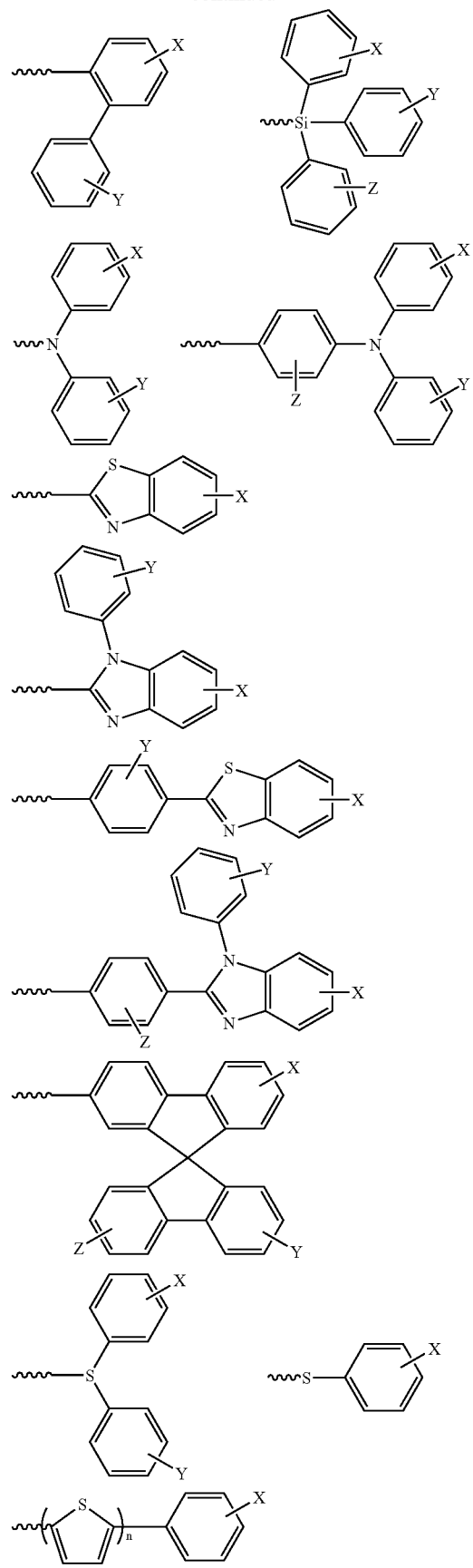

-continued

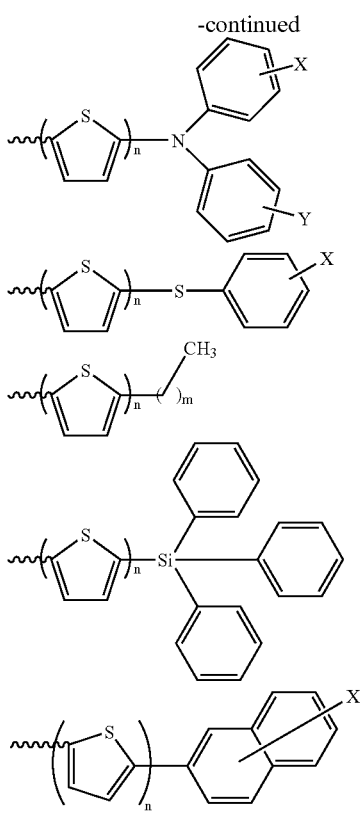

wherein X, Y and Z are each independently the identical or different substituents and each ring moiety to which X, Y or Z can be attached can be substituted with one or more of the identical or different substituents, such as X, Y and Z.

X, Y and Z are each independently selected from the group consisting of cyano, nitro, formyl, substituted or unsubstituted $C_1$-$C_{20}$ alkyl, aryl, heteroaryl, $C_4$-$C_7$ cycloalkenyl, substituted or unsubstituted $C_1$-$C_{20}$ alkoxy, aryloxy, $C_1$-$C_{20}$ alkylamine, arylamine, alkylarylamine, $C_1$-$C_{20}$ silyl, arylsilyl, alkylarylsilyl, $C_1$-$C_{20}$ alkylboranyl, arylboranyl, alkylarylboranyl; $C_1$-$C_{20}$ alkylthio and arylthio. It is preferable that X, Y and Z are each independently selected from the group consisting of cyano, nitro, methyl, ethyl, isopropyl, t-butyl, methoxy, ethoxy, propoxy, methylthio, imidazolyl, pyridyl, thiazolyl, oxazolyl, furanyl, thiophenyl, pyrrolyl, pyridyl and pyrimidyl.

In the formula 1, only one of $R_1$ to $R_6$ can be represented by the formula 2, or two of $R_1$ to $R_6$ can be represented by the formula 2. Three of $R_1$ to $R_6$ can be represented by the formula 2, and four of $R_1$ to $R_6$ can be represented by the formula 2. Five of $R_1$ to $R_6$ can be represented by the formula 2, and all of $R_1$ to $R_6$ can be represented by the formula 2.

According to one embodiment of the present invention, there is provided a compound, wherein at least one of R2 and R5 in the formula 1 is a group represented by the formula 2.

According to another embodiment of the present invention, there is provided a compound, wherein R2 and R5 in the formula 1 are the same substituents represented by the formula 2.

According to still another embodiment of the present invention, there is provided a compound, wherein R2 and R5 in the formula 1 are the different substituents represented by the formula 2, and one of R2 and R5 is a substituent represented by the formula 2 with L1 being a direct bond, phenyl, naphthyl or carbazole.

According to still another embodiment of the present invention, there is provided a compound, wherein at least one of R1, R3, R4 and R6 in the formula 1 is a group represented by the formula 2.

According to still another embodiment of the present invention, there is provided a compound, wherein in the formula 1, one of R1 and R6 and one of R3 and R4 are the same substituents represented by the formula 2.

According to still another embodiment of the present invention, there is provided a compound, wherein in the formula 1, one of R1 and R6 and one of R3 and R4 are the different substituents represented by the formula 2, and one among them is a substituent represented by the formula 2 with L1 being a direct bond, phenyl, naphthyl or carbazole.

Preferably, in the formula 2, $L_1$ is a direct bond, phenyl, naphthyl or carbazole, and $L_2$ is phenyl, naphthyl or anthracenyl.

The terms, as used in $R_1$ to $R_8$ of the formulae 1 and 2 according to the present invention are as follows.

The term, "$C_1$-$C_{20}$ alkyl" or "unsubstituted $C_1$-$C_{20}$ alkyl", whether as part of another term or not, refers to a linear or branch chained saturated hydrocarbon such as methyl, ethyl, n-propyl, n-butyl, n-pentyl, n-hexyl, n-decanyl, n-eicosanyl. The term, "substituted $C_1$-$C_{20}$ alkyl" is the $C_1$-$C_{20}$ alkyl which is mono- or poly-substituted with the identical or different substituent, such as halogen, hydroxyl, mercapto, cyano, nitro, amino, carbonyl, carboxyl, formyl, $C_1$-$C_{20}$ alkyl, $C_2$-$C_{10}$ alkenyl, $C_2$-$C_7$ alkynyl, aryl, heteroaryl, $C_3$-$C_7$ cycloalkyl, a saturated or unsaturated 3- to 7-membered heterocyclic ring, acryl, $C_1$-$C_{20}$ alkoxy, $C_2$-$C_{10}$ alkenyloxy, $C_2$-$C_7$ alkynyloxy, $C_1$-$C_{20}$ alkylamine, $C_2$-$C_{10}$ alkenylamine, $C_2$-$C_7$ alkynylamine, arylamine, alkylarylamine, $C_1$-$C_{20}$ alkylsilyl, $C_2$-$C_{10}$ alkenylsilyl, $C_2$-$C_7$ alkynylsilyl, arylsilyl, alkylarylsilyl, $C_1$-$C_{20}$ alkylboranyl, $C_2$-$C_{10}$ alkenylboranyl, $C_2$-$C_7$ alkynylboranyl, arylboranyl, alkylarylboranyl, $C_1$-$C_{20}$ alkylthio, $C_2$-$C_{10}$ alkenylthio, $C_2$-$C_7$ alkynylthio or arylthio (hereinafter, collectively referred to as "the listed substituent"). The term, "heterocyclic" refers to a ring structure in which at least one backbone carbon is replaced by an oxygen, nitrogen or sulfur atom.

The term, "$C_2$-$C_{10}$ alkenyl" or "unsubstituted $C_2$-$C_{10}$ alkenyl", whether as part of another term or not, refers to a linear or branch chained hydrocarbon radical having at least one double bond between the adjacent carbon atoms. Examples of the $C_2$-$C_{10}$ alkenyl group include vinyl, allyl, but-2-enyl, pent-2-enyl, hept-3-enyl, and dec-1,3-dien-yl. The term, "substituted $C_2$-$C_{10}$ alkenyl" refers to a $C_2$-$C_{10}$ alkenyl group, which is mono- or poly-substituted with one or more of the identical or different substituent selected from the above-listed substituents. Examples of the substituted $C_2$-$C_{10}$ alkenyl group include isoprop-2-enyl, isobutenyl, t-butenyl, and 2-methyl-2-decenyl.

The term, "$C_2$-$C_7$ alkynyl" or "unsubstituted $C_2$-$C_7$ alkynyl", whether as part of another term or not, refers to a linear or branch chained hydrocarbon radical having at least one triple bond between the adjacent carbon atoms. Examples of the $C_2$-$C_7$ alkynyl group include ethynyl, prop-1-ynyl, hex-2-ynyl, and hept-3-ynyl. The term, "substituted $C_2$-$C_7$ alkynyl" refers to a $C_2$-$C_7$ alkynyl group, which is mono- or poly-substituted with one or more of the identical or different substituent selected from the above-listed substituents. Examples of the substituted $C_2$-$C_7$ alkynyl group include 2-methylethynyl, 2-methylpropynyl, 2-methylbutynyl, and 3-methoxyheptynyl.

The term, "aryl" or "unsubstituted aryl", whether as part of another term or not, refers to a single or multiple, aromatic hydrocarbon rings. In the case of the multiple rings, two or more rings are fused or linked without an intervening aliphatic chain. For example, the aryl group refers to phenyl, biphenyl, terphenyl, naphthyl, anthracenyl, rubrenyl, and perylenyl. The term, "substituted aryl" refers to an aryl group, which is mono- or poly-substituted with one or more of the identical or different non-aryl substituents selected from the above-listed substituents. Examples of the substituted aryl groups are methylphenyl, methoxyphenyl, methylbiphenyl, methylterphenyl, methylnaphthyl, methoxynaphthyl, and methylanthracenyl.

The term, "heteroaryl" or "unsubstituted heteroaryl", whether as part of another term or not, refers to single or multiple, aromatic hydrocarbon rings, in which at least one backbone carbon atom is replaced by an oxygen, nitrogen or sulfur atom. In the cases of multiple rings, two or more rings are fused, including optionally benzo-fused, or linked without an intervening aliphatic chain. The term, "substituted heteroaryl" refers to a heteroaryl group, which is mono- or poly-substituted with one or more of the identical or different non-heteroaryl substituents selected from the above-listed substituents. For example, the substituted aryl groups are 2-methyl-oxazolyl, 2-methyl-imidazolyl, 2-methyl-thiazolyl, 3,4-dimethyl-thiophenyl, 2-methyl-furanyl, 2-methyl-pyridyl, 2-methyl-pyrimidyl, and 2-methyl-pyrrolyl.

The "$C_3$-$C_7$ cycloalkyl" or "unsubstituted $C_3$-$C_7$ cycloalkyl" refers to a saturated closed ring structure having 3 to 7 carbon atoms in the ring. One or more carbon atoms in the ring can be optionally replaced by an oxygen, nitrogen or sulfur atom, which is also referred to as "saturated heterocyclic ring". Examples of the $C_3$-$C_7$ cycloalkyl groups are cyclopropyl, cyclobutyl, cyclopentyl, cyclohexyl, and cycloheptyl. The term, "substituted $C_3$-$C_7$ cycloalkyl" refers to a $C_3$-$C_7$ cycloalkyl group having one or more substitution at the carbon or non-carbon ring member with one or more of the identical or different substituents selected from the above-listed substituents. Examples of the substituted $C_3$-$C_7$ cycloalkyl groups are methylcyclopropyl, methylcyclobutyl, methylcyclopentyl, methylcyclohexyl, and methylcycloheptyl.

The term, "$C_4$-$C_7$ cycloalkenyl" or "unsubstituted $C_4$-$C_7$ cycloalkenyl" refers to a ring structure having 4 to 7 carbon atoms with at least one double bond. One or more carbon atoms in the ring can be optionally replaced by an oxygen, nitrogen or sulfur atom, which is also referred to as an "unsaturated heterocyclic ring". For example, the $C_4$-$C_7$ cycloalkenyl groups refer to 3-cyclopentenyl, 4-cyclohexenyl, and 5-cycloheptenyl. The term, "substituted $C_4$-$C_7$ cycloalkenyl" refers to a $C_4$-$C_7$ cycloalkenyl group having one or more substitution at the carbon or non-carbon ring member with one or more of the identical or different substituents selected from the above-listed substituents. For example, the substituted $C_4$-$C_7$ cycloalkenyl groups refer to 3-methyl-3-cyclopentenyl, 2-methyl-4-cyclohexenyl, and 2-methyl-cycloheptenyl.

The term, "$C_1$-$C_{20}$ alkoxy" or "unsubstituted $C_1$-$C_{20}$ alkoxy" refers to an oxygen radical substituted with a $C_1$-$C_{20}$ alkyl group. Examples of the $C_1$-$C_{20}$ alkoxy groups are methoxy, ethoxy, n-propoxy, n-butoxy, n-decanoxy, n-dodecanoxy, and n-eicosanoxy. The term, "substituted $C_1$-$C_{20}$ alkoxy" refers to a $C_1$-$C_{20}$ alkoxy group, wherein alkyl part is mono- or poly-substituted with one or more of the identical or different substituents selected from the above-listed substituents. Examples of the substituted $C_1$-$C_{20}$ alkoxy groups are 1-methylethoxy, 1-methyl-n-propoxy, 1-methyl-n-butoxy, 5-methoxydecanoxy, 3-methyl-dodecanoxy, and 3-phenylicosanoxy.

The term, "$C_2$-$C_{10}$ alkenyloxy" or "unsubstituted $C_2$-$C_{10}$ alkenyloxy" refers to an oxygen radical substituted with a $C_2$-$C_{10}$ alkenyl group. For example, the $C_2$-$C_{10}$ alkenyloxy groups refer to ethenyloxy, prop-1-enyloxy, but-1-enyloxy, hept-3-enyloxy, dec-2-enyloxy and the like. The term, "substituted $C_2$-$C_{10}$ alkenyloxy" refers to a $C_2$-$C_{10}$ alkenyloxy group, wherein the alkenyl part is mono- or poly-substituted substituted with one or more of the identical or different substituents selected from the above-listed substituents. For example, the substituted $C_2$-$C_{10}$ alkenyloxy groups are 1-methylethenyloxy, 1-methyl-1-propenyloxy, 1-methyl-1-butenyloxy, 2-methyl-1-heptyloxy, and 2-methyl-1-decenyloxy.

The term, "$C_2$-$C_7$ alkynyloxy" or "unsubstituted $C_2$-$C_7$ alkynyloxy" refers to an oxygen radical substituted with a $C_2$-$C_7$ alkynyl group. Examples of the $C_2$-$C_7$ alkynyloxy groups are ethynyloxy, 1-propynyloxy, 1-butynyloxy, 1,3-hept-diynyloxy and the like. The term, "substituted $C_2$-$C_7$ alkynyloxy" refers to a $C_2$-$C_7$ alkynyloxy group, wherein the alkynyl part is mono- or poly-substituted with one or more of the identical or different substituents selected from the above-listed substituents. Examples of the substituted $C_2$-$C_7$ alkynyloxy groups are 2-methyl-ethynyloxy, 2-methyl-1-propynyloxy, 2-methyl-1-butynyloxy, and 3-methoxy-1-heptynyloxy.

The term, "aryloxy" or "unsubstituted aryloxy" refers to the groups having an oxygen radical substituted with an aryl group. For example, the aryloxy groups are phenyloxy, naphthyloxy, anthracenyloxy, biphenyloxy, rubrenyloxy, perylenyloxy and the like. The term, "substituted aryloxy" refers to an aryloxy group, wherein the aryl part is mono- or poly-substituted with one or more of the identical or different substituents selected from the above-listed substituents. For example, the substituted aryloxy groups refer to 2-methyl-phenyloxy, 4-methyl-naphthyl-2-oxy, 9-methyl-anthracenyl-1-oxy, 2-methyl-biphenyloxy, 2-methyl-rubrenyloxy, 2-methyl-perylenyloxy.

The term, "$C_1$-$C_{20}$ alkylamine" or "unsubstituted $C_1$-$C_{20}$ alkylamine" refers to a nitrogen radical substituted with one or two identical or different $C_1$-$C_{20}$ alkyl groups. For example, the $C_1$-$C_{20}$ alkylamine groups include methylamine, ethylamine, propylamine, butylamine, pentylamine, heptylamine, heptadecanylamine and eicosanylamine. The term, "substituted $C_1$-$C_{20}$ alkylamine" refers to a $C_1$-$C_{20}$ alkylamine group, wherein the alkyl part is mono- or poly-substituted with one or more of the identical or different substituents selected from the above-listed substituents. For example, the substituted $C_1$-$C_{20}$ alkylamine groups include isopropylamine, N-propyl-N-(2-methoxy)butylamine, 2-methylbutylamine, N-butyl-N-(2-methyl)heptylamine and N-2-butyl-N-(2-methyl)heptadecanylamine.

The term, "$C_2$-$C_{10}$ alkenylamine" or "unsubstituted $C_2$-$C_{10}$ alkenylamine" refers to a nitrogen radical substituted with one or two identical or different $C_2$-$C_{10}$ alkenyl groups, in which a $C_1$-$C_{20}$ alkyl can also be attached to the nitrogen atom in case that only one $C_2$-$C_{10}$ alkenyl group is attached to the nitrogen atom. Examples of the $C_2$-$C_{10}$ alkenylamine groups are ethenylamine, 1-propenylamine, 1-butenylamine, 1-heptenylamine, and 1-decenylamine. The term, "substituted $C_2$-$C_{10}$ alkenylamine" refers to a $C_2$-$C_{10}$ alkenylamine group, wherein the alkenyl or alkyl part is mono- or poly-substituted with one or more of the identical or different substituents selected from the above-listed substituents. Examples of the substituted $C_2$-$C_{10}$ alkenylamine groups are 1-methyl-ethenylamine, 1-methyl-1-propenylamine 1-methyl-1-butenylamine, 1-methyl-1-heptenylamine, and 2-methyl-1-decenylamine.

The term, "$C_2$-$C_7$ alkynylamine" or "unsubstituted $C_2$-$C_7$ alkynylamine" refers to a nitrogen radical substituted with one or two identical or different $C_2$-$C_7$ alkynyl groups, in which a $C_1$-$C_{20}$ alkyl or $C_2$-$C_{10}$ alkenyl can also be attached to the nitrogen atom in case only one $C_2$-$C_{10}$ alkenyl group is attached to the nitrogen atom. Examples of the $C_2$-$C_{10}$ alkynylamine groups are ethynylamine, 1-propynylamine, 1-butynylamine, 2-heptynylamine, 1-decynylamine and the like. The term, "substituted $C_2$-$C_7$ alkynylamine" refers to a $C_2$-$C_7$ alkynylamine group, wherein one or more of the alkyl, alkenyl and alkynyl parts are mono- or poly-substituted with one or more of the identical or different substituents selected from the above-listed substituents. Examples of substituted $C_2$-$C_7$ alkynylamine groups are isopropynylamine, 2-methyl-1-butynylamine, 3-methyl-2-hepynylamine, and 2-methyl-1-decynylamine.

The term, "arylamine" or "unsubstituted arylamine" refers to a nitrogen radical substituted with one or two identical or different aryl or heteroaryl groups. Examples of the arylamine groups are phenylamine, 1-naphthylamine, 9-anthracenylamine, biphenylamine, rubrenylamine, and perylenylamine. The term, "substituted arylamine" refers to an arylamine group, wherein the ring part is mono- or poly-substituted with one or more of the identical or different substituents selected from the above-listed substituents. Examples of the substituted arylamine groups are 3-methylphenylamine, and 9-methoxyanthracenylamine.

The term, "alkylarylamine", "arylalkylamine", "unsubstituted arylalkylamine" or "unsubstituted alkylarylamine" refers to a nitrogen radical substituted with both an aryl or heteroaryl group and one of the $C_1$-$C_{20}$ alkyl, $C_2$-$C_{10}$ alkenyl, $C_2$-$C_7$ alkynyl, $C_1$-$C_{20}$ alkoxy, $C_2$-$C_{10}$ alkenyloxy, $C_2$-$C_7$ alkynyloxy groups. Examples of the alkylarylamine groups are N-methyl-N-phenylamine, N-ethyl-N-phenylamine, N-ethyl-N-(1-naphthyl)amine, N-methyl-N-(9-anthracenyl)amine, N-ethenyl-N-phenylamine, N-ethenyl-N-(1-naphthyl)amine, N-ethynyl-N-phenylamine, and N-ethynyl-N-(1-naphthyl)amine. The term, "substituted alkylarylamine" or "substituted arylalkylamine" refers to an alkylarylamine group, wherein the ring part, non-ring part or both parts are mono- or poly-substituted with one or more of the identical or different substituents selected from the above-listed substituents. Examples of the substituted alkylarylamine groups are N-isopropyl-N-phenylamine, and N-phenyl-N-(4-propyl-1-naphthyl)amine.

The term, "$C_1$-$C_{20}$ alkylsilyl" or "unsubstituted $C_1$-$C_{20}$ alkylsilyl" refers to a silicon radical substituted with one or more identical or different $C_1$-$C_{20}$ alkyl groups. For example, the alkylsilyl groups include trimethylsilyl, triethylsilyl, tripropylsilyl, tridecanylsilyl and trieicosanylsilyl. The term, "substituted $C_1$-$C_{20}$ alkylsilyl" refers to a $C_1$-$C_{20}$ alkylsilyl group, wherein one or more of the $C_1$-$C_{20}$ alkyl parts are mono- or poly-substituted with one or more of the same or different substituents selected from the above-listed substituents. For example, the substituted alkylsilyl groups include diisopropylmethylsilyl, di(isobutyl)methylsilyl, di(decanyl)isopropylsilyl and di(eicosanyl)methylsilyl.

The term, "$C_2$-$C_{10}$ alkenylsilyl" or "unsubstituted $C_2$-$C_{10}$ alkenylsilyl" refers to a silicon radical substituted with one or more identical or different $C_2$-$C_{10}$ alkenyl groups, in which one or more $C_1$-$C_{20}$ alkyl groups can also be attached to the silicon. For example, the alkenylsilyl groups include triethenylsilyl, tripropenylsilyl, tributenylsilyl, triheptenylsilyl and tridecenylsilyl. The term, "substituted $C_1$-$C_{20}$ alkenylsilyl" refers to a $C_2$-$C_{10}$ alkenylsilyl group, wherein the alkyl or alkenyl part is mono- or poly-substituted with one or more of the identical or different substituents selected from the above-listed substituents. For example, the substituted $C_2$-$C_{10}$ alkenylsilyl groups include tri(2-methylethenyl)silyl, tri(2-methylpropenyl)silyl, tri(2-methylheptenyl)silyl and tri(2-methyldecenyl)silyl.

The term, "$C_2$-$C_7$ alkynylsilyl" or "unsubstituted $C_2$-$C_7$ alkynylsilyl" refers to a silicon radical substituted with one or more identical or different $C_2$-$C_{10}$ alkynyl groups, in which one or more of the $C_1$-$C_{20}$ alkyl and $C_2$-$C_{10}$ alkenyl groups can also be attached to the silicon. For example, the alkynylsilyl groups include triethynylsilyl, tripropynylsilyl, tributynylsilyl, triheptenylsilyl and tridecenylsilyl. The term, "substituted $C_2$-$C_7$ alkynylsilyl" refers to a $C_2$-$C_7$ alkynylsilyl group, wherein the alkyl, alkenyl or alkynyl part is mono- or poly-substituted with one or more of the identical or different substituents selected from the above-listed substituents. The substituted $C_2$-$C_7$ alkynylsilyl groups include, for example, tri(2-methylethynyl)silyl, tri(2-methylpropynyl)silyl, tri(2-methylbutynyl)silyl, tri(2-methylheptynypsilyl and tri(2-methyldecenyl)silyl.

The term, "arylsilyl" or "unsubstituted arylsilyl" refers to a silicon radical substituted with one or more identical or different aryl or heteroaryl groups. For example, the arylsilyl groups include triphenylsilyl, trinaphthylsilyl and tribiphenylsilyl. The term, "substituted arylsilyl" refers to an arylsilyl group, wherein the aryl part is mono- or poly-substituted with one or more of the identical or different substituents selected from the above-listed substituents. For example, the substituted arylsilyl groups include tri(2-methylphenyl)silyl, tri(4-methylnaphthyl)silyl and tri(2-methylbiphenyl)silyl.

The term, "alkylarylsilyl", "arylalkylsilyl", "unsubstituted arylalkylsilyl" or "unsubstituted alkylarylsilyl" refers to a silicon radical substituted with one or more identical or different aryl or heteroaryl groups and at the same time one of the $C_1$-$C_{20}$ alkyl, $C_2$-$C_{10}$ alkenyl, $C_2$-$C_7$ alkynyl, $C_1$-$C_{20}$ alkoxy, alkenyloxy and $C_2$-$C_7$ alkynyloxy groups. Examples of the alkylarylsilyl groups are diphenylmethylsilyl, di-naphthylmethylsilyl, diphenylethylsilyl, dinaphthylethenylsilyl, dianthracenylethynylsilyl and the like. The term, "substituted alkylarylsilyl" refers to an alkylarylsilyl group, wherein the ring part, non-ring part or both parts are mono- or poly-substituted with one or more of the identical or different substituents selected from the above-listed substituents. Examples of the substituted alkylarylsilyl groups are di(2-methylphenyl)methylsilyl, and di(4-methylnaphthyl)methylsilyl.

The term, "$C_1$-$C_{20}$ alkylboranyl" or "unsubstituted $C_1$-$C_{20}$ alkylboranyl" refers to a boron radical substituted with one or more identical or different $C_1$-$C_{20}$ alkyl groups. For example, the alkylboranyl groups include dimethylboranyl, diethylboranyl, dipropylboranyl, diheptylboranyl, didecanylboranyl and di(eicosanyl)boranyl. The term, "substituted $C_1$-$C_{20}$ alkylboranyl" refers to a $C_1$-$C_{20}$ alkylboranyl group, wherein one or more of the $C_1$-$C_{20}$ alkyl parts are mono- or poly-substituted with one or more of the identical or different substituents selected from the above-listed substituents. For example, the substituted alkylboranyl groups include di(isopropyl)boranyl, di(isobutyl)boranyl, di(2-methylheptynyl)boranyl, di(2-methyldecanyl)boranyl, and di(2-methyl-eicosanyl)boranyl.

The term, "$C_2$-$C_{10}$ alkenylboranyl" or "unsubstituted $C_2$-$C_{10}$ alkenylboranyl" refers to a boron radical substituted with one or more identical or different $C_2$-$C_{10}$ alkenyl groups, in which a $C_1$-$C_{20}$ alkyl groups can also be attached to the boron atom in case only one $C_2$-$C_{10}$ alkenyl group is attached to the boron. For example, the alkenylboranyl groups include diethenylboranyl, dipropenylboranyl, dibutenylboranyl, diheptenylboranyl and didecanylboranyl. The term, "substituted $C_2$-$C_{10}$ alkenylboranyl" refers to a $C_2$-$C_{10}$ alkenylboranyl group, wherein the alkyl or alkenyl part is mono- or poly-substituted with one or more of the identical or different substituents selected from the above-listed substituents. Examples of the substituted alkenylboranyl groups are di(1-methylethenyl)boranyl and di(1-methylprop-1-enyl)boranyl, di(2-methlheptenyl)boranyl, and di(2-methyldecanyl)boranyl.

The term, "$C_2$-$C_7$ alkynylboranyl" or "unsubstituted $C_2$-$C_7$ alkynylboranyl" refers to a boron radical substituted with one or more identical or different $C_2$-$C_7$ alkynyl groups, in which a $C_1$-$C_{20}$ alkyl or $C_2$-$C_{10}$ alkenyl group can also be attached to the boron atom in case only one $C_2$-$C_7$ alkynyl group is attached to the boron. For example, the alkynylboranyl groups include diethynylboranyl, dipropynylboranyl, dibutynylboranyl, dihexynylboranyl and diheptylboranyl. The term, "substituted $C_2$-$C_7$ alkynylboranyl" refers to a $C_2$-$C_7$ alkynylboranyl group, wherein the alkyl, alkenyl or alkynyl part is mono- or poly-substituted with one or more of the identical or different substituents selected from the above-listed substituents. The substituted $C_2$-$C_7$ alkynylboranyl groups include, for example, di(2-methylethynyl)boranyl, di(2-methylpropynyl)boranyl, di(2-methylbutynyl)boranyl, di(2-methylhexynyl)boranyl and di(2-methylheptyl)boranyl.

The term, "arylboranyl" or "unsubstituted arylboranyl" refers to a boron radical substituted with one or more identical or different aryl or heteroaryl groups. Examples of the arylboranyl groups are diphenylboranyl, naphthylboranyl, dinaphthylboranyl, dibiphenylboranyl, rubrenylboranyl, and perylenylboranyl. The term, "substituted arylboranyl" refers to an arylboranyl group, wherein the aryl part is mono- or poly-substituted with one or more of the identical or different substituents selected from the above-listed substituents. Examples of the substituted arylboranyl groups are di(3-methylphenyl)boranyl, di(4-methylnaphth-1-yl)boranyl, and di(2-methylbiphenyl)boranyl.

The term, "alkylarylboranyl", "arylalkylboranyl", "unsubstituted arylalkylboranyl" or "unsubstituted alkylarylboranyl" refers to a boron radical substituted with an aryl or heteroaryl group and at the same time one of the $C_1$-$C_{20}$ alkyl, $C_2$-$C_{10}$ alkenyl, $C_2$-$C_7$ alkynyl, $C_1$-$C_{10}$ alkoxy, $C_2$-$C_{10}$ alkenyloxy and $C_2$-$C_7$ alkynyloxy groups. Examples of the alkylarylboranyl groups are ethylphenylboranyl, methylnaphthylboranyl, methylbiphenylboranyl, ethenylnaphthylboranyl, and ethynylphenylboranyl. The term, "substituted alkylarylboranyl" refers to an alkylarylboranyl group, wherein the ring part, non-ring part or both parts are mono- or poly-substituted with one or more of the identical or different substituents selected from the above-listed substituents. Examples of the substituted alkylarylboranyl groups are methyl(4-methylnaphthyl)boranyl, ethyl(2-methylphenyl)boranyl, and methyl(2-methylbiphenyl)boranyl.

The term, "$C_1$-$C_{20}$ alkylthio" or "unsubstituted $C_1$-$C_{20}$ alkylthio" refers to a sulfur radical substituted with a $C_1$-$C_{20}$ alkyl group. For example, the alkylthio groups include methylthio, ethylthio, n-propylthio, n-butylthio, n-heptylthio, n-decanylthio and n-eicosanylthio. The term, "substituted $C_1$-$C_{20}$ alkylthio" refers to a $C_1$-$C_{20}$ alkylthio group, wherein one or more of the $C_1$-$C_{20}$ alkyl parts are mono- or poly-substituted with one or more of the identical or different substituents selected from the above-listed substituents. For example, the substituted alkylthio groups include isopropylthio, isobutylthio, neo-pentylthio, 2-methylheptylthio, 2-methyldecanylthio and 2-methyleicosanylthio.

The term, "$C_2$-$C_{10}$ alkenylthio" or "unsubstituted $C_2$-$C_{10}$ alkenylthio" refers to groups having a sulfur radical substituted with a $C_2$-$C_{10}$ alkenyl group. For example, the alkenylthio groups include ethenylthio, propenylthio, butenylthio and decenylthio. The term, "substituted $C_2$-$C_{10}$ alkenylthio" refers to a $C_2$-$C_{10}$ alkenylthio group, wherein the alkenyl part is mono- or poly-substituted with one or more of the identical or different substituents selected from the above-listed substituents. For example, the substituted alkylthio groups include 1-methylethenylthio, 1-methyl-2-propenylthio, and 1-methyl-2-butenylthio.

The term, "$C_2$-$C_7$ alkynylthio" or "unsubstituted $C_2$-$C_7$ alkynylthio" refers to groups having a sulfur radical substituted with a $C_2$-$C_7$ alkynyl group. For example, the alkynylthio groups include ethynylthio, propynylthio, butynylthio and heptynylthio. The term, "substituted $C_2$-$C_7$ alkynylthio" refers to a $C_2$-$C_7$ alkynylthio group, wherein the alkynyl part is mono- or poly-substituted with one or more of the identical or different substituents selected from the above-listed substituents. The substituted $C_2$-$C_7$ alkynylthio groups include, for example, 2-methyl-ethynylthio, 2-methylpropynyl, 2-methylbutynylthio and 2-methylheptynylthio.

The term, "arylthio" or "unsubstituted arylthio" refers to groups having a sulfur atom substituted with an aryl groups. For example, the arylthio group includes phenylthio, naphthylthio, anthracenylthio and biphenylthio. The term, "substituted arylthio" refers to an arylthio group, wherein the aryl part is mono- or poly-substituted with one or more of the identical or different substituents selected from the above-listed substituents. For example, the substituted arylthio groups include 3-methylphenylthio, 4-methylnaphthylthio and 2-methylbiphenylthio.

Specific examples of the compound of the formula 1 are shown in the following Table 1, but are not limited thereto.

TABLE 1

| Compound | Structural Formula |
|---|---|
| 1 | |
| 2 | |
| 3 | |

TABLE 1-continued
| Compound | Structural Formula |
|---|---|
| 4 | 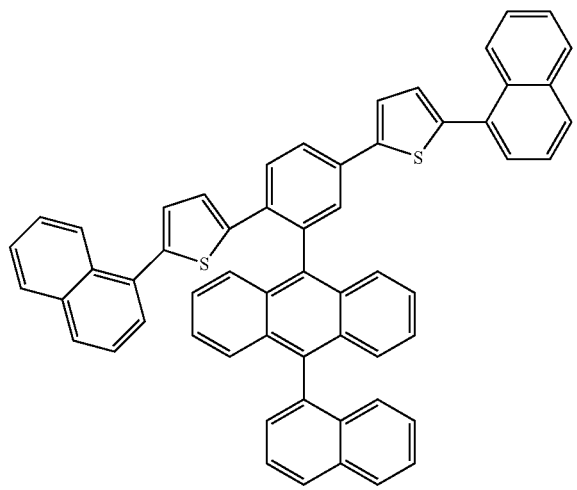 |
| 5 | 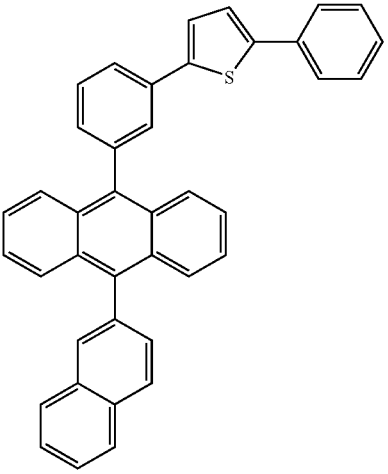 |
| 6 | 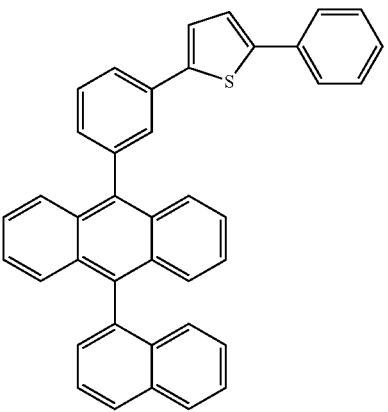 |

TABLE 1-continued
| Compound | Structural Formula |
|---|---|
| 7 | 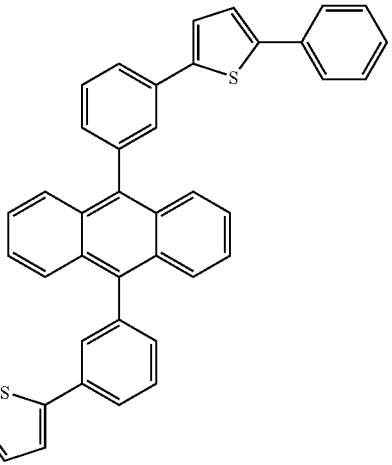 |
| 8 | 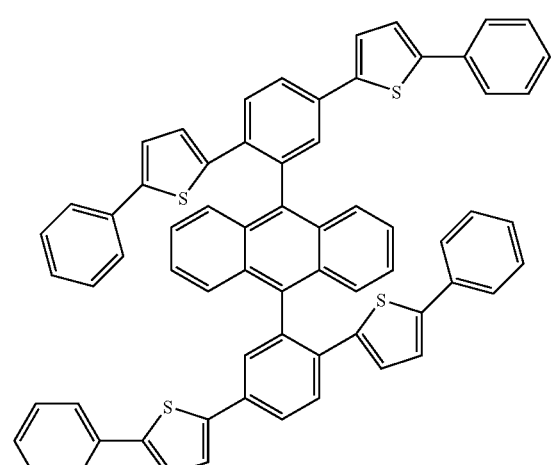 |
| 9 | 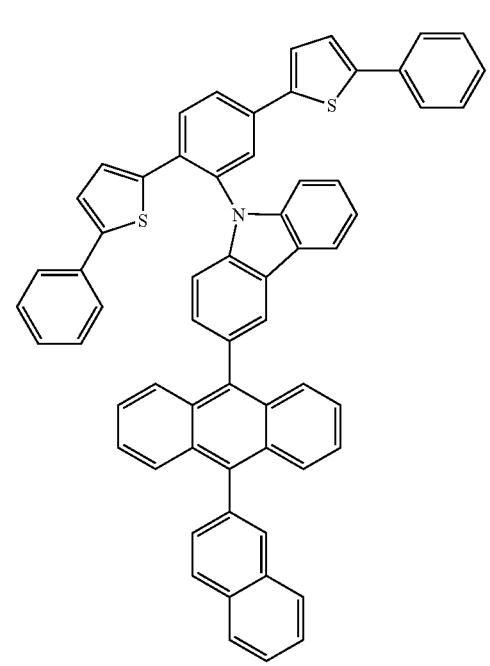 |

TABLE 1-continued
| Compound | Structural Formula |
| --- | --- |
| 10 | 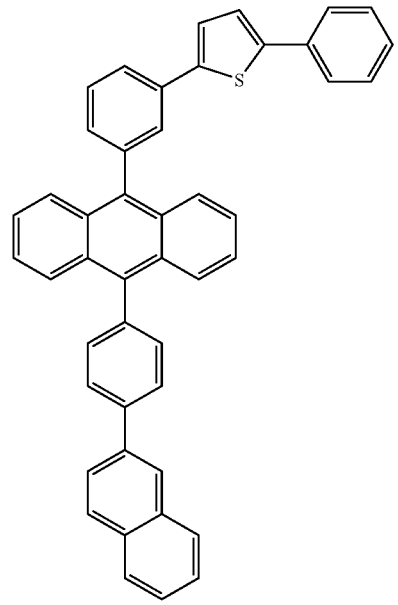 |
| 11 | 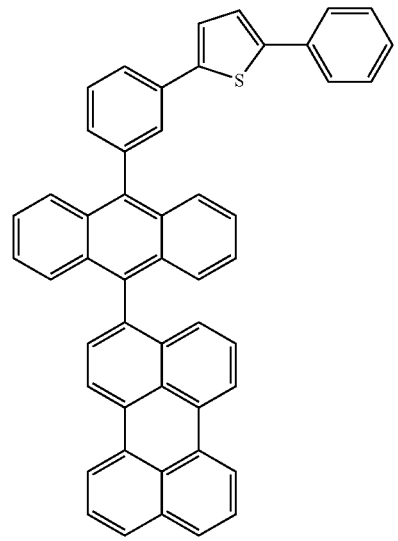 |

TABLE 1-continued
| Compound | Structural Formula |
|---|---|
| 12 | 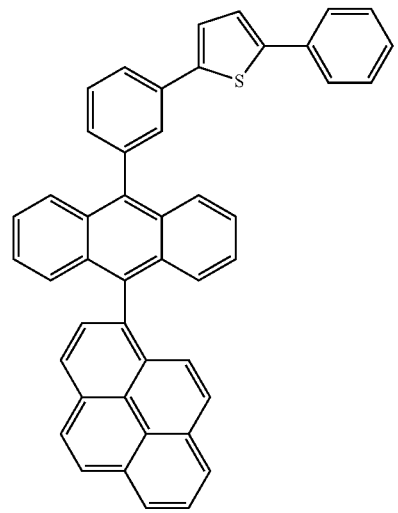 |
| 13 | 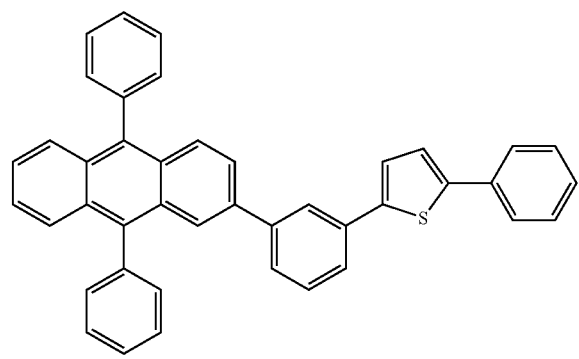 |
| 14 | 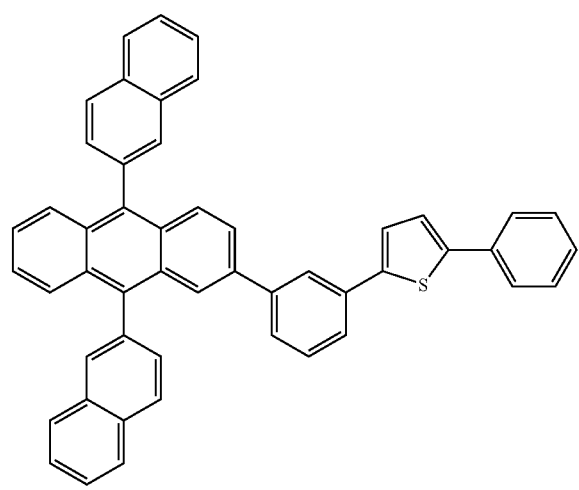 |

TABLE 1-continued
| Compound | Structural Formula |
| --- | --- |
| 15 | 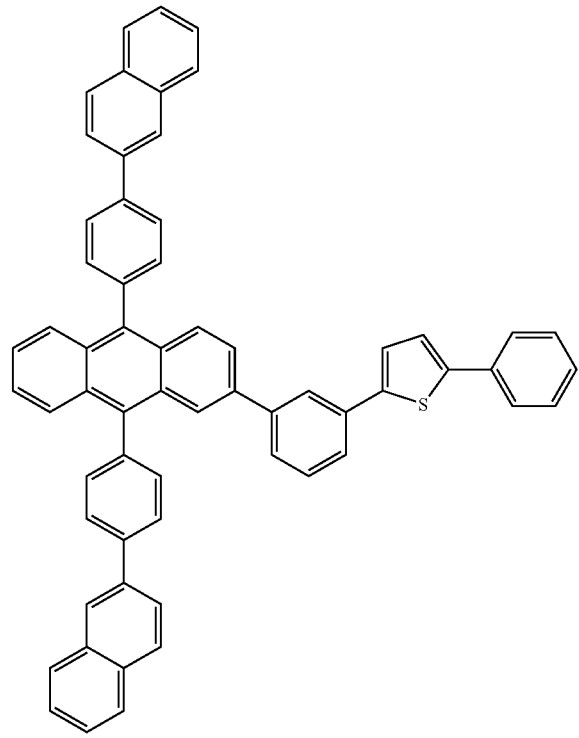 |
| 16 | 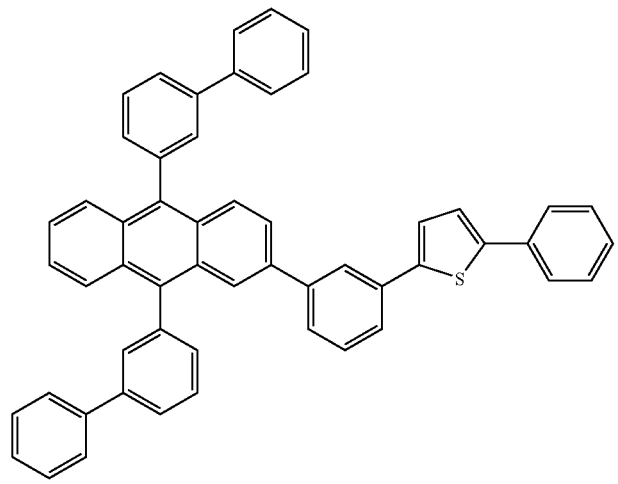 |

TABLE 1-continued
| Compound | Structural Formula |
| --- | --- |
| 17 | 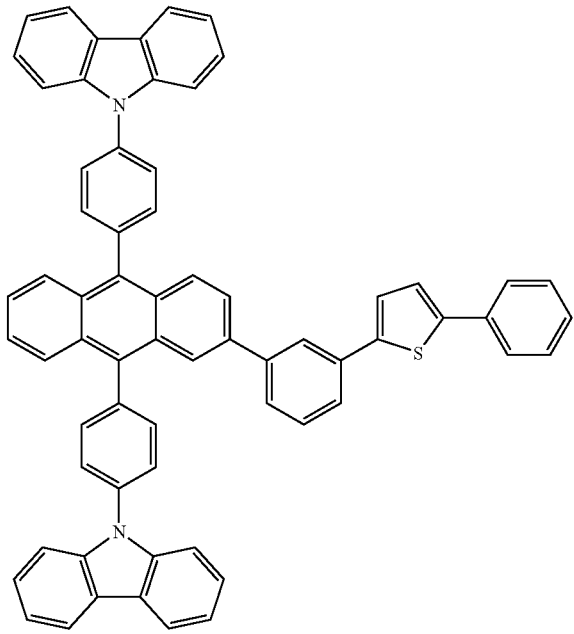 |
| 18 | 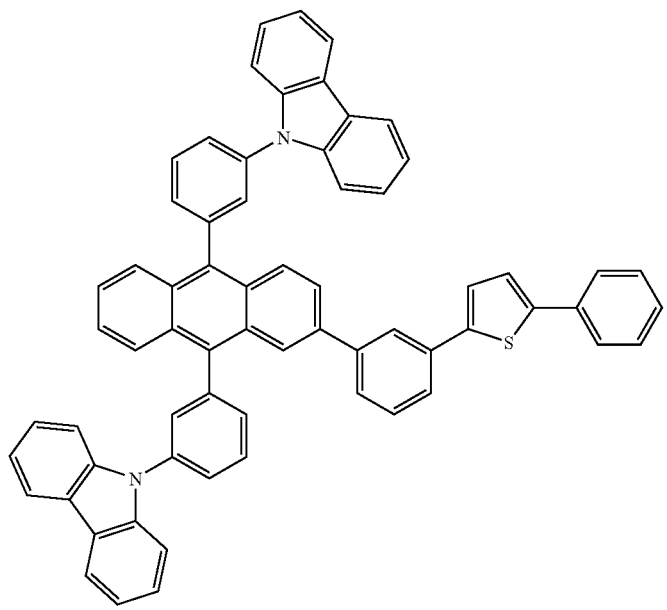 |

TABLE 1-continued
| Compound | Structural Formula |
|---|---|
| 19 | 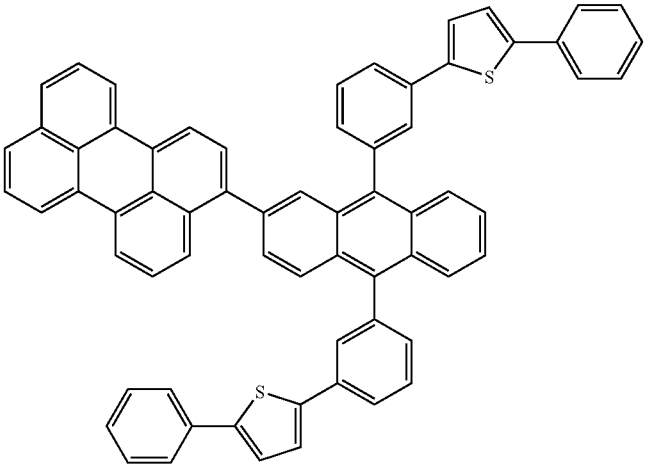 |
| 20 | 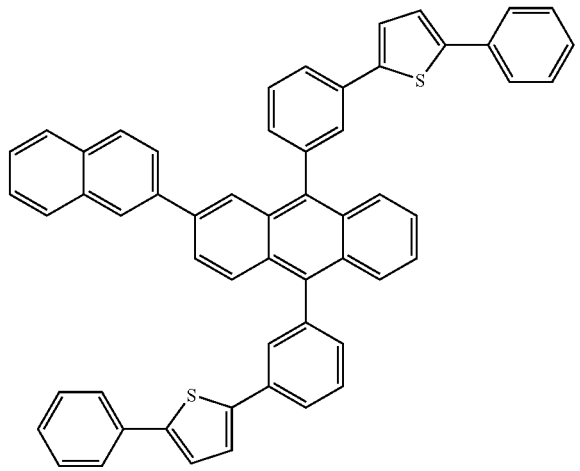 |
| 21 | 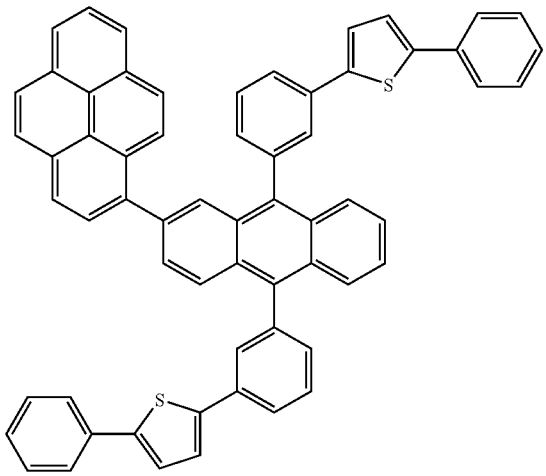 |

TABLE 1-continued

| Compound | Structural Formula |
|---|---|
| 22 | |
| 23 | |
| 24 | |

TABLE 1-continued
| Compound | Structural Formula |
|---|---|
| 25 | 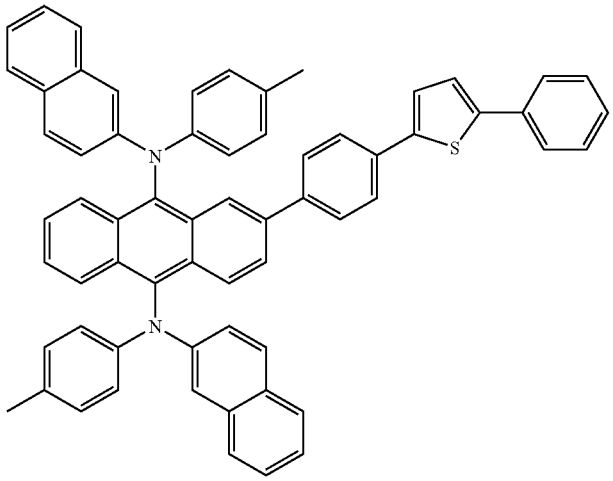 |
| 26 | 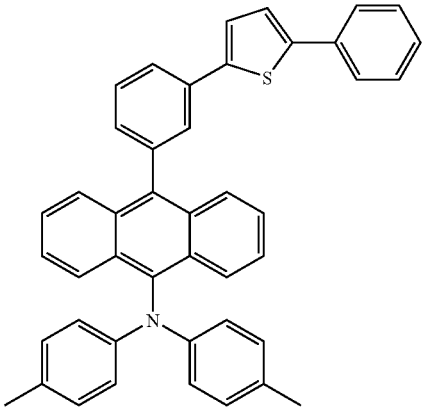 |
| 27 | 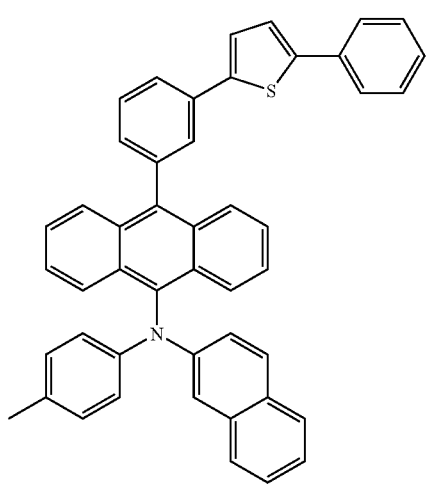 |

TABLE 1-continued
| Compound | Structural Formula |
| --- | --- |
| 28 | 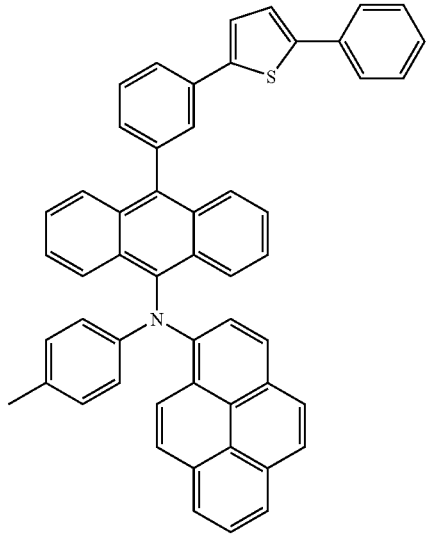 |
| 29 | 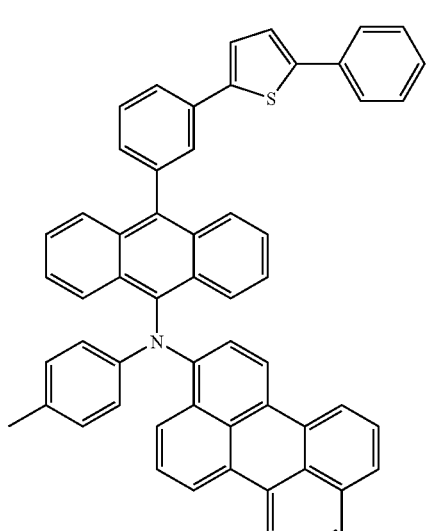 |
| 30 | 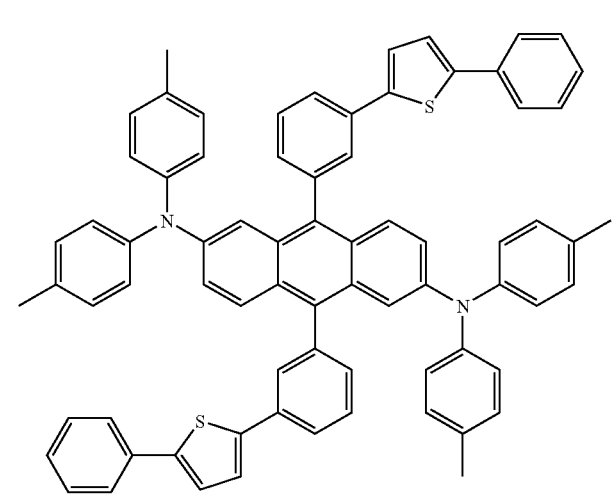 |

TABLE 1-continued
| Compound | Structural Formula |
|---|---|
| 31 | 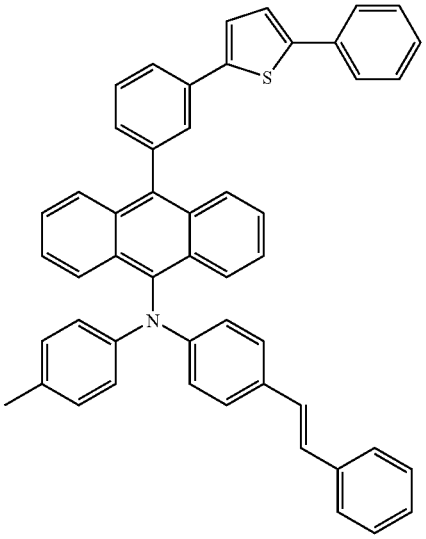 |
| 32 | 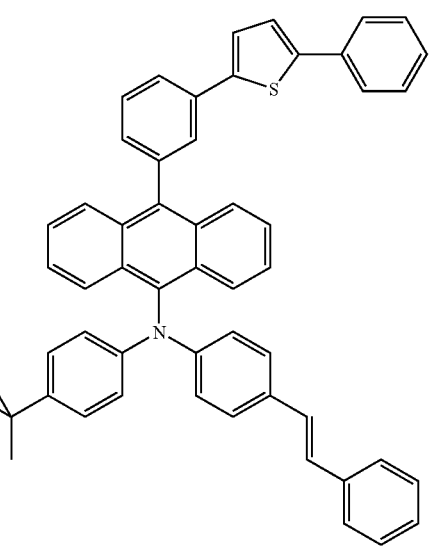 |
| 33 | 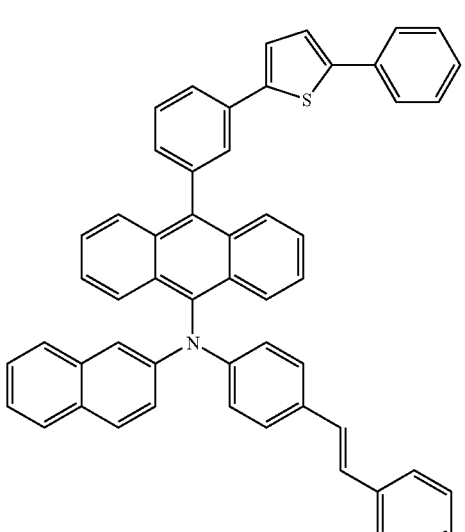 |

TABLE 1-continued
| Compound | Structural Formula |
|---|---|
| 34 | 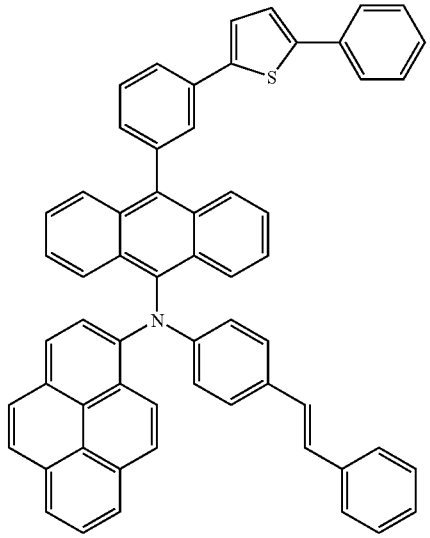 |
| 35 | 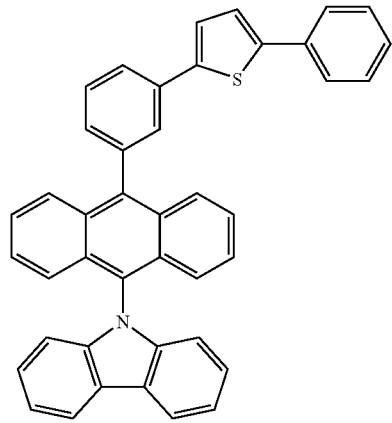 |
| 36 | 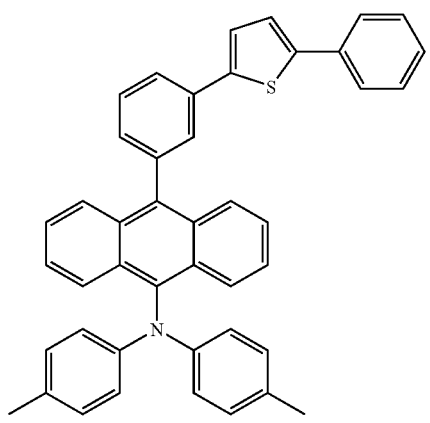 |

TABLE 1-continued
| Compound | Structural Formula |
|---|---|
| 37 | 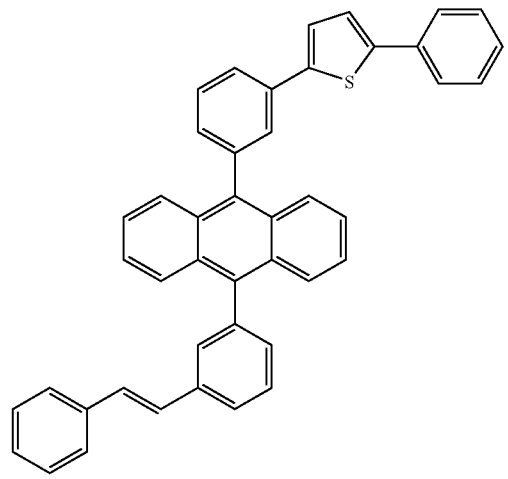 |
| 38 | 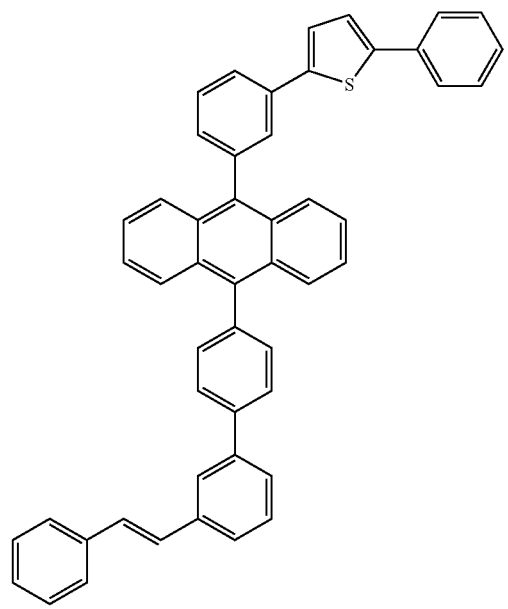 |

TABLE 1-continued
| Compound | Structural Formula |
|---|---|
| 39 | 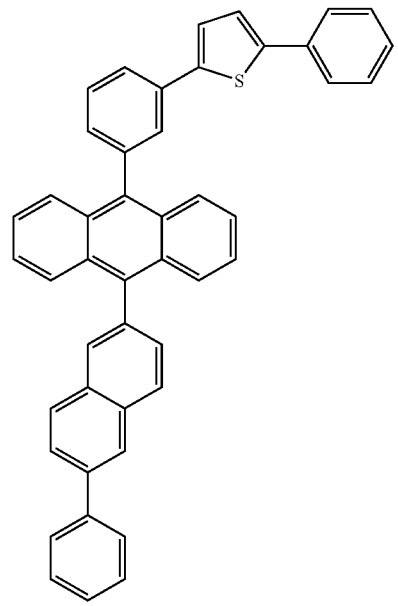 |
| 40 | 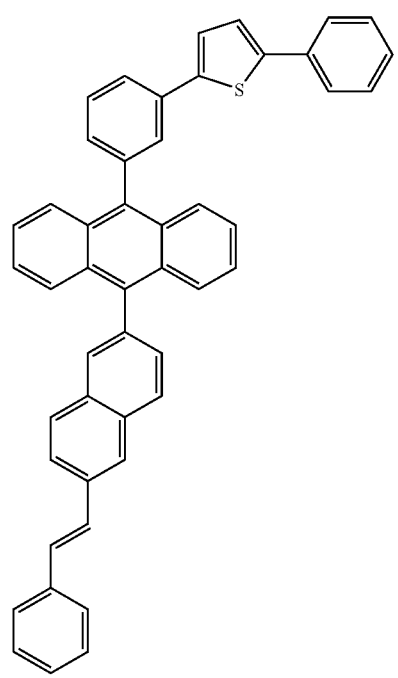 |

TABLE 1-continued
| Compound | Structural Formula |
| --- | --- |
| 41 | 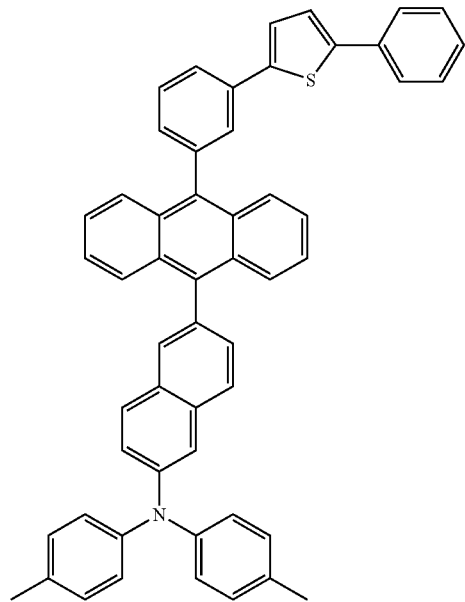 |
| 42 | 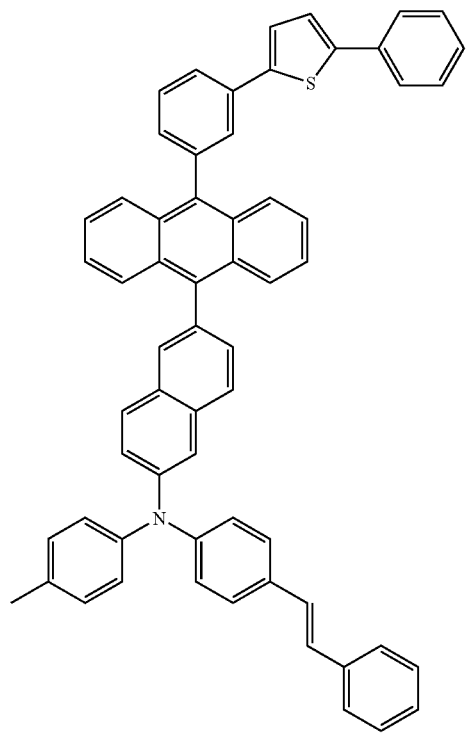 |

TABLE 1-continued

| Compound | Structural Formula |
| --- | --- |
| 43 | |
| 44 | |
| 45 | |

TABLE 1-continued
| Compound | Structural Formula |
| --- | --- |
| 46 | 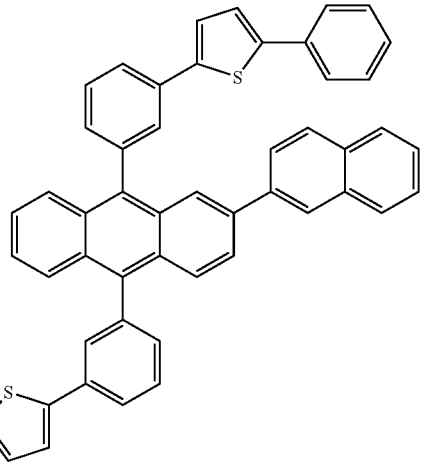 |
| 47 | 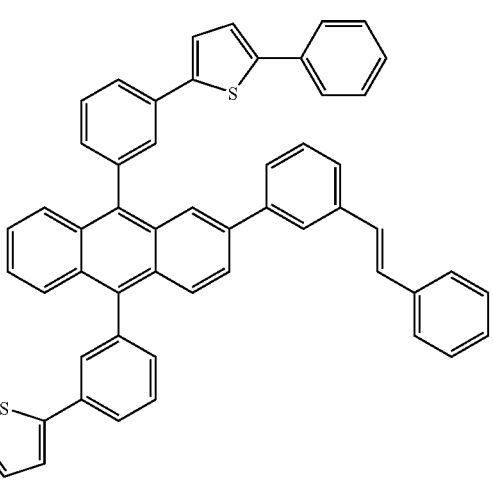 |
| 48 | 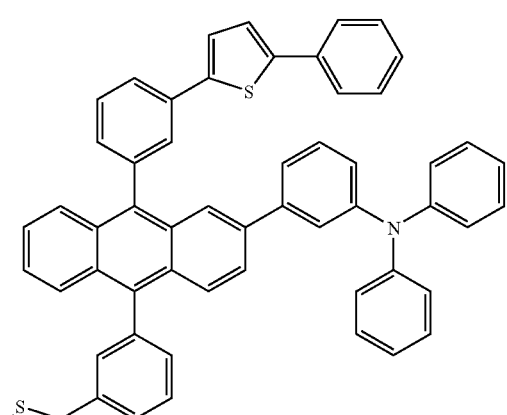 |

TABLE 1-continued

| Compound | Structural Formula |
| --- | --- |
| 49 | |
| 50 | |
| 51 | |

TABLE 1-continued

| Compound | Structural Formula |
| --- | --- |
| 52 | |
| 53 | |
| 54 | |

TABLE 1-continued
| Compound | Structural Formula |
|---|---|
| 55 | 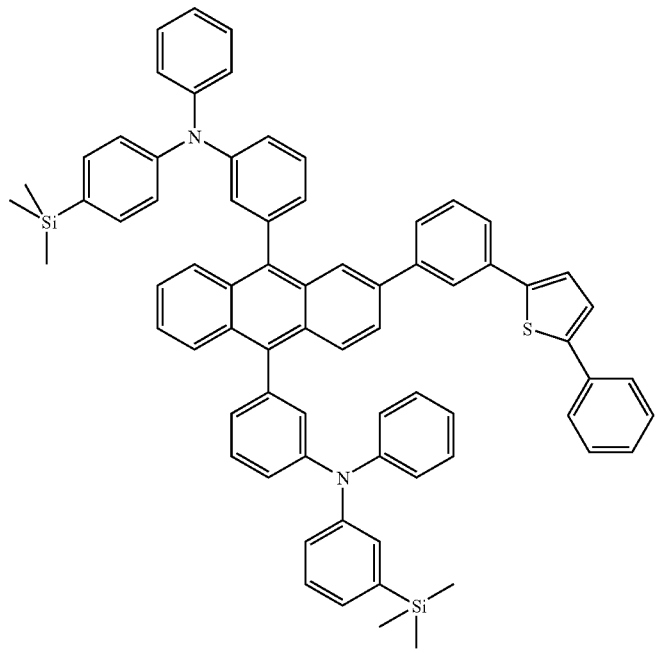 |
| 56 | 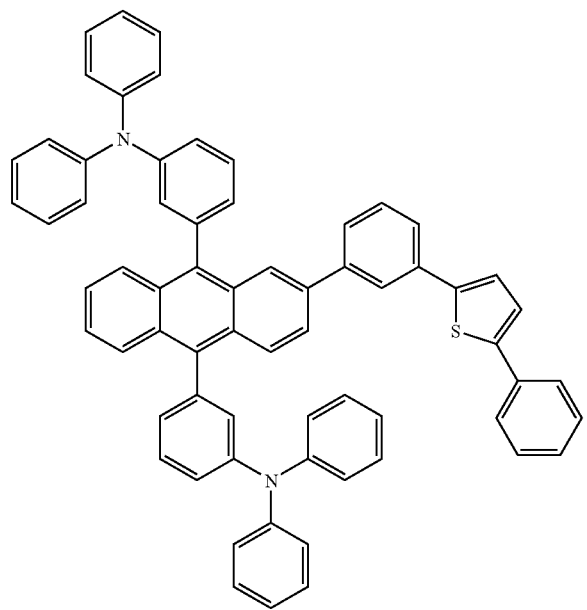 |

TABLE 1-continued
| Compound | Structural Formula |
| --- | --- |
| 57 | 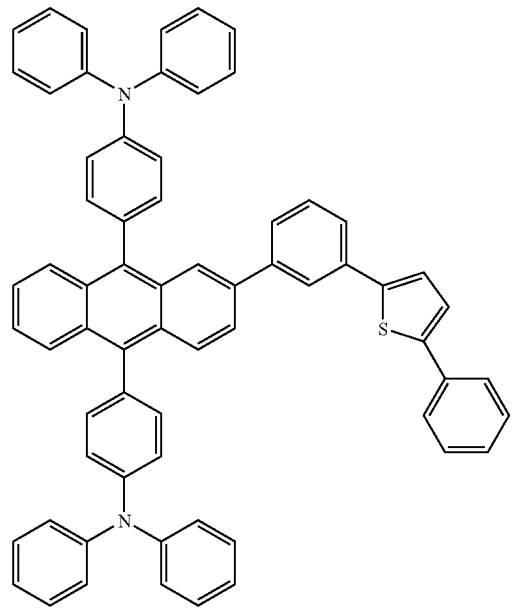 |
| 58 | 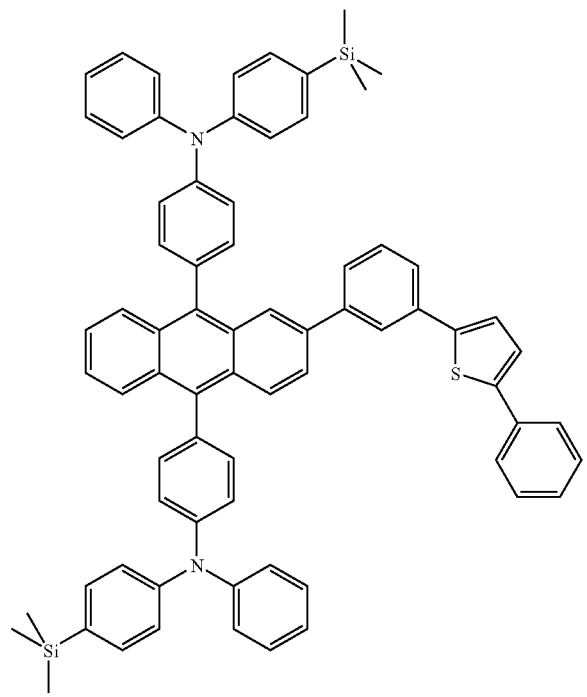 |

TABLE 1-continued
| Compound | Structural Formula |
|---|---|
| 59 | 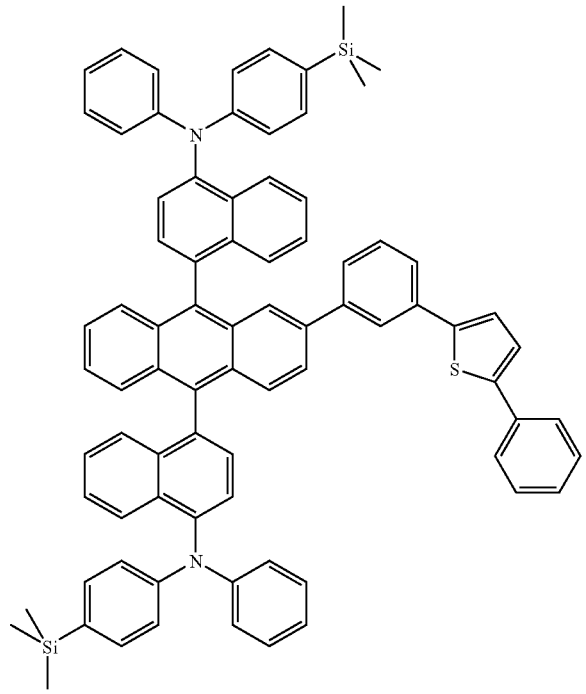 |
| 60 | 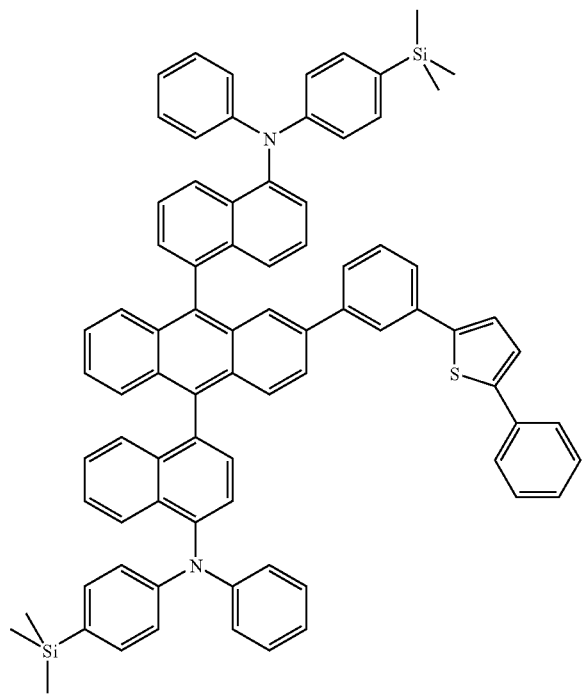 |

TABLE 1-continued
| Compound | Structural Formula |
|---|---|
| 61 | 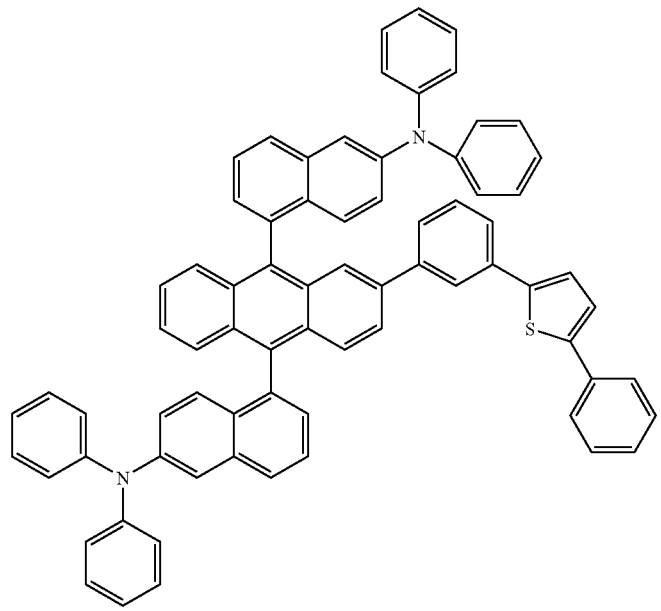 |
| 62 | 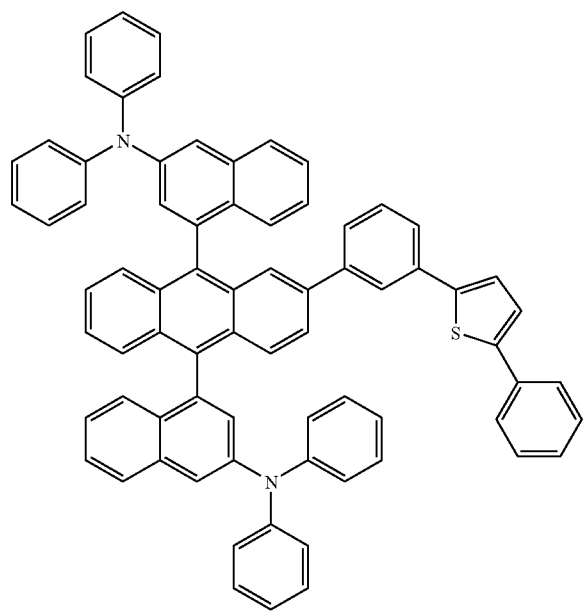 |

TABLE 1-continued
| Compound | Structural Formula |
|---|---|
| 63 | 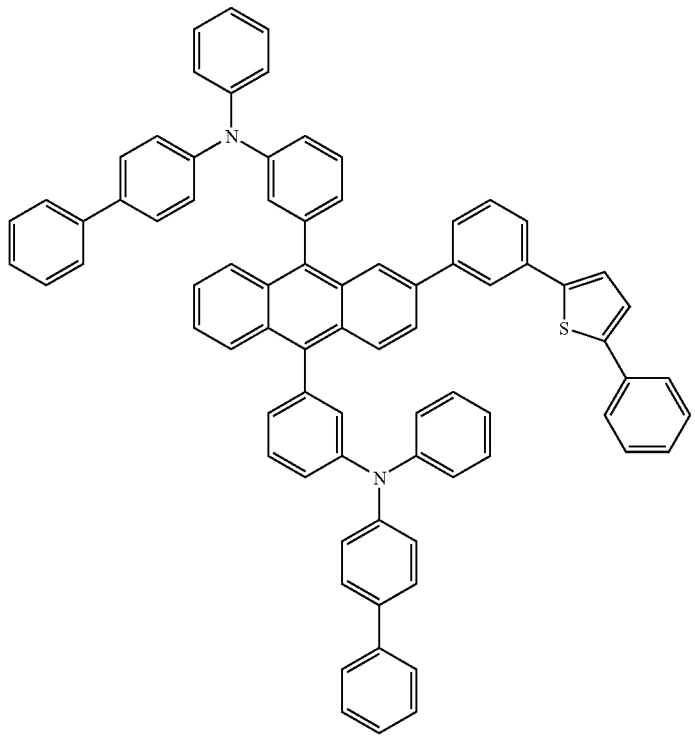 |
| 64 | 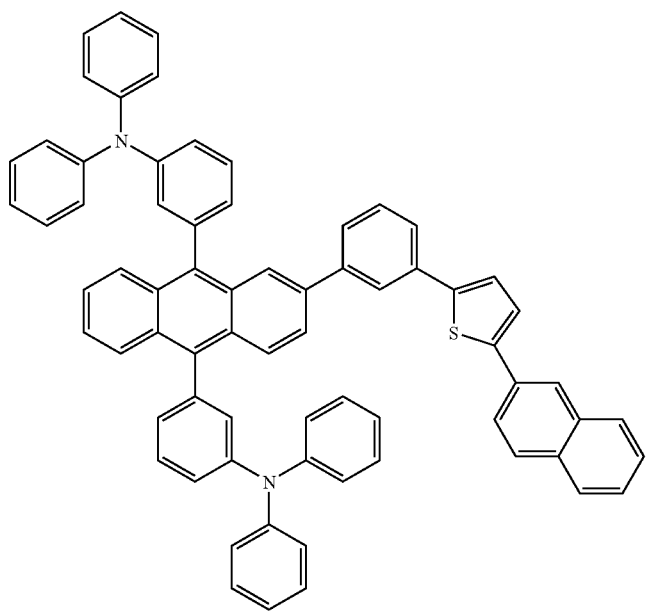 |

TABLE 1-continued
| Compound | Structural Formula |
|---|---|
| 65 | 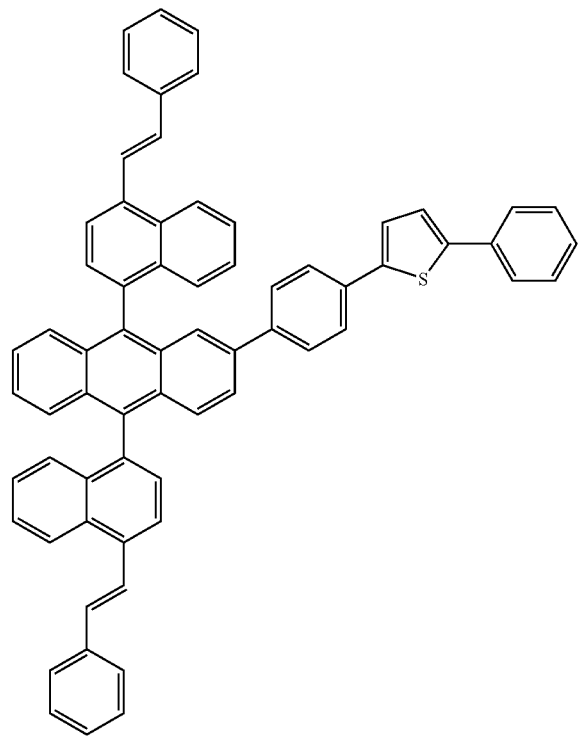 |
| 66 | 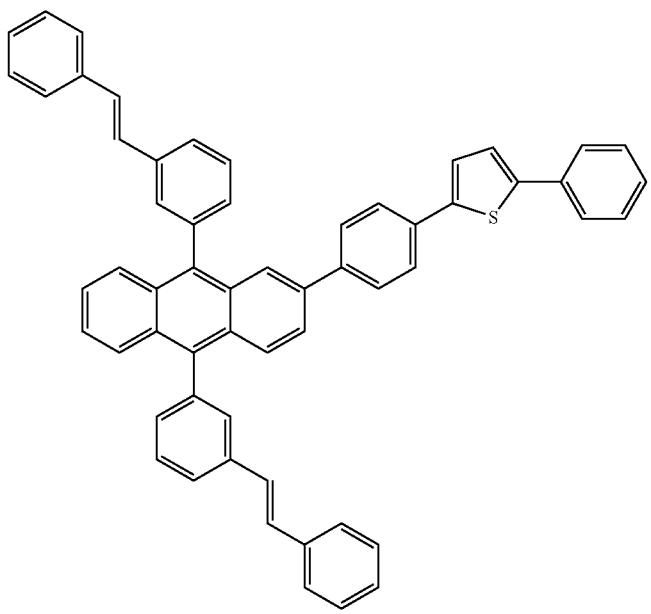 |

TABLE 1-continued

| Compound | Structural Formula |
| --- | --- |
| 67 | |
| 68 | |
| 69 | |

TABLE 1-continued

| Compound | Structural Formula |
|---|---|
| 70 | 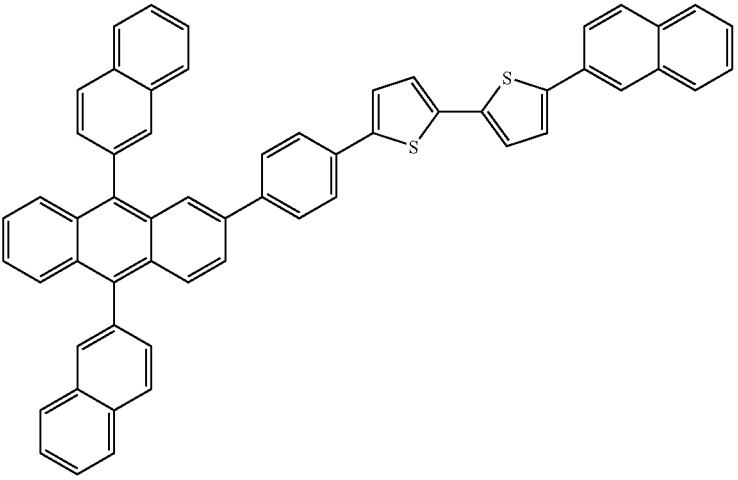 |

In the compounds of the formula 1, the compound of the formula 1 according to the present invention has a characteristic structure in which the anthracene derivative contains thiophene. The compound with such the structure containing thiophene has greatly increased light emission efficiency (quantum efficiency), as compared with that of the similar structure containing no thiophene. This is one of the critical characteristics which are required by both of the host and the dopant of the light emitting layer. Therefore, the light emitting efficiency of the device can be greatly improved by a novel structure represented by the formula 1. In particular, absolute light emitting efficiency of the dopant can be enhanced. FIG. 1 is a diagram showing a spectrum obtained by measuring the photoluminescences (PL) of the compound 5 solution according to the present invention and the comparative compound 1 solution (concentration: $1*10^{-5}$ M, solvent:toluene) at an exciting wavelength of 360 nm. The areas (energies) obtained by integrating the intensities of the spectrum at wavelengths of 360 to 600 nm were $1.0 \times E10$, $1.8 \times E10$, respectively. As shown in FIG. 1, the compound 5 according to the present invention showed about 2-times stronger light emitting characteristics than those of the comparative compound 1.

Specifically, in the structure of the compound 1 of the formula 1, for example, the thiophene-substituted phenyl moiety and the 9-(2-naphthyl)anthracene moiety are twisted at an angle of about 90 degree, and thus they are chemically bonded to each other, but do not greatly affect the conjugation, respectively. Accordingly, they can show independently light emission spectrum at the same or similar wavelength band.

The compound of the formula 1 according to the present invention can be prepared by using bromobenzene with a heterocyclic group being substituted and anthracene boronic acid as starting materials, and introducing a substituent thereto using an aryl-aryl coupling method. Specific methods for preparing the compound of the formula 1 according to the present invention are shown in Examples.

Further, the present invention provides an organic light emitting device comprising a first electrode, a second electrode, and at least one organic material layer interposed between the first electrode and the second electrode, wherein at least one layer of the organic material layers comprises the compound of the formula 1.

The above-described compounds of the present invention can singly serve as a light emitting material in the organic light emitting device, as well as serve as a light emitting dopant in combination of a suitable light emitting host, or as a light emitting host in combination of a suitable light emitting dopant.

The organic light emitting device of the present invention can be prepared by usual methods and materials for preparing an organic light emitting device, except that the above-described compounds according to the present invention are used to form at least one layer of the organic material layers, in particular a light emitting layer.

In one embodiment of the present invention, the organic light emitting device can have a structure comprising a first electrode, a second electrode, and organic material layers interposed therebetween. The structure of the organic light emitting device according to the present invention is illustrated in FIG. 3.

For example, the organic light emitting device according to the present invention can be prepared by depositing a metal, or a conductive metal oxide or an alloy thereof on a substrate using a PVD (physical vapor deposition) process such as sputtering and e-beam evaporation to form an anode; forming organic material layers comprising a hole injecting layer, a hole transporting layer, a light emitting layer and an electron transporting layer on the anode; and depositing a material, which can be used as a cathode, thereon. As an alternative, a cathode material, an organic material layer, and an anode material can be sequentially deposited on a substrate to prepare an organic light emitting device (see International Patent Application Publication No. 2003/012890).

The organic material layer may have a multilayer structure containing a hole injecting layer, a hole transporting layer, a light emitting layer, an electron transporting layer, and the like, but not limited thereto, and may have a monolayer structure. Further, the organic material layer can be produced to have a fewer number of layers, by using various polymer materials, by means of a solvent process, such as spin coating, dip coating, doctor blading, screen printing, ink jet printing, and heat transfer processes, instead of deposit process.

Preferably, the anode material is usually a material having a large work function to facilitate hole injection to the organic material layers. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene] (PEDT), polypyrrole and polyaniline, but not limited thereto.

The cathode material is preferably a material having a small work function to facilitate electron injection usually to the organic material layers. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is a material having high hole mobility, which can transfer holes from the anode or the hole injecting layer toward the light emitting layer. Specific examples thereof include organic materials of arylamine series, conductive polymers and block copolymers having both conjugated portions and non-conjugated portions, but are not limited thereto.

The light emitting material is capable of emitting visible light by accepting and re-combining holes from the hole transporting layer and electrons from the electron transporting layer, preferably a material having high quantum efficiency for fluorescence or phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; polyfluorene and rubrene, but are not limited thereto.

The electron transporting material is suitably a material having high electron mobility, which can transfer electrons from the cathode to the light emitting layer. Specific examples thereof include Al complexes of 8-hydroxyquinoline; complexes including $Alq_3$; organic radical compounds; and hydroxyflavone-metal complexes, but are not limited thereto.

The organic light emitting device according to the invention may be of a front-side, backside or double-sided light emission according to the materials used.

The compound according to the invention can function in an organic electronic device including an organic solar cell, an organic photoconductor and an organic transistor, according to a principle similar to that applied to the organic light emitting device.

ADVANTAGEOUS EFFECTS

The compound of the present invention is a novel structure of an anthracene derivative, and it can singly serve as a light emitting material in the organic light emitting device, as well as serve as a light emitting host in combination of a suitable dopant, or as a light emitting dopant in combination of a suitable host.

BRIEF DESCRIPTION OF THE DRAWINGS

FIG. 1 is a diagram showing a spectrum obtained by measuring the photoluminescences (PL) of the compound 5 solution according to the present invention and the comparative compound 1 solution (concentration: $1*10^{-5}$ M, solvent:toluene) at an exciting wavelength of 360 nm.

FIG. 2 is a diagram showing a spectrum obtained by measuring the photoluminescence of the compound 12 solution according to the present invention at an exciting wavelength of 434 nm.

FIG. 3 is a diagram illustrating the structure of the organic light emitting device according to one embodiment of the present invention.

MODE FOR THE INVENTION

Hereinafter, the present invention will be described in more detail by means of Examples and Experimental Examples, but the scope of the invention is not limited thereto.

Example 1

Preparation of Compound 5

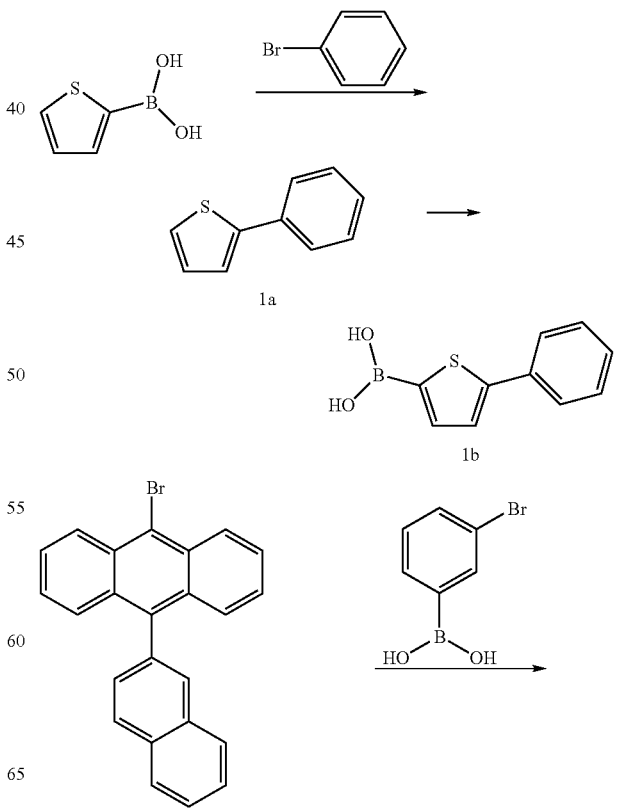

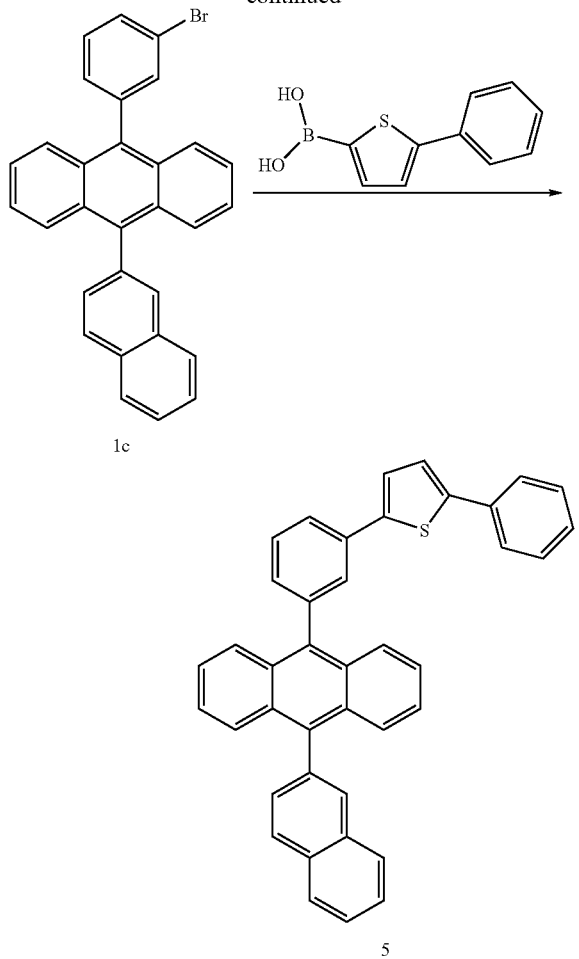

the separated aqueous solution layer, an aqueous hydrochloric acid solution was added, and the resulting precipitate was produced and filtered to obtain a compound 1b (2.7 g, 42%).

1-C. Preparation of Compound 1c

The compound 1b (2 g, 5.2 mmol) prepared in the step of 1-B and 3-bromophenyl boronic acid (1.04 g, 5.2 mmol) were dissolved in anhydrous THF (60 mL), and sequentially Pd(PPh$_3$)$_4$ (0.3 g, 0.26 mmol) and K$_2$CO$_3$ (1.0 g, 7.8 mmol) dissolved in H 0 (60 mL) were added thereto. The mixture was refluxed under stirring. Three hours later, the mixture was washed with brine, and the organic layer was extracted with ethyl acetate. Water was removed over magnesium sulfate, and the residue was filtered under reduced pressure, concentrated to remove the solvent, and separated by column chromatography to obtain a compound 1c (1.2 g, 50%). MS [M]=459

1-D. Preparation of Compound 5

The compound 1c (1 g, 2.18 mmol) prepared in the step of 1-C, the compound 1b (0.53 g, 2.6 mmol) prepared in the step of 1-B and Pd(PPh$_3$)$_4$ (0.13 g, 0.11 mmol) were dissolved in anhydrous THF (50 mL), and a 2M aqueous K$_2$CO$_3$ solution (50 mL) were added thereto, and then the mixture was refluxed under stirring for 3 hours. After completion of the reaction, the organic layer of the reaction solution was extracted with ethyl acetate, water was removed over magnesium sulfate, and the residue was filtered under reduced pressure, concentrated, and then separated by column chromatography to obtain a compound 5 (0.9 g, 80%). MS [M]=538

The spectrum obtained by measuring the photoluminescences (PL) of the compound 5 solution (concentration: $1*10^{-5}$ M, solvent:toluene) at an exciting wavelength of 360 nm is shown in FIG. 1.

Example 2

Preparation of Compound 7

1-A. Preparation of Compound 1a

A compound of 2-thiophene boronic acid (10 g, 78.1 mmol) and bromobenzene (7.48 mL, 70.3 mmol) was dissolved in anhydrous THF (300 mL), Pd(PPh$_3$)$_4$ (4.51 g, 3.91 mmol) and an aqueous K$_2$CO$_3$ solution (156 mL, 312.4 mmol) were then added thereto, and the mixture was refluxed for 3 hours. The organic layer was extracted with ethyl acetate, and water was removed over magnesium sulfate. The organic layer was filtered under reduced pressure, concentrated to remove the solvent, purified by column chromatography, and then recrystallized with THF and ethanol to obtain a white solid compound 1a (10 g, 80%). MS [M+H]=161

1-B. Preparation of Compound 1b

The compound 1a (5 g, 31.3 mmol) prepared in the step of 1-A was dissolved in anhydrous THF (200 mL), and the solution was cooled to −10° C., and n-butyllithium (15 mL, 37.5 mmol) was slowly added dropwise thereto. The mixture was stirred for 1 hour, and cooled to −78° C. again, boronic acid trimethylester (10.5 mL, 93.75 mmol) was slowly added thereto, and the mixture was stirred for 12 hours. The mixture was cooled to 0° C., a 10 wt % of an aqueous sulfuric acid solution (16 mL) was added thereto, and the mixture was stirred to obtain a white precipitate. The organic layer was extracted with THF, dried over magnesium sulfate, and then filtered under reduced pressure. This filtrate was concentrated to remove the solvent, dissolved in THF, an excessive amount of a 2 M aqueous NaOH solution was added thereto, and the organic layer was separated with dimethylchloromethane. To -continued

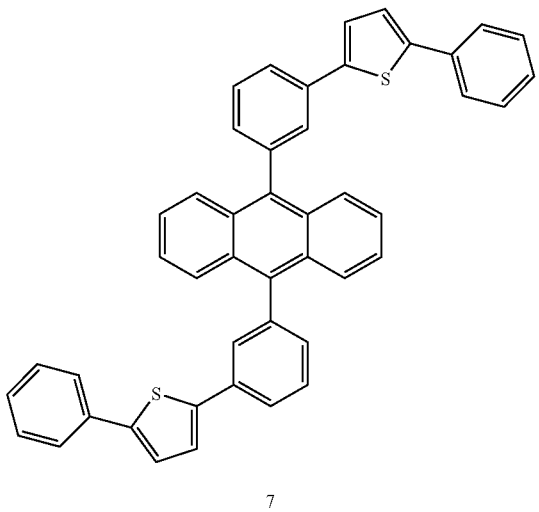

7

2-A. Preparation of Compound 2a 9,10-Dibromoanthracene (2 g, 5.95 mmol) and 3-bromophenyl boronic acid (2.4 g, 11.9 mmol) were dissolved in anhydrous THF (60 mL), and sequentially Pd(PPh$_3$)$_4$ (0.34 g, 0.30 mmol) and K$_2$CO$_3$ (1.8 g, 13.09 mmol) dissolved in H$_2$O (60 mL) were added thereto, and then the mixture was refluxed under stirring. Three hours later, the mixture was washed with brine, and the organic layer was extracted with ethyl acetate. Water was removed over magnesium sulfate, and the residue was filtered under reduced pressure, concentrated to remove the solvent, and separated by column chromatography to obtain a compound 2a (1.5 g, 50%). MS [M]=488

2-B. Preparation of Compound 7

The compound 2a (1.5 g, 3.07 mmol) prepared in the step of 2-A, the compound 1b (1.36 g, 6.76 mmol) prepared in the step of 1-B, and Pd(PPh$_3$)$_4$ (0.18 g, 0.15 mmol) were dissolved in anhydrous THF (50 mL) and then a 2 M aqueous K$_2$CO$_3$ solution (50 mL) was added thereto, and the mixture was refluxed under stirring for 3 hours. After completion of the reaction, the organic layer of the reaction solution was extracted with ethyl acetate, water was removed over magnesium sulfate, and the residue was filtered under reduced pressure, concentrated, and separated by column chromatography to obtain a compound 7 (1.7 g, 85%). MS [M]=646

Example 3

Preparation of Compound 12

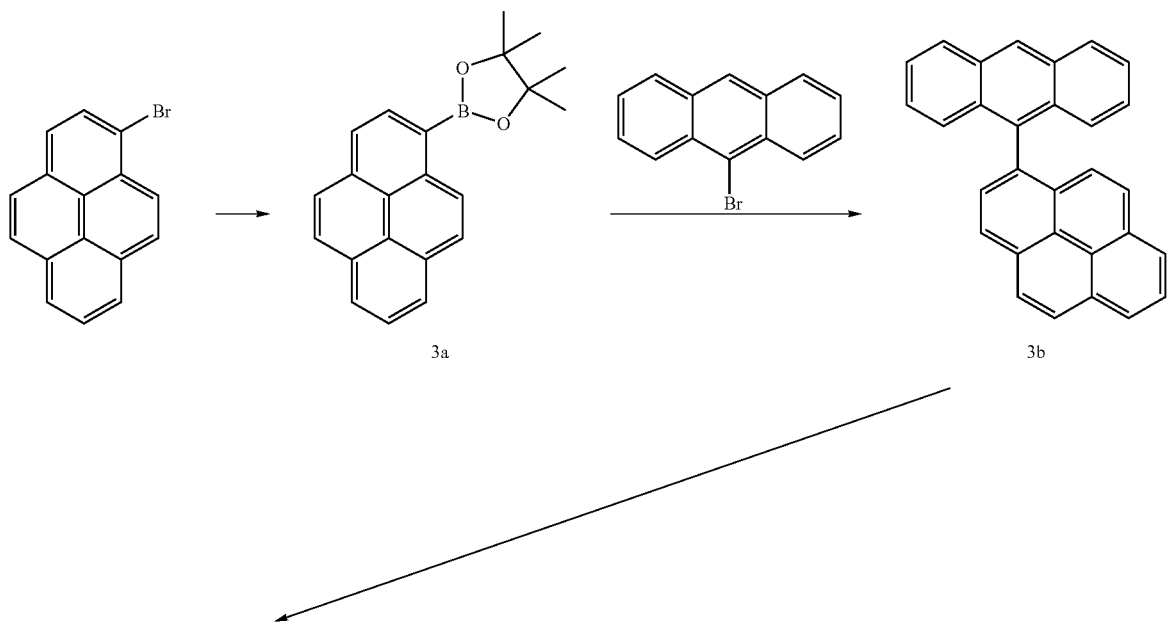

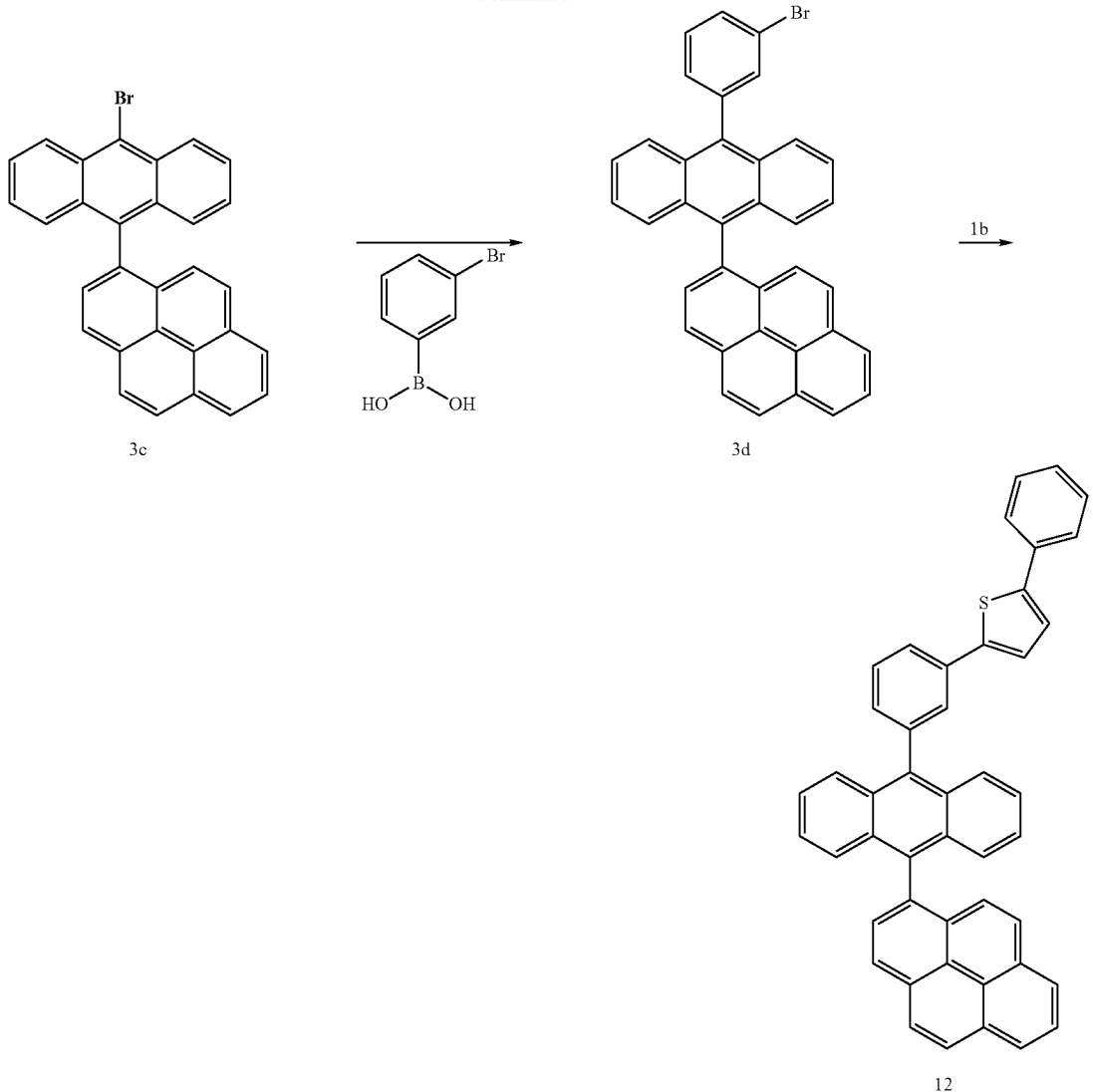

3-A. Preparation of Compound 3a

1-Bromo-pyrene (5 g, 17.8 mmol) was dissolved in anhydrous THF (60 mL), the solution was cooled to −78° C., and n-butyllithium (9.7 mL, 23.2 mmol) was slowly added dropwise thereto. The mixture was stirred for 30 minutes, 2-isopropyl-4,4,5,5-tetramethyl-[1,3,2]dioxaboron (4.8 mL, 23.1 mmol) was slowly added dropwise thereto, and the mixture was stirred for 12 hours. The reaction mixture was washed with an ammonium chloride solution, further washed with distilled water twice, and dried over magnesium sulfate to remove water. The residue was dissolved in THF, and recrystallized with EtOH to obtain a compound 3a (3.27 g, 56%).

3-B. Preparation of Compound 3b

The compound 3a (1.34 g, 4.08 mmol) prepared in the step of 3-A, and 9-bromoanthracene (1.05 g, 4.08 mmol) were dissolved in THF (30 mL), and Pd(PPh$_3$)$_4$ (0.24 g, 0.20 mmol) and then a 2 M aqueous K$_2$CO$_3$ solution (8.2 mL, 16.3 mmol) were added thereto, and the mixture was refluxed under stirring for 3 hours. The organic layer was extracted with ethyl acetate. Water was removed over magnesium sulfate, and the residue was filtered under reduced pressure, and then concentrated to remove the solvent. The residue was dissolved in THF, and recrystallized with ether to obtain a compound 3b (1.08 g, 70%). MS [M+H]=379

3-C. Preparation of Compound 3c

The compound 3b (1.08 g, 2.86 mmol) prepared in the step of 3-B was dissolved in DMF, and then N-bromosuccinimide (0.6 g, 3.43 mmol) was added thereto, and the mixture was stirred for 3 hours. To the solution, H$_2$O was added, and the resulting precipitate was produced, filtered under reduced pressure, dissolved in THF, and then recrystallized with ether to obtain a compound 3c (0.54 g, 41%). MS [M+H]=458

3-D. Preparation of Compound 3d

The compound 3c (0.54 g, 1.18 mmol) prepared in the step of 3-C and 3-bromophenyl boronic acid (0.24 g, 1.18 mmol) were dissolved in anhydrous THF (10 mL), and Pd(PPh$_3$)$_4$ (68 mg, 0.059 mmol) and a 2 M aqueous K$_2$CO$_3$ solution (2.4 mL, 4.72 mmol) were added thereto sequentially, and then the mixture was refluxed under stirring for 3 hours. The organic layer was extracted with ethyl acetate. Water was removed over magnesium sulfate, and the residue was filtered under reduced pressure, concentrated to remove the solvent, and then separated by column chromatography to obtain a compound 3d (0.24 g, 38%). MS [M]=533

3-E. Preparation of Compound 12

The compound 3d (0.24 g, 0.45 mmol) prepared in the step of 3-D and the compound 1b (0.11 g, 0.54 mmol) prepared in the step of 1-B of Example 1 were dissolved in anhydrous THF (10 mL), and Pd(PPh$_3$)$_4$ (26 mg, 0.03 mmol) and a 2 M aqueous K$_2$CO$_3$ solution (0.9 mL, 1.8 mmol) were added thereto sequentially, and then the mixture was refluxed under stirring for 3 hours. The organic layer of the reaction solution was extracted with ethyl acetate. Water was removed over magnesium sulfate, and the residue was filtered under reduced pressure, concentrated to remove the solvent, and then separated by column chromatography to obtain a compound 12 (0.12 g, 43%). MS [M+H]=613

The spectrum obtained by measuring the photoluminescences (PL) of the compound 12 solution (concentration: 1*10$^{-5}$ M, solvent:toluene) at an exciting wavelength of 434 nm is shown in FIG. 2.

Example 4

Preparation of Compound 14

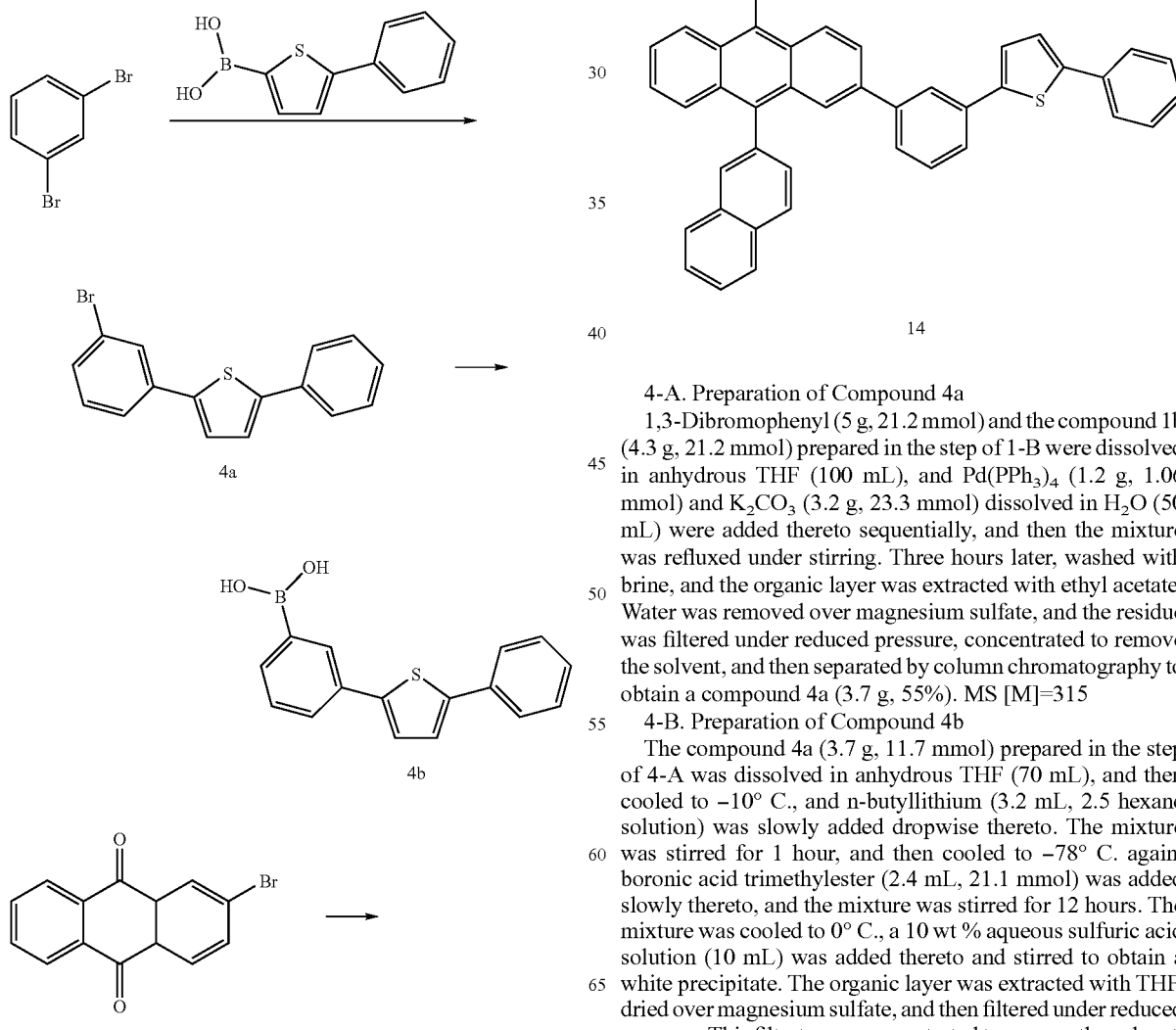
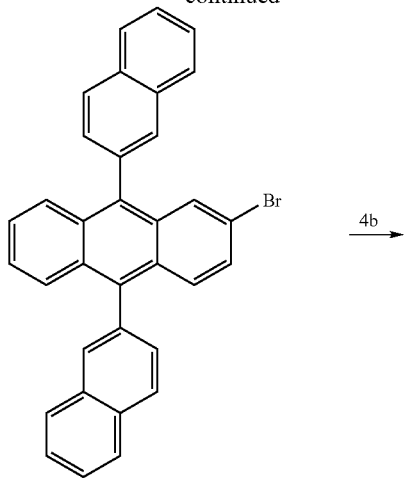
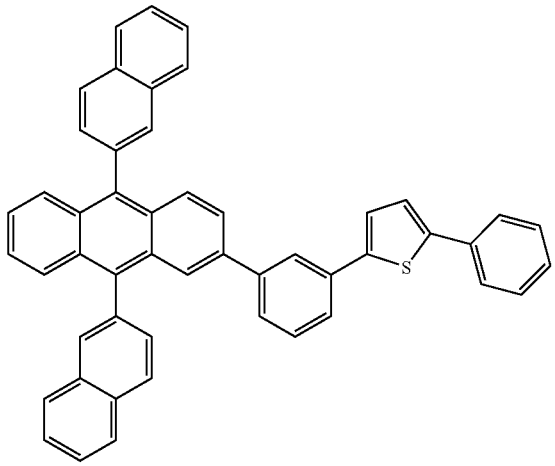

4-A. Preparation of Compound 4a 1,3-Dibromophenyl (5 g, 21.2 mmol) and the compound 1b (4.3 g, 21.2 mmol) prepared in the step of 1-B were dissolved in anhydrous THF (100 mL), and Pd(PPh$_3$)$_4$ (1.2 g, 1.06 mmol) and K$_2$CO$_3$ (3.2 g, 23.3 mmol) dissolved in H$_2$O (50 mL) were added thereto sequentially, and then the mixture was refluxed under stirring. Three hours later, washed with brine, and the organic layer was extracted with ethyl acetate. Water was removed over magnesium sulfate, and the residue was filtered under reduced pressure, concentrated to remove the solvent, and then separated by column chromatography to obtain a compound 4a (3.7 g, 55%). MS [M]=315

4-B. Preparation of Compound 4b

The compound 4a (3.7 g, 11.7 mmol) prepared in the step of 4-A was dissolved in anhydrous THF (70 mL), and then cooled to −10° C., and n-butyllithium (3.2 mL, 2.5 hexane solution) was slowly added dropwise thereto. The mixture was stirred for 1 hour, and then cooled to −78° C. again, boronic acid trimethylester (2.4 mL, 21.1 mmol) was added slowly thereto, and the mixture was stirred for 12 hours. The mixture was cooled to 0° C., a 10 wt % aqueous sulfuric acid solution (10 mL) was added thereto and stirred to obtain a white precipitate. The organic layer was extracted with THF, dried over magnesium sulfate, and then filtered under reduced pressure. This filtrate was concentrated to remove the solvent, dissolved in THF, an excessive amount of a 2 M aqueous NaOH solution was added thereto, and the organic layer was separated with dimethylchloromethane. To the separated aqueous solution layer, an aqueous hydrochloric acid solution was added, and the resulting precipitate was produced and filtered to obtain a compound 4b (1.8 g, 55%).

4-C. Preparation of Compound 4c

2-Bomonaphthalene (11.0 g, 53.1 mmol) was dissolved in anhydrous THF (100 mL) under a nitrogen atmosphere, the solution was cooled to −78° C., t-butyllithium (46.8 mL, 1.7 M pentane solution) was slowly added thereto, the solution was stirred at the same temperature for 1 hour, and then 2-bromoanthraquinone (6.36 g, 22.0 mmol) was added thereto. The cooling vessel was removed, and the mixture was stirred at normal temperature for 3 hours. To the reaction mixture, an aqueous ammonium chloride solution was added, and the mixture was extracted with methylene chloride. The organic layer was dried over anhydrous magnesium sulfate to remove the solvent. The resulting mixture was dissolved in a small amount of ethyl ether, and petroleum ether was added to the solution, and the mixture was stirred for several hours to obtain a solid compound. The solid compound was filtered, and then dried in vacuo to obtain dinaphthyl dialcohol (11.2 g, 93%). The dinaphtyl dialcohol (11.2 g, 20.5 mmol) was dispersed in 200 mL of acetic acid under a nitrogen atmosphere, to which potassium iodide (34 g, 210 mmol) and sodium hypophosphite hydrate (37 g, 420 mmol) were added. The resulting mixture was stirred under boiling for 3 hours. After cooling to normal temperature, the mixture was filtered and washed with water and methanol, and then dried in vacuo to obtain a pale yellow compound 4c (7.2 g, 64%). MS [M]=509

4-D. Preparation of Compound 14

The compound 4c (2.7 g, 5.4 mmol) prepared in the step of 4-C and the compound 4b (1.8 g, 6.4 mmol) prepared in the step of 4-B were dissolved in anhydrous THF (70 mL), and Pd(PPh$_3$)$_4$ (0.3 g, 0.27 mmol) and a 2 M aqueous K$_2$CO$_3$ solution (20 mL) were added thereto sequentially, and then the mixture was refluxed under stirring for 12 hours. The organic layer of the reaction solution was extracted with ethyl acetate. Water was removed over magnesium sulfate, and the residue was filtered under reduced pressure, concentrated to remove the solvent, dissolved in THF, and crystallized with ethanol to obtain a compound 14 (2.9 g, 82%). MS [M+H]= 665

Example 5

Preparation of Compound 18

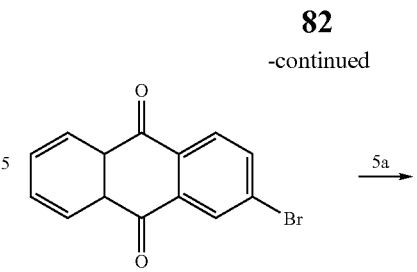

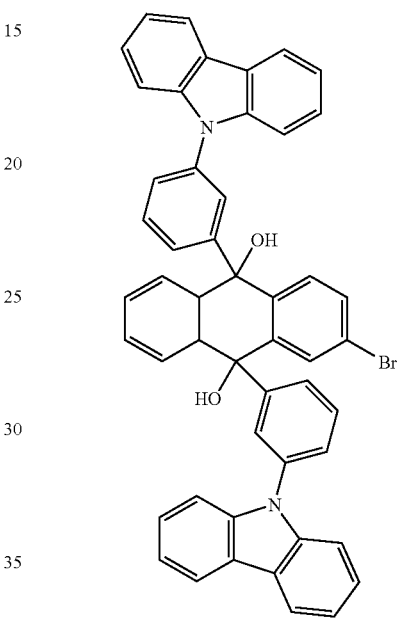

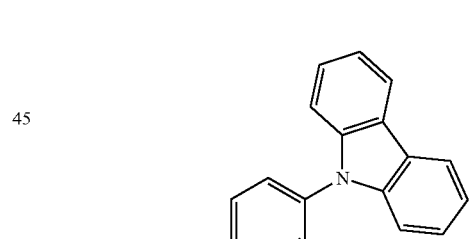

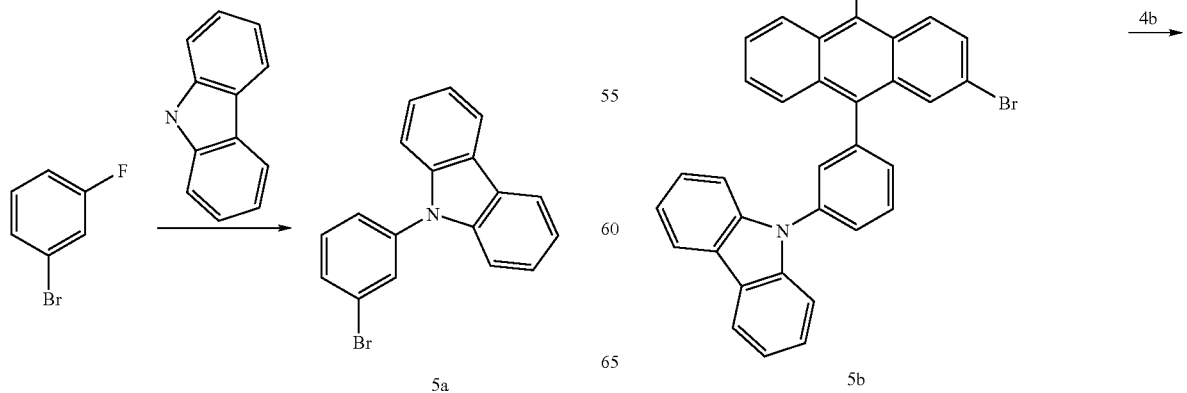

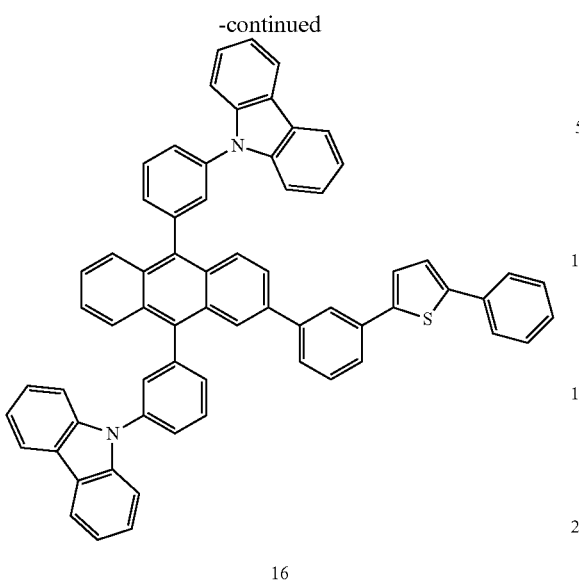

16

5-A. Preparation of Compound 5a

1-Bromo-3-fluorobenzene (6.3 g, 35.9 mmol), carbazole (5 g, 29.9 mmol), potassium fluoride-alumina (40 wt %, 8.65 g, 59.8 mmol), and 18-crown-6 (0.8 g, 2.99 mmol) were dissolved in dimethylsulfoxide (DMSO, 75 mL), and the solution was stirred at a temperature above 150° C. for 12 hours. The reaction solution was cooled, and then alumina was filtered over magnesium sulfate. The filtrate was subject to phase separation with methyl t-butyl ether (300 mL) and then washed with water. The organic layer was distilled off under reduced pressure, and then separated by column chromatography (solvent:hexane solution) to obtain a compound 5a (3 g, 26%). MS [M]=322

5-B. Preparation of Compound 5b

The compound 5a (3.0 g, 9.3 mmol) prepared in the step of 5-A was dissolved in anhydrous THF (100 mL) under a nitrogen atmosphere, the solution was cooled to −78° C., t-butyllithium (8 mL, 1.7 M pentane solution) was slowly added thereto, the solution was stirred at the same temperature for 1 hour, and then 2-bromoanthraquinone (1.22 g, 4.2 mmol) was added thereto. The cooling vessel was removed, and the mixture was stirred at normal temperature for 3 hours. To the reaction mixture, an aqueous ammonium chloride solution was added, and the mixture was extracted with methylene chloride. The organic layer was dried over anhydrous magnesium sulfate to remove the solvent. The resulting mixture was dissolved in a small amount of ethyl ether, and petroleum ether was added to the solution, and then the mixture was stirred for several hours to obtain a solid compound. The solid compound was filtered, and then dried in vacuo to obtain dicarbazolephenyl dialcohol (2.9 g, 90%). The dicarbazolephenyl dialcohol (2.9 g, 3.8 mmol) was dispersed in 50 mL of acetic acid under a nitrogen atmosphere, to which potassium iodide (6.5 g, 39 mmol) and sodium hypophosphite hydrate (6.87 g, 78 mmol) were added. The resulting mixture was stirred under boiling for 3 hours. After cooling to normal temperature, the mixture was filtered and washed with water and methanol, and then dried in vacuo to obtain a compound 5b (1.9 g, 67%). MS [M]=739

5-C. Preparation of Compound 18

The compound 5b (1.9 g, 2.6 mmol) prepared in the step of 5-B and the compound 4b (0.87 g, 3.1 mmol) prepared in the step of 4-B of Example 4 were dissolved in anhydrous THF (70 mL), and Pd(PPh₃)₄ (0.15 g, 0.13 mmol) and a 2 M aqueous K₂CO₃ solution (20 mL) were added thereto sequentially, and then the mixture was refluxed under stirring for 12 hours. The organic layer of the reaction solution was extracted with ethyl acetate. Water was removed over magnesium sulfate, and the residue was filtered under reduced pressure, concentrated, and the recrystallized with THF and ethanol to obtain a compound 18 (1.9 g, 85%). MS [M+H]=895

Example 6

Preparation of Compound 22

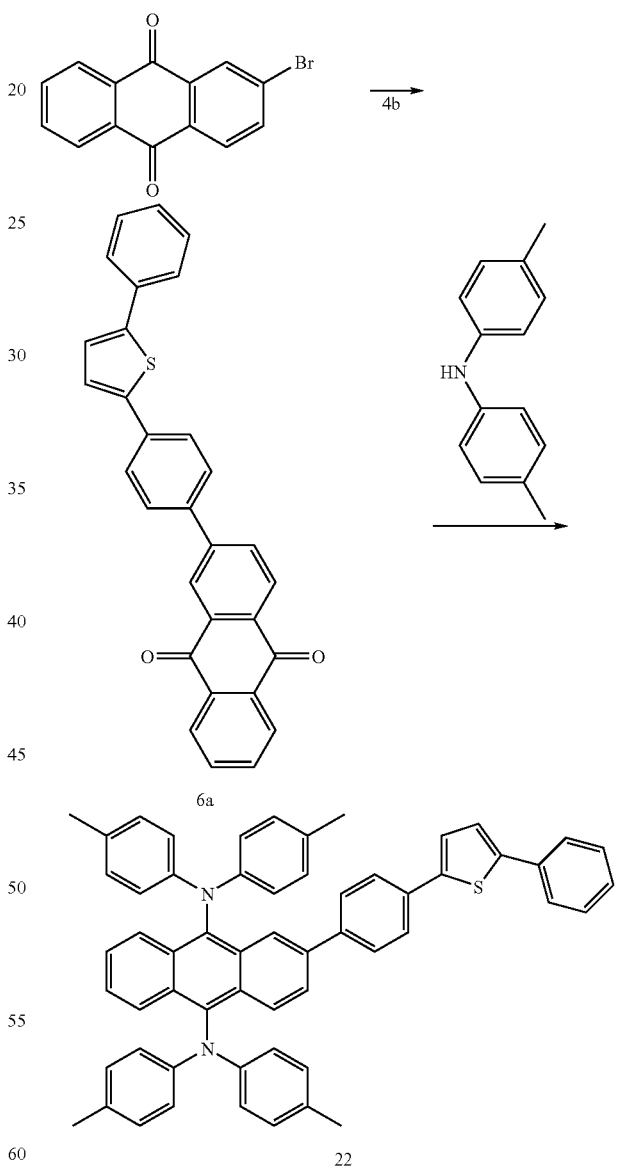

6-A. Preparation of Compound 6a

2-Bromoanthraquinone (3 g, 10.4 mmol) and compound 4b (4.4 g, 15.7 mmol) prepared in the step of 4-B of Example 4 were dissolved in anhydrous THF (100 mL), and Pd(PPh₃)₄ (0.36 g, 0.31 mmol) and a 2 M aqueous K₂CO₃ solution (70 mL) were added thereto sequentially, and then the mixture was refluxed under stirring for 12 hours. The organic layer of the reaction solution was extracted with ethyl acetate. Water was removed over magnesium sulfate, and the residue was filtered under reduced pressure, concentrated, and the recrystallized with THF and ethanol to obtain a compound 6a (3.8 g, 83%). MS [M]=442

6-B. Preparation of Compound 22

The compound 6a (3 g, 7.1 mmol) prepared in the step of 6-A, p-tolylamine (5.6 g, 28.4 mmol), and pyridine (2.3 mL, 28.4 mmol) were dissolved in benzene (100 mL), and then titanium tetrachloride (5.4 g, 28.4 mmol) was added dropwise thereto at 10° C., and the mixture was stirred at room temperature for 20 hours. Then, the mixture was diluted with water (100 mL), neutralized with an aqueous sodium oxide solution, extracted with ethyl acetate, and then concentrated. The residue was separated by column chromatography to obtain a compound 22 (1.7 g, 30%). MS [M]=802

Example 7

Preparation of Compound 28

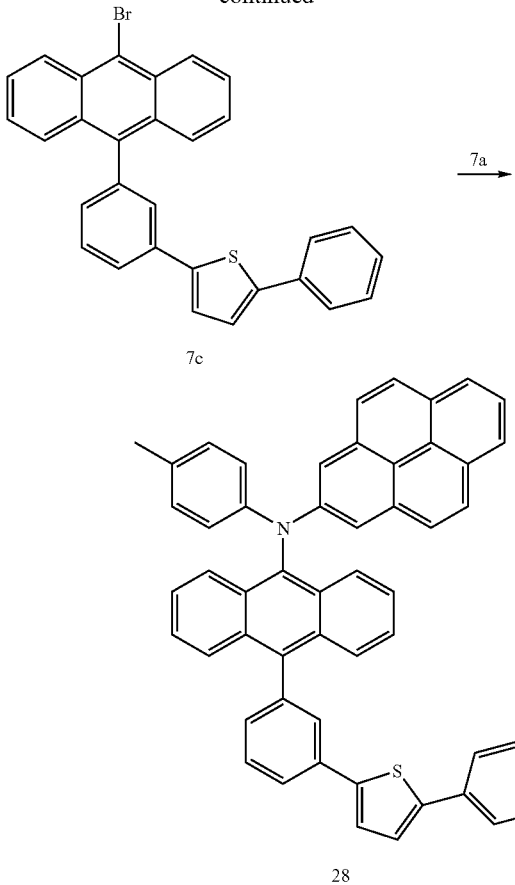

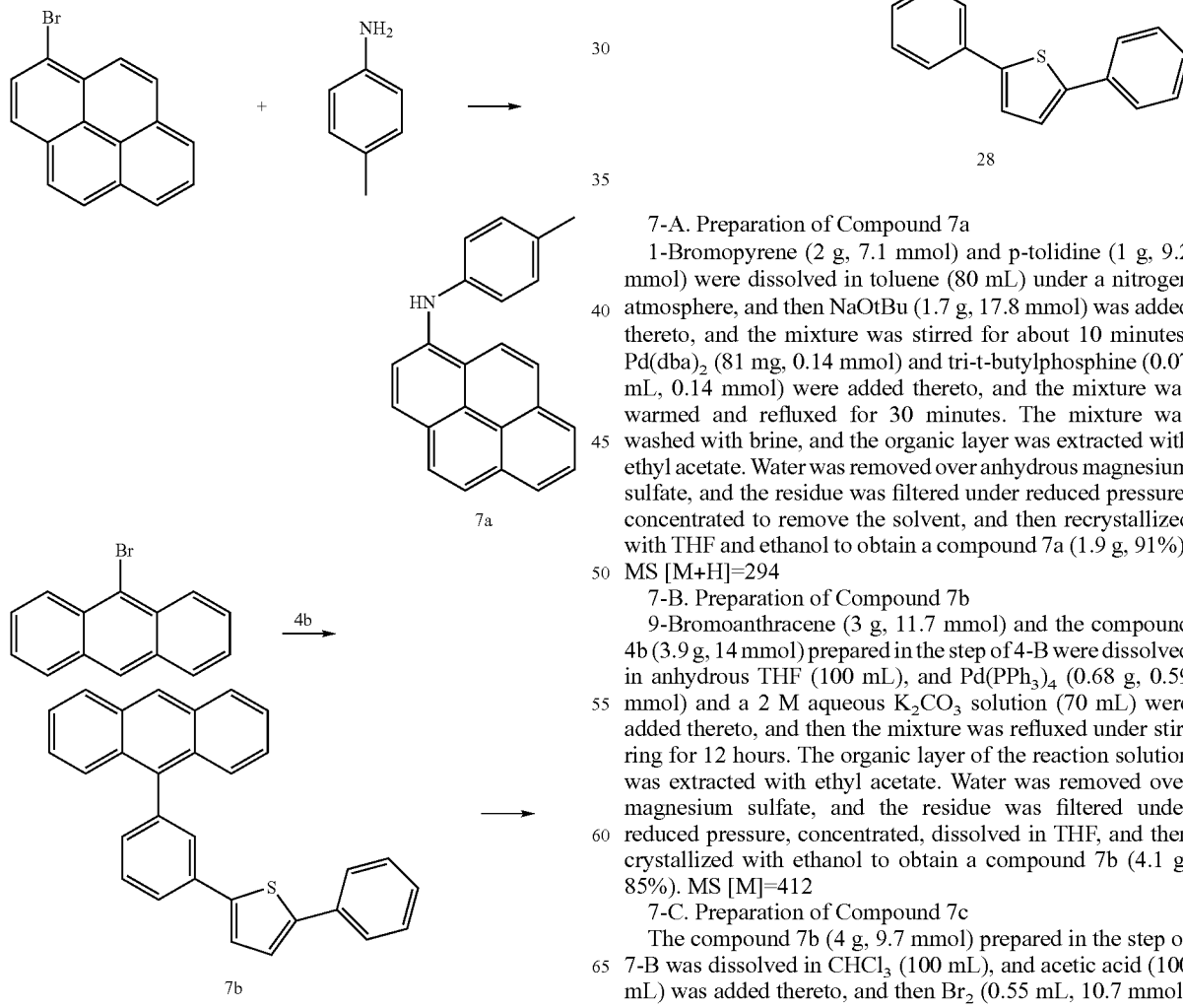

7-A. Preparation of Compound 7a

1-Bromopyrene (2 g, 7.1 mmol) and p-tolidine (1 g, 9.2 mmol) were dissolved in toluene (80 mL) under a nitrogen atmosphere, and then NaOtBu (1.7 g, 17.8 mmol) was added thereto, and the mixture was stirred for about 10 minutes. Pd(dba)$_2$ (81 mg, 0.14 mmol) and tri-t-butylphosphine (0.07 mL, 0.14 mmol) were added thereto, and the mixture was warmed and refluxed for 30 minutes. The mixture was washed with brine, and the organic layer was extracted with ethyl acetate. Water was removed over anhydrous magnesium sulfate, and the residue was filtered under reduced pressure, concentrated to remove the solvent, and then recrystallized with THF and ethanol to obtain a compound 7a (1.9 g, 91%). MS [M+H]=294

7-B. Preparation of Compound 7b

9-Bromoanthracene (3 g, 11.7 mmol) and the compound 4b (3.9 g, 14 mmol) prepared in the step of 4-B were dissolved in anhydrous THF (100 mL), and Pd(PPh$_3$)$_4$ (0.68 g, 0.59 mmol) and a 2 M aqueous K$_2$CO$_3$ solution (70 mL) were added thereto, and then the mixture was refluxed under stirring for 12 hours. The organic layer of the reaction solution was extracted with ethyl acetate. Water was removed over magnesium sulfate, and the residue was filtered under reduced pressure, dissolved in THF, and then crystallized with ethanol to obtain a compound 7b (4.1 g, 85%). MS [M]=412

7-C. Preparation of Compound 7c

The compound 7b (4 g, 9.7 mmol) prepared in the step of 7-B was dissolved in CHCl$_3$ (100 mL), and acetic acid (100 mL) was added thereto, and then Br$_2$ (0.55 mL, 10.7 mmol) was added dropwise to the mixture at 0° C. The mixture was warmed to room temperature, and the mixture was stirred for 5 hours. After completion of the reaction, the reaction solution was concentrated, and recrystallized with EtOH to obtain a compound 7c (3.5 g, 71%). MS [M]=491

7-D. Preparation of Compound 28

The compound 7c (3.5 g, 7.1 mmol) prepared in the step of 7-C and the compound 7a (1 g, 9.2 mmol) prepared in the step of 7-A were dissolved in toluene (80 mL) under a nitrogen atmosphere, and then NaOtBu (1.7 g, 17.8 mmol) was added thereto, and the mixture was stirred for about 10 minutes. Pd(dba)$_2$ (81 mg, 0.14 mmol) and tri-t-butylphosphine (0.07 mL, 0.14 mmol) were added thereto, and the mixture was warmed and refluxed for 30 minutes. The mixture was washed with brine, and the organic layer was extracted with ethyl acetate. Water was removed over anhydrous magnesium sulfate, and the residue was filtered under reduced pressure, concentrated to remove the solvent, and then recrystallized with THF and ethanol to obtain a compound 28 (1.9 g, 91%). MS [M+H]=704

Example 8

Preparation of Compound 31

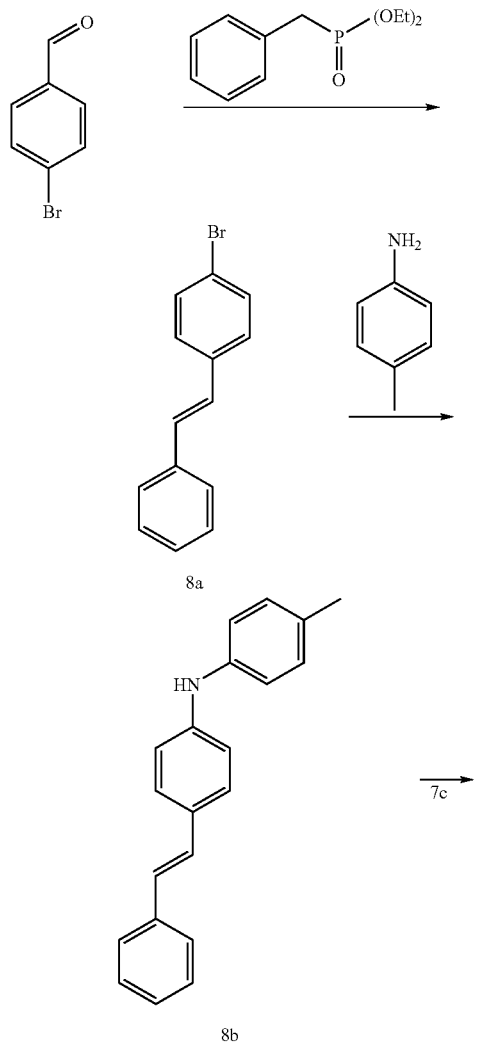

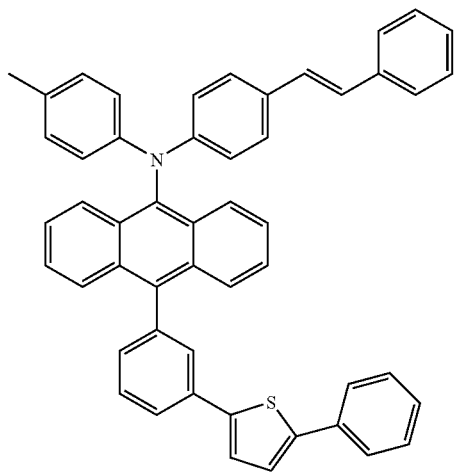

31

8-A. Preparation of Compound 8a

NaH (3 g, 75 mmol) and 18-crown-6 (1.43 g, 5.4 mmol) were dissolved in THF (100 mL) under a nitrogen atmosphere, and benzyl phosphonic acid diethyl ester (13.5 mL, 65 mmol) was added thereto. Under cooling the mixture (0° C.), 4-bromobenzenealdehyde (10 g, 54 mmol) was added slowly thereto. The mixture was stirred for 4 hours at normal temperature. To the reaction solution, water was added, and the mixture was extracted with ether, dried over magnesium sulfate, distilled off under reduced pressure, and recrystallized with ethanol to obtain a compound 8a (10 g, 75%). MS [M]=295

8-B. Preparation of Compound 8b

The compound 8a (5 g, 16.9 mmol) prepared in the step of 8-A, and p-tolidine (2.2 g, 20.3 mmol) were dissolved in toluene (80 mL) under a nitrogen atmosphere, and then NaOtBu (4.8 g, 50.7 mmol) was added thereto, and the mixture was stirred for about 10 minutes. Pd(dba)$_2$ (0.31 g, 0.34 mmol) and tri-t-butylphosphine (0.15 g, 0.5 mmol) were added thereto, and the mixture was warmed and refluxed for 30 minutes. The mixture was washed with brine, and the organic layer was extracted with ethyl acetate. Water was removed over anhydrous magnesium sulfate, and the residue was filtered under reduced pressure, concentrated to remove the solvent, and then re-crystallized with THF and ethanol to obtain a compound 8b (4.4 g, 92%). MS [M+H]=286

8-C. Preparation of Compound 31

The compound 7c (3.5 g, 7.1 mmol) prepared in the step of 7-C, and the compound 8b (2.6 g, 9.2 mmol) prepared in the step of 8-B were dissolved in toluene (80 mL) under a nitrogen atmosphere, and then NaOtBu (2.0 g, 21.3 mmol) was added thereto, and the mixture was stirred for about 10 minutes. Pd(dba)$_2$ (0.13 g, 0.14 mmol) and tri-t-butylphosphine (0.07 mL, 0.14 mmol) were added thereto, and the mixture was warmed and refluxed for 30 minutes. The mixture was washed with brine, and the organic layer was extracted with ethyl acetate. Water was removed over anhydrous magnesium sulfate, and the residue was filtered under reduced pressure, concentrated to remove the solvent, and then recrystallized with THF and ethanol to obtain a compound 31 (1.9 g, 91%). MS [M+H]=696

Example 9

Preparation of Compound 43

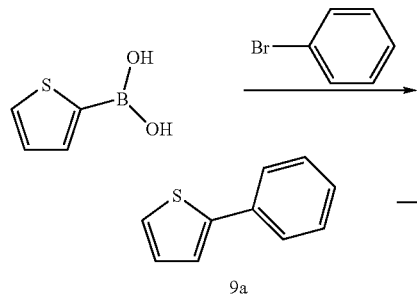

9a

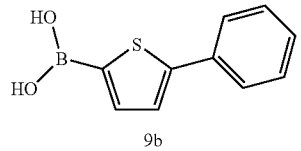

9b

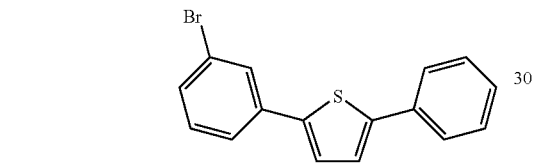

9c

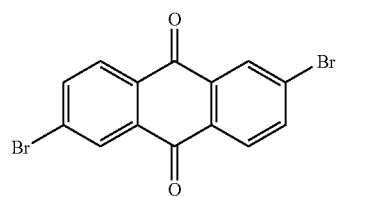

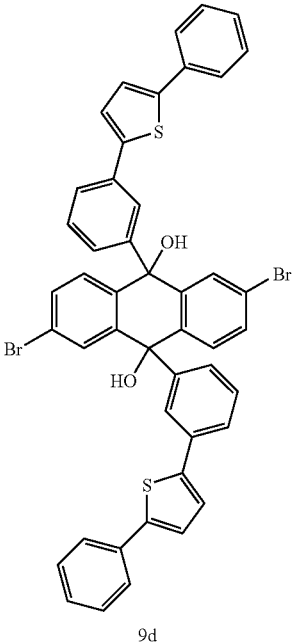

9d

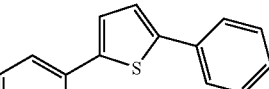

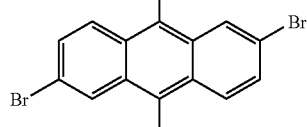

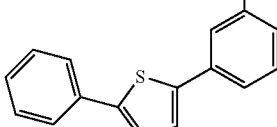

9e

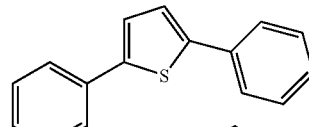

43

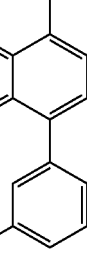

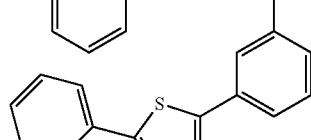

9-A. Synthesis of Compound 9a 2-thiophene boronic acid (10 g, 78.1 mmol) and bromobenzene (7.48 mL, 70.3 mmol) were dissolved in anhydrous THF (300 mL), and Pd(PPh$_3$)$_4$ (4.51 g, 3.91 mmol) and an aqueous K$_2$CO$_3$ solution (156 mL, 312.4 mmol) were added thereto sequentially, and then the mixture was refluxed for 3 hours. The organic layer was extracted with ethyl acetate, and water was removed over magnesium sulfate. The organic layer was filtered under reduced pressure, concentrated to remove the solvent, purified by column chromatography, and then recrystallized with THF and ethanol to obtain a white solid compound 9a (10 g, 80%). MS [M+H] 161

9-B. Synthesis of Compound 9b

The compound 9a (5 g, 31.3 mmol) prepared in the step of 9-A was dissolved in anhydrous THF (200 mL), and the solution was cooled to −10° C., and n-butyllithium (15 mL, 37.5 mmol) was slowly added dropwise thereto. After the mixture was stirred for 1 hour, and cooled to −78° C. again, boronic acid trimethylester (10.5 mL, 93.75 mmol) was slowly added thereto, and the mixture was stirred for 12 hours. The mixture was cooled to 0° C., a 2 N aqueous hydrochloric acid solution (16 mL) was added thereto, and the mixture was stirred to obtain a white precipitate. The organic layer was extracted with THF, dried over magnesium sulfate, and then filtered under reduced pressure. This filtrate was concentrated to remove the solvent, dissolved in THF, an excessive amount of an aqueous solution was added thereto, and the organic layer was separated with dimethylchloromethane. To the separated aqueous solution layer, an aqueous hydrochloric acid solution was added, and the resulting precipitate was produced and filtered to obtain a compound 9b (2.7 g, 42%).

9-C. Synthesis of Compound 9c

3-Bromoiodobenzene (3.5 g, 12.3 mmol) and the compound 9b (2.5 g, 12.3 mmol) prepared in the step of 9-B were dissolved in anhydrous THF (100 mL), and Pd(PPh$_3$)$_4$ (0.71 g, 0.61 mmol) and K$_2$CO$_3$ (3.4 g, 24.6 mmol) in H$_2$O (50 mL) were added thereto sequentially. The mixture was refluxed under stirring. Three hours later, washed with brine, and the organic layer was extracted with ethyl acetate. Water was removed over magnesium sulfate, and the residue was filtered under reduced pressure, concentrated to remove the solvent, and then separated by column chromatography to obtain a compound 9c (2.9 g, 75%). MS [M+H]+=315

9-D. Preparation of Compound 9d

The compound 9c (16.7 g, 53.1 mmol) prepared in the step of 9-C was dissolved in anhydrous THF (100 mL) under a nitrogen atmosphere, the solution was cooled to −78° C., and t-butyllithium (46.8 mL, 1.7 M pentane solution) was slowly added thereto, the solution was stirred at the same temperature for 1 hour, and then 2,6-dibromoanthraquinone (6.36 g, 22.0 mmol) was added thereto. The cooling vessel was removed, and the mixture was stirred at normal temperature for 3 hours. To the reaction mixture, an aqueous ammonium chloride solution was added, and the mixture was extracted with methylene chloride. The organic layer was dried over anhydrous magnesium sulfate to remove the solvent. After the resulting mixture was dissolved in a small amount of ethyl ether, petroleum ether was added to the solution, and the mixture was stirred for several hours to obtain a solid compound. The solid compound was filtered, and then dried in vacuo to obtain a compound 9d (17 g, 90%).

9-E. Preparation of Compound 9e

The compound 9d (17 g, 20.5 mmol) prepared in the step of 9-D was dispersed in acetic acid (200 mL) under a nitrogen atmosphere, to which potassium iodide (34 g, 210 mmol) and sodium hypophosphite hydrate (37 g, 420 mmol) were added. The resulting mixture was stirred under boiling for 3 hours. After cooling to normal temperature, the mixture was filtered and washed with water and methanol, and then dried in vacuo to obtain a pale yellow compound 9e (10 g, 64%). MS [M+H]+=804

9-F. Preparation of Compound 43

The compound 9e (10 g, 12.4 mmol) prepared in the step of 9-E and phenyl boronic acid (3.3 g, 27.3 mmol) were dissolved in anhydrous THF (300 mL) under a nitrogen atmosphere, and Pd(PPh$_3$)$_4$ (0.7 g, 0.62 mmol) and an aqueous K$_2$CO$_3$ solution (25 mL, 49.6 mmol) were added thereto sequentially, and then the mixture was refluxed for 5 hours. The organic layer was extracted with ethyl acetate. Water was removed over magnesium sulfate, and the residue was filtered under reduced pressure, concentrated to remove the solvent, purified by column chromatography, and then recrystallized with THF and ethanol to obtain a white solid compound 43 (8 g, 82%). MS [M+H]+798

Example 10

Preparation of Compound 44

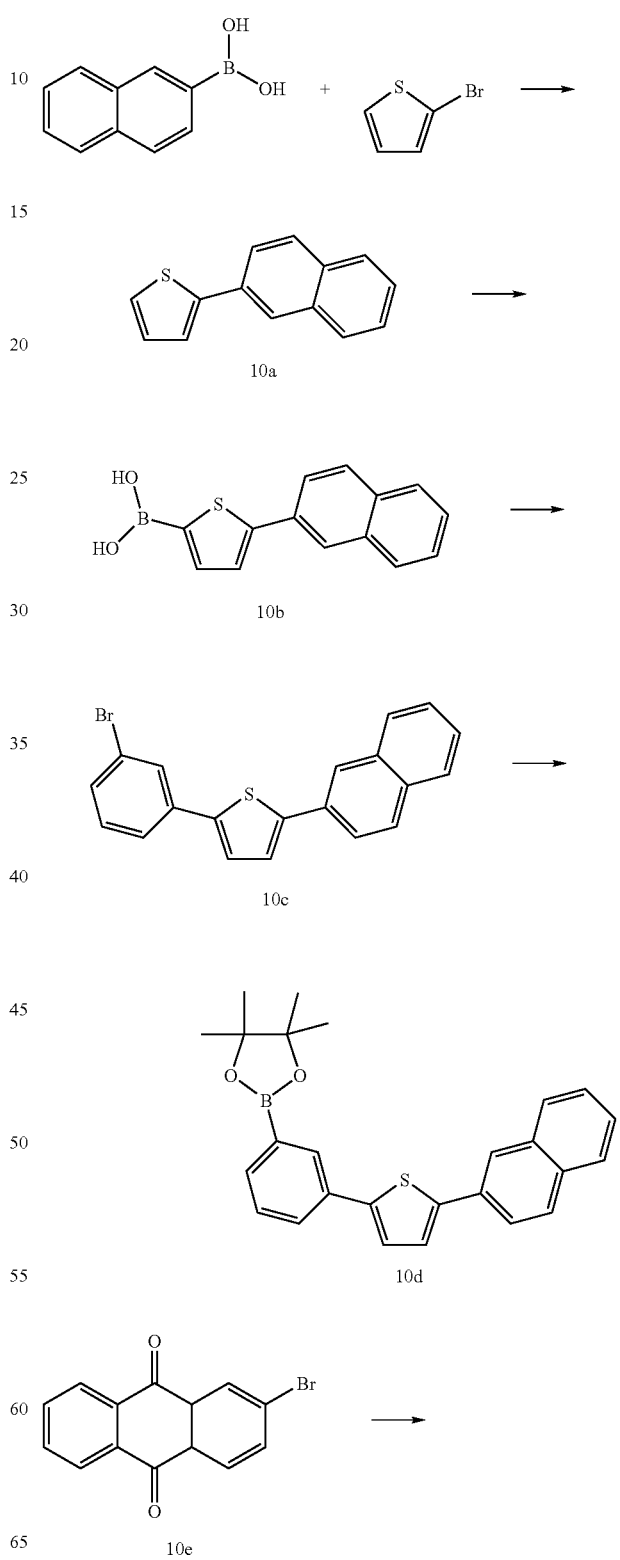

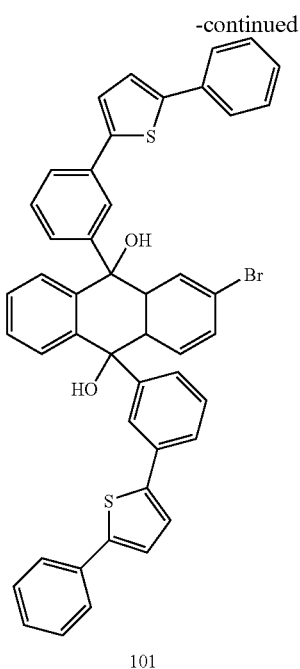 101

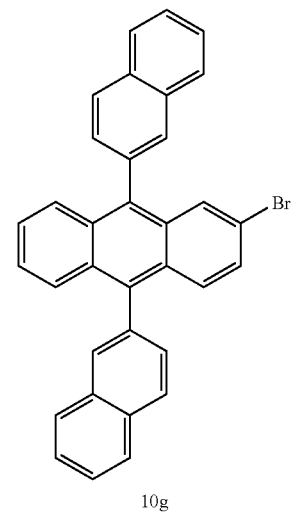 10g

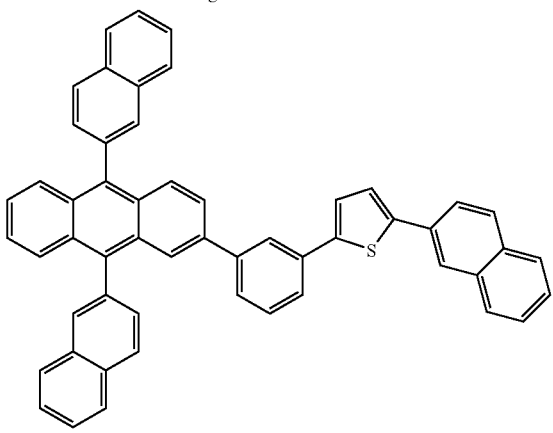 44

10-A. Synthesis of Compound 10a

2-Naphthalene boronic acid (13.4 g, 78.1 mmol) and 2-bromothiophene (11.5 g, 70.3 mmol)) were dissolved in anhydrous THF (300 mL) under a nitrogen atmosphere, and Pd(PPh$_3$)$_4$ (4.06 g, 3.51 mmol) and an aqueous K$_2$CO$_3$ solution (156 mL, 312.4 mmol) were added thereto sequentially, and then the mixture was refluxed for 5 hours. The organic layer was extracted with ethyl acetate. Water was removed over magnesium sulfate, and the residue was filtered under reduced pressure, concentrated to remove the solvent, purified by column chromatography, and then recrystallized with THF and ethanol to obtain a white solid compound 10a (12.6 g, 85%). MS [M+H]+=210

10-B. Synthesis of Compound 10b

The compound 10a (6.6 g, 31.3 mmol) prepared in the step of 10-A was dissolved in anhydrous THF (200 mL), and the solution was cooled to −10° C., and n-butyllithium (15 mL, 37.5 mmol) was slowly added dropwise thereto. After the mixture was stirred for 1 hour, and cooled to −78° C. again, boronic acid trimethylester (10.5 mL, 93.75 mmol) was slowly added thereto, and the mixture was stirred for 12 hours. The mixture was cooled to 0° C., a 2 N aqueous hydrochloric acid solution (16 mL) was added thereto, and the mixture was stirred to obtain a white precipitate. The organic layer was extracted with THF, dried over magnesium sulfate, and then filtered under reduced pressure. This filtrate was concentrated to remove the solvent, dissolved in THF, an excessive amount of an aqueous solution was added thereto, and the organic layer was separated with dimethylchloromethane. To the separated aqueous solution layer, an aqueous hydrochloric acid solution was added, and the resulting precipitate was produced and filtered to obtain a compound 10b (2.7 g, 42%).

10-C. Synthesis of Compound 10c

3-Bromoiodobenzene (3.5 g, 12.3 mmol) and the compound 10b (3.0 g, 12.3 mmol) prepared in the step of 10-B were dissolved in anhydrous THF (100 mL), and Pd(PPh$_3$)$_4$ (0.71 g, 0.61 mmol) and K$_2$CO$_3$ (3.4 g, 24.6 mmol) dissolved in H$_2$O (50 mL) were added thereto sequentially. The mixture was refluxed under stirring. Three hours later, the mixture was washed with brine, and the organic layer was extracted with ethyl acetate. Water was removed over magnesium sulfate, and the residue was filtered under reduced pressure, concentrated to remove the solvent, and separated by column chromatography to obtain a compound 10c (2.9 g, 75%). MS [M+H]+=365

10-D. Synthesis of Compound 10d

The compound 10c (3.6 g, 9.81 mmol) prepared in the step of 10-C, bis(pinacolato)diboron (2.75 g, 10.9 mmol), potassium acetate (2.89 g, 29.4 mmol), and palladium (diphenyl phosphinoferrocene)chloride (0.24 g, 3 mol %) were put into a 250-mL flask under a nitrogen atmosphere. Then, dioxane (50 mL) was added to the mixture, and the mixture was refluxed at 80° C. for 6 hours. The mixture was cooled to room temperature, and distilled water (50 mL) was added thereto, and then extracted with methylen chloride (50 mL×3). Methylene chloride was removed therefrom under reduced pressure to obtain a pale yellow solid. This pale yellow solid was washed with ethanol, and dried to obtain a compound 10d (3.84 g, 95%).

10-E. Synthesis of Compound 10e

Copper bromide (18 g, 80.0 mmol) and t-butyl nitrite (12 mL, 101 mmol) were dispersed in acetonitrile (250 mL) at 65° C., and the mixture was stirred, to which 2-amino anthraquinone (15 g, 67.2 mmol) was then slowly added dropwise over 5 minutes. After completion of gas generation, the reaction solution was cooled to normal temperature, and the reaction solution was added to a 20% aqueous hydrochloric acid solution (1 L), and the mixture was extracted with dichloromethane. The organic layer was dried over anhydrous magnesium sulfate to remove the residual water, and then dried under reduced pressure. The residue was separated by column chromatography to obtain a pale yellow compound 10e (14.5 g, 75%).

10-F. Synthesis of Compound 10f

2-Bromonaphthalene (11.0 g, 53.1 mmol) was dissolved in anhydrous THF (100 mL) under a nitrogen atmosphere, and t-butyllithium (46.8 mL, 1.7 M pentane solution) was slowly added thereto at −78° C., the solution was stirred at the same temperature for 1 hour, and then the compound 10e (6.36 g, 22.0 mmol) prepared in the step of 10-E was added thereto. The cooling vessel was removed, and the mixture was stirred at normal temperature for 3 hours. To the reaction mixture, an aqueous ammonium chloride solution was added, and the mixture was extracted with methylene chloride. The organic layer was dried over anhydrous magnesium sulfate to remove the solvent. The resulting mixture was dissolved in a small amount of ethyl ether, and then petroleum ether was added to the solution, and the mixture was stirred for several hours to obtain a solid compound. The solid compound was filtered, and then dried in vacuo to obtain a compound 10f (11.2 g, 93%).

10-G. Synthesis of Compound 10g

The compound 10f (11.2 g, 20.5 mmol) prepared in the step of 10-F was dispersed in acetic acid (200 mL) under a nitrogen atmosphere, to which potassium iodide (34 g, 210 mmol) and sodium hypophosphite hydrate (37 g, 420 mmol) were added. The resulting mixture was stirred under boiling for 3 hours. After cooling to normal temperature, the mixture was filtered and washed with water and methanol, and then dried in vacuo to obtain a pale yellow compound 10g (7.2 g, 64%). MS [M]=509

10-H. Synthesis of Compound 44

The compound 10g (1.3 g, 2.6 mmol) prepared in the step of 10-G and the compound 10d (1.28 g, 3.1 mmol) prepared in the step 10-D were dissolved in anhydrous THF (70 mL), and Pd(PPh$_3$)$_4$ (0.15 g, 0.13 mmol) and a 2 M aqueous K$_2$CO$_3$ solution (20 mL) were added thereto sequentially, and then the mixture was refluxed under stirring for 5 hours. The organic layer was extracted with ethyl acetate. Water was removed over magnesium sulfate, and the residue was filtered under reduced pressure, concentrated, and then recrystallized from THF and ethanol to obtain a compound 44 (1.5 g, 83%). MS [M+H]=714

Example 11

Preparation of Compound 46

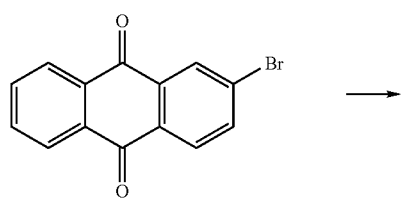

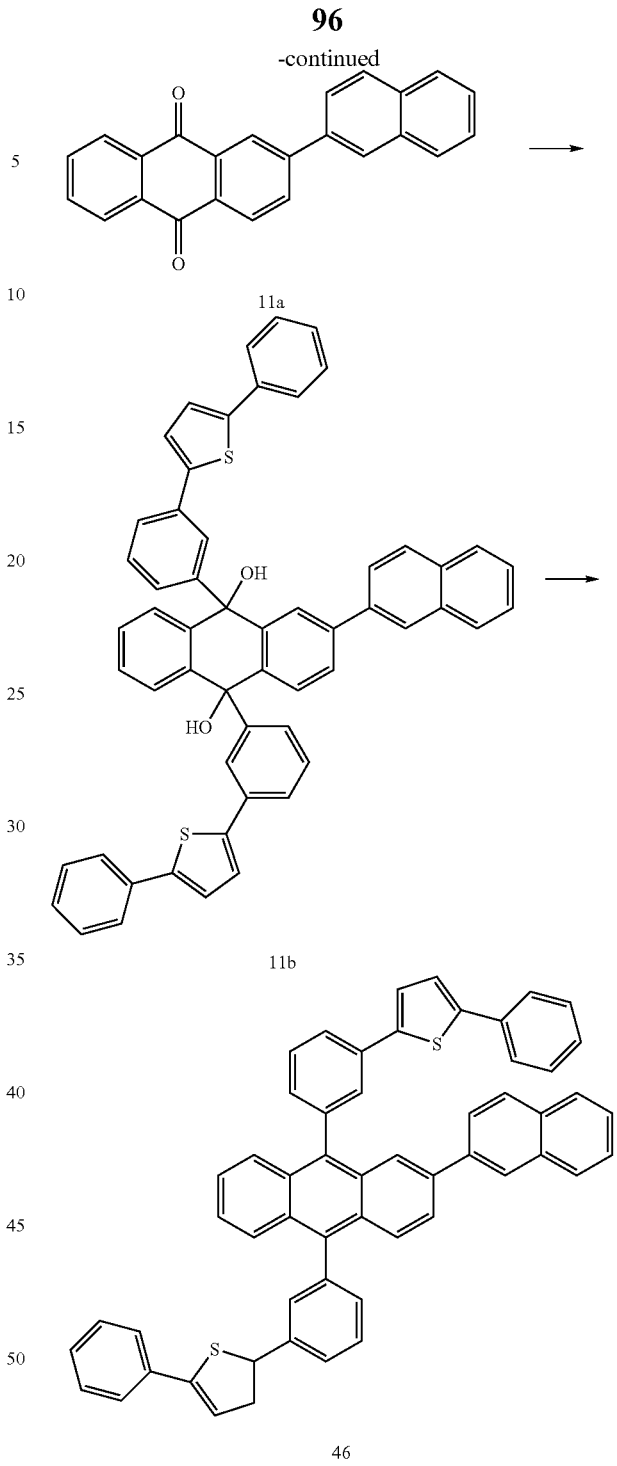

11-A. Synthesis of Compound 11a

The compound 10e (3.6 g, 12.3 mmol) prepared in the step of 10-E and 2-naphthalene boronic acid (2.3 g, 13.5 mmol) were dissolved in anhydrous THF (100 mL) under a nitrogen atmosphere, and Pd(PPh$_3$)$_4$ (0.71 g, 0.61 mmol), and K$_2$CO$_3$ (3.4 g, 24.6 mmol) dissolved in H$_2$O (50 mL) were added thereto sequentially, and then the mixture was refluxed under stirring. Three hours later, the mixture was washed with brine, and the organic layer was extracted with ethyl acetate. Water was removed over magnesium sulfate, and the residue was filtered under reduced pressure, concentrated to remove the solvent, and separated by column chromatography to obtain a compound 11a (3.2 g, 78%). MS [M+H]+=334

11-B. Synthesis of Compound 11b

The compound 9c (6.46 g, 17.7 mmol) prepared in the step of 9-C was dissolved in anhydrous THF (100 mL) under a nitrogen atmosphere, and t-butyllithium (15.6 mL, 1.7 M pentane solution) was slowly added thereto at −78° C., the solution was stirred at the same temperature for 1 hour, and then the compound 11a (2.44 g, 7.3 mmol) prepared in the step of 11-A was added thereto. The cooling vessel was removed, and the mixture was stirred at normal temperature for 3 hours. To the reaction mixture, an aqueous ammonium chloride solution was added, and the mixture was extracted with methylene chloride. The organic layer was dried over anhydrous magnesium sulfate to remove the solvent. The resulting mixture was dissolved in a small amount of ethyl ether, and petroleum ether was added to the solution, and then the mixture was stirred for several hours to obtain a solid compound. The solid compound was filtered, and then dried in vacuo to obtain a compound 11b (5.1 g, 88%).

11-C. Synthesis of Compound 46

The compound 11b (4.15 g, 5.13 mmol) prepared in the step of 11-B was dispersed in acetic acid (50 mL) under a nitrogen atmosphere, to which potassium iodide (8.5 g, 52.5 mmol) and sodium hypophosphite hydrate (9.3 g, 105 mmol) were added. The resulting mixture was stirred under boiling for 3 hours. After cooling to normal temperature, the mixture was filtered and washed with water and methanol, and then dried in vacuo to obtain a pale yellow compound 46 (2.4 g, 60%). MS [M+H]+=788

Example 12

Preparation of Compound 55

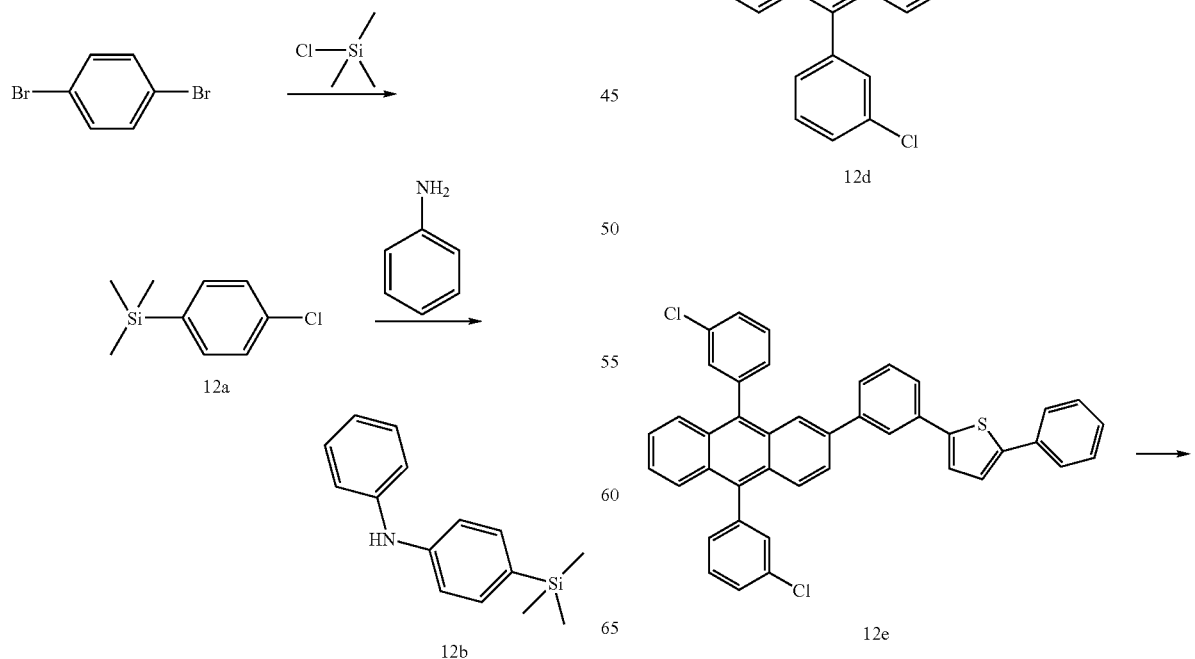

-continued

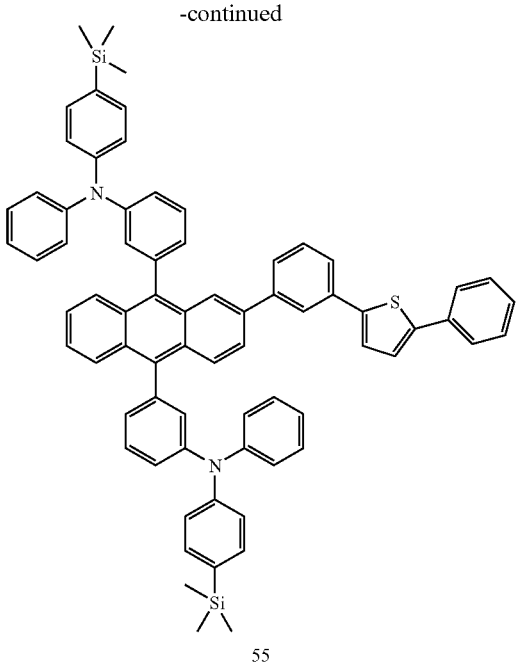

55

12-A. Synthesis of Compound 12a

Dibromobenzene (20 g, 84.78 mmol) was dissolved in anhydrous tetrahydrofuran (THF, 200 mL) at room temperature under a nitrogen atmosphere. The solution was cooled to −78° C. N-butyllithium (34 mL, 2.5 M pentane solution) was added slowly to the solution at −78° C., and the temperature of the mixture was slowly raised to 0° C. for about 1 hour. To the mixture, chlorotrimethylsilane (13 ml, 101.74 mmol) was added, and the temperature of the mixture was raised to normal temperature over 1 hour. After completion of the reaction, the mixture was extracted with ethyl acetate, dried over magnesium sulfate, and distilled off under reduced pressure to obtain a compound 12a (18 g, 93%). MS (M+) 229

12-B. Synthesis of Compound 12b

The compound 12a (15 g, 65.45 mmol) prepared in the step of 12-A, aniline (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (200 mL), and the mixture was refluxed for about 3 hours. After completion of the reaction, the mixture was cooled to normal temperature, and the reaction mixture was added to a mixed solution of THF and H$_2$O. The organic layer was subject to phase separation, dried over MgSO$_4$, concentrated, and then separated by column chromatography to obtain a compound 12b (15 g, 86%). MS [M]=143

12-C. Synthesis of Compound 12c

1-Bromo-3-chlorobenzene (10 g, 53.1 mmol) was dissolved in anhydrous THF (100 mL) under a nitrogen atmosphere. t-butyllithium (46.8 mL, 1.7 M pentane solution) was added slowly to the solution at −78° C., and the solution was stirred at the same temperature for 1 hour, and then the compound 10e (6.36 g, 22.0 mmol) prepared in the step of 10-E was added thereto. The cooling vessel was removed, and the mixture was stirred at normal temperature for 3 hours. To the reaction mixture, an aqueous ammonium chloride solution was added, and the mixture was extracted with methylene chloride. The organic layer was dried over anhydrous magnesium sulfate to remove the solvent. The resulting mixture was dissolved in a small amount of ethyl ether, and petroleum ether was added to the solution, and then the mixture was stirred for several hours to obtain a solid compound. The solid compound was filtered, and then dried in vacuo to obtain a compound 12c (10 g, 90%).

12-D. Synthesis of Compound 12d

The compound 12c (10 g, 20.5 mmol) prepared in the step of 12-C was dispersed in acetic acid (200 mL) under a nitrogen atmosphere, to which potassium iodide (34 g, 210 mmol) and sodium hypophosphite hydrate (37 g, 420 mmol) were added. The resulting mixture was stirred under boiling for 3 hours. After cooling to normal temperature, the mixture was filtered and washed with water and methanol, and then dried in vacuo to obtain a pale yellow compound 12d (7.2 g, 64%). MS [M]=477

12-E. Synthesis of Compound 12e

The compound 12d (1.24 g, 2.6 mmol) prepared in the step of 12-D and the compound 9c (1.28 g, 3.1 mmol) prepared in the step of 9-C were dissolved in anhydrous THF (70 mL) under a nitrogen atmosphere, and Pd(PPh$_3$)$_4$ (0.15 g, 0.13 mmol) and a 2 M aqueous K$_2$CO$_3$ solution (20 mL) were added thereto sequentially, and then the mixture was refluxed under stirring for 5 hours. The organic layer of the reaction solution was extracted with ethyl acetate. Water was removed over magnesium sulfate, and the residue was filtered under reduced pressure, concentrated, and then recrystallized with THF and ethanol to obtain a compound 12e (1.4 g, 85%). MS [M+H]+=632

12-F. Synthesis of Compound 55

The compound 12b (5.4 g, 8.5 mmol) prepared in the step of 12-B, the compound 12e (4.9 g, 20.4 mmol) prepared in the step of 12-E, Pd(dba)$_2$ (0.097 g, 0.17 mmol), P(t-Bu)$_3$ (0.05 g, 0.255 mmol) and sodium t-butoxide (2.45 g, 25.5 mmol) were added to toluene (100 mL), and the mixture was refluxed for about 5 hours. After completion of the reaction, the mixture was cooled to normal temperature, and the reaction mixture was added to a mixed solution of THF and H$_2$O. The organic layer was subject to phase separation, dried over MgSO$_4$, concentrated, and then separated by column chromatography to obtain a compound 55 (7.7 g, 87%). MS [M+H]+=1042

Example 13

Preparation of Compound 67

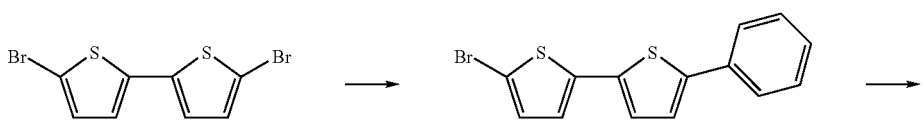

13a

101

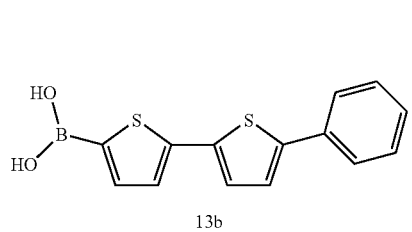

13b

-continued

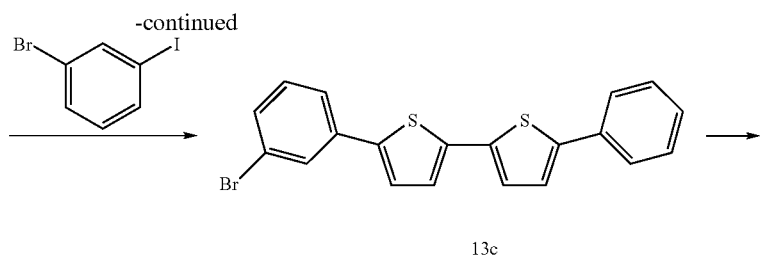

13c

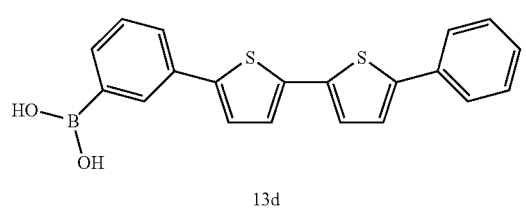

13d

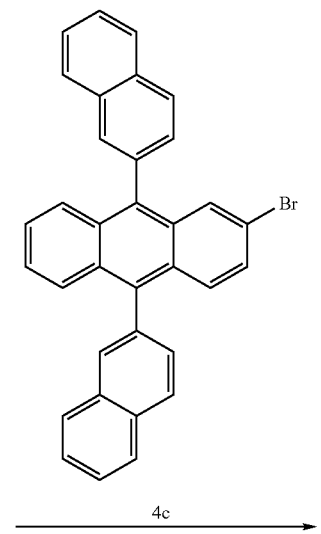

4c

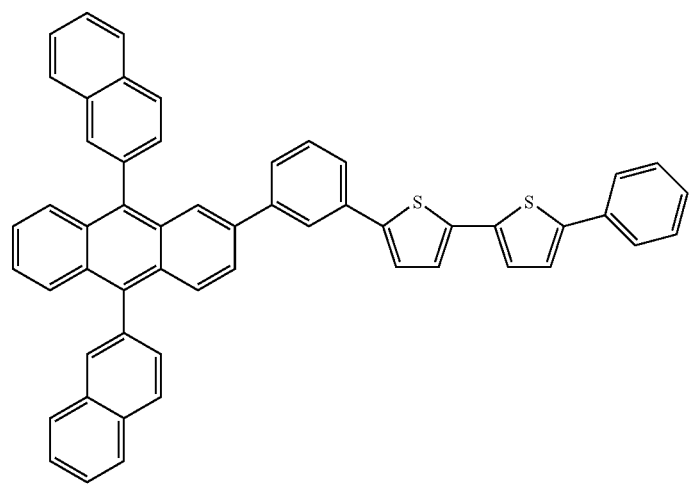

67

13-A. Synthesis of Compound 13a 5,5'-Dibromo-2,2'-bithiophene (15.43 mmol, 5.0 g), phenyl boronic acid (16.97 mmol, 2.07 g), 2 M potassium carbonate (15 ml), tetrakis(triphenyl phosphine)palladium(0) (0.46 mmol, 0.5 g) and THF (30 ml) were put into a 100-ml round flask, and the mixture was refluxed under stirring for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 13a (2.8 g, 56.5%).

13-B. Synthesis of Compound 13b

The compound 13a (6.23 mmol, 2.0 g) prepared in the step of 13-A was dissolved in anhydrous THF (50 ml), and a 1.7 M solution of t-butyllithium (9.35 mmol, 6.23 ml) was very slowly added thereto at −78° C. One hour later, trimethyl borate (12.46 mmol, 1.4 ml) was added thereto. 30 minutes later, dry ice was removed, and the mixture was reacted at normal temperature for 3 hours. After completion of the reaction, the resultant was quenched with HCl, ethyl ether was added thereto, and the mixture was stirred for about 1 hour. Thus, a solid was generated, and this solid was filtered while washing with pet-ether, and dried in a vacuum oven to obtain a compound 13b (1.08 g, 60.6%).

13-C. Synthesis of Compound 13c

1-Bromo-3-iodobenzene (3.77 mmol, 1.06 g), the compound 13b (3.77 mmol, 1.08 g) prepared in Example 13-B, 2 M potassium carbonate (15 ml), tetrakis(triphenyl phosphine)palladium(0) (0.11 mmol, 0.13 g), and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 13c (1.2 g, 80%).

13-D. Synthesis of Compound 13d

The compound 13c (3.01 mmol, 1.2 g) prepared in the step of 13-C was dissolved in 50 ml of anhydrous THF, and a 1.7 M solution of t-butyllithium (4.5 mmol, 2.65 ml) was very slowly added thereto at −78° C. One hour later, trimethyl borate (6.02 mmol, 7.3 ml) was added thereto. 30 minutes later, dry ice was removed, and the mixture was reacted at normal temperature for 3 hours. After completion of the reaction, the resultant was quenched with HCl, ethyl ether was added thereto, and the mixture was stirred for about 1 hour. Thus, a solid was generated, and this solid was filtered while washing with pet-ether, and dried in a vacuum oven to obtain a compound 13d (0.76 g, 75%).

13-E. Synthesis of Compound 67

The compound 4c (2.1 mmol, 1.07 g) prepared in the step of 4-C in Example 4, the compound 13d (2.1 mmol, 0.76 g) synthesized in Example 13-d, 2 M potassium carbonate (15 ml), tetrakis(triphenyl phosphine)palladium(0) (0.06 mmol, 0.07 g) and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 67 (1.11 g, 71%).

Example 14

Synthesis of Compound 68

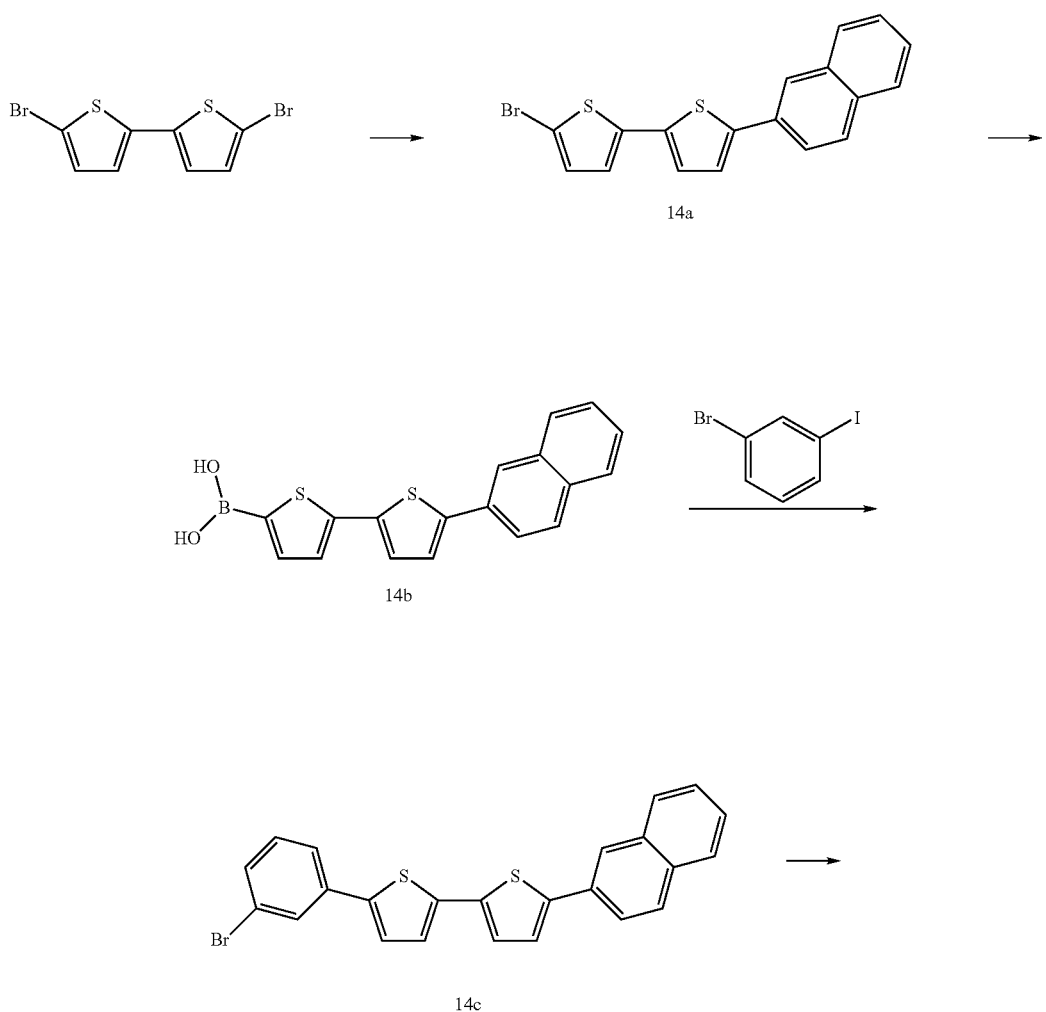

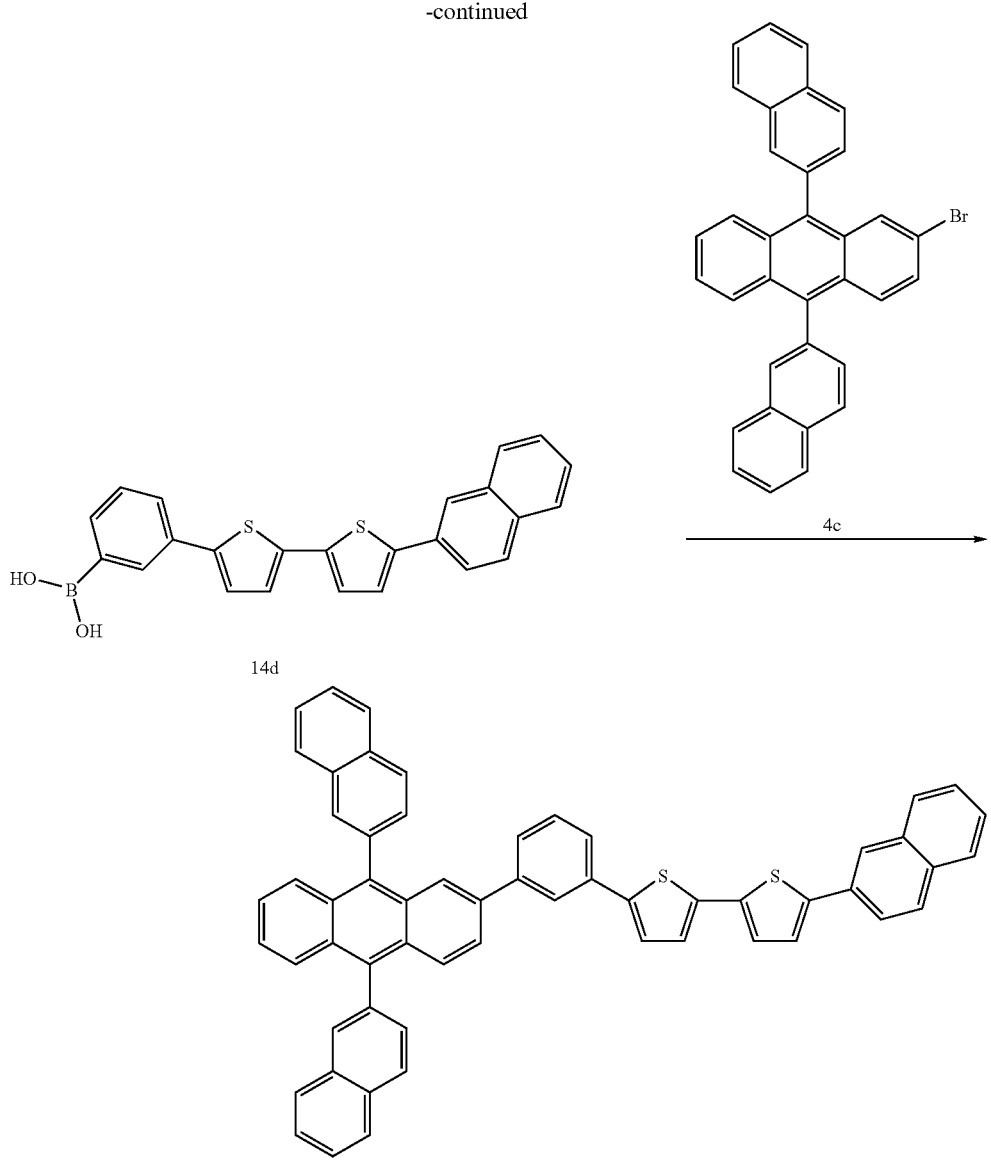

68

14-A. Synthesis of Compound 14a 5,5'-Dibromo-2,2'-bithiophene (15.43 mmol, 5.0 g), 2-naphthalene boronic acid (16.97 mmol, 2.92 g), 2 M potassium carbonate (15 ml), tetrakis(triphenyl phosphine)palladium(0) (0.46 mmol, 0.5 g) and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 14a (4.3 g, 75%).

14-B. Synthesis of Compound 14b

The compound 14a (6.23 mmol, 2.3 g) prepared in the step of 14-A was dissolved in anhydrous THF (50 ml), and a 1.7 M solution of t-butyllithium (9.35 mmol, 6.23 ml) was very slowly added thereto at −78° C. One hour later, trimethyl borate (12.46 mmol, 1.4 ml) was added thereto. 30 minutes later, dry ice was removed, and the mixture was reacted at normal temperature for 3 hours. After completion of the reaction, the resultant was quenched with HCl, ethyl ether was added thereto, and the mixture was stirred for about 1 hour. Thus, a solid was generated, and this solid was filtered while washing with pet-ether, and dried in a vacuum oven to obtain a compound 14b (1.42 g, 68%).

14-C. Synthesis of Compound 14c

1-Bromo-3-iodobenzene (3.77 mmol, 1.06 g), the compound 14b (3.77 mmol, 1.27 g) synthesize in Example 14-B, 2 M potassium carbonate (15 ml), tetrakis(triphenyl phosphine)palladium(0) (0.11 mmol, 0.13 g), and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 14c (1.43 g, 85%).

14-D. Synthesis of Compound 14d

The compound 14c (3.01 mmol, 1.35 g) prepared in the step of 14-C was dissolved in anhydrous THF (50 ml), and a 1.7 M solution of t-butyllithium (4.5 mmol, 2.65 ml) was very slowly added thereto at −78° C. One hour later, trimethyl borate (6.02 mmol, 7.3 ml) was added thereto. 30 minutes later, dry ice was removed, and the mixture was reacted at normal temperature for 3 hours. After completion of the reaction, the resultant was quenched with HCl, ethyl ether was added thereto, and the mixture was stirred for about 1 hour. Thus, a solid was generated, and this solid was filtered while washing with pet-ether, and dried in a vacuum oven to obtain a compound 14d (0.98 g, 79%).

14-E. Synthesis of Compound 68

The compound 4c (2.1 mmol, 1.07 g) prepared in the step of 4-C in Example 4, the compound 14d (2.1 mmol, 0.86 g), synthesized in Example 14-d, 2 M potassium carbonate (15 ml), tetrakis(triphenyl phosphine)palladium(0) (0.06 mmol, 0.07 g) and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven. The yield of the resulting powder was 1.26 g (1.58 mmol, 75%).

Example 15

Preparation of Compound 69

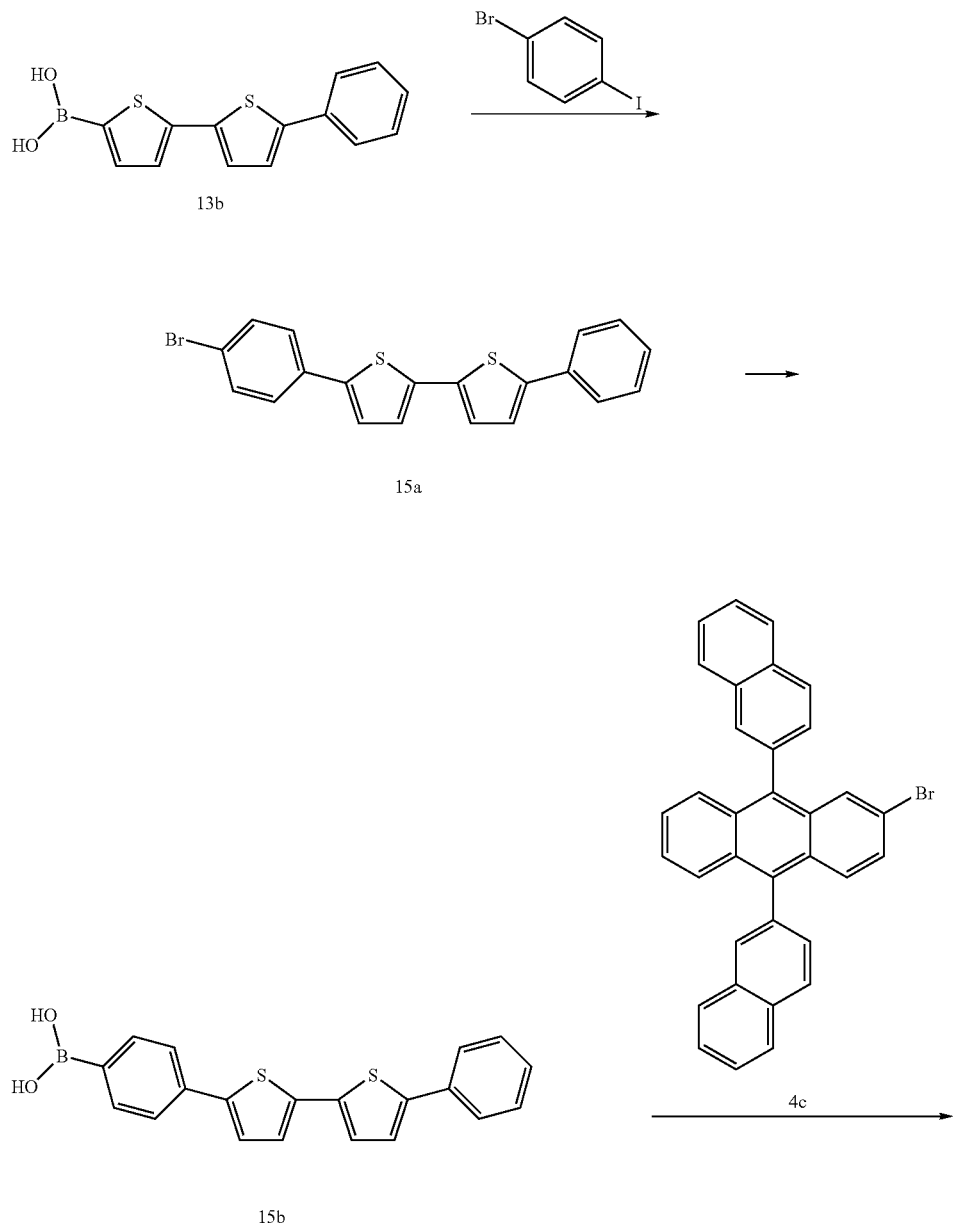

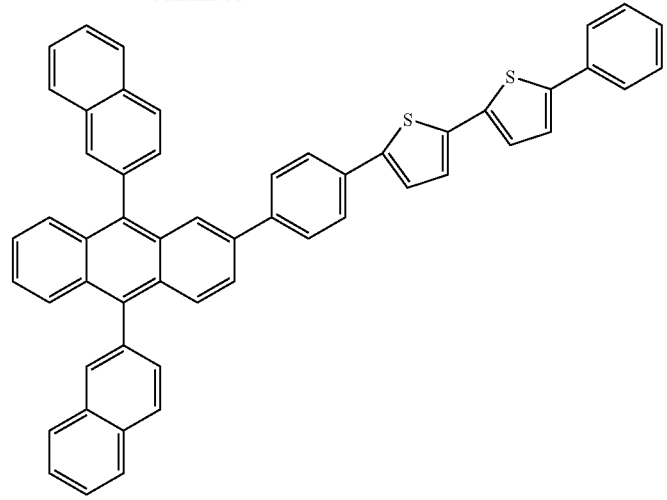

69

15-A. Synthesis of Compound 15a

1-Bromo-4-iodobenzene (3.77 mmol, 1.06 g), the compound 13b (3.77 mmol, 1.08 g) synthesized in the step of 13-b in Example 13, 2 M potassium carbonate (15 ml), tetrakis(triphenyl phosphine)palladium(0) (0.11 mmol, 0.13 g) and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 15a (1.23 g, 82%).

15-B. Synthesis of Compound 15b

The compound 15a (3.01 mmol, 1.2 g) prepared in Example 15-A was dissolved in anhydrous THF (50 ml), and a 1.7 M solution of t-butyllithium (4.5 mmol, 2.65 ml) was very slowly added thereto at −78° C. One hour later, trimethyl borate (6.02 mmol, 7.3 ml) was added thereto. 30 minutes later, dry ice was removed, and the mixture was reacted at normal temperature for 3 hours. After completion of the reaction, the resultant was quenched with HCl, ethyl ether was added thereto, and the mixture was stirred for about 1 hour. Thus, a solid was generated, and this solid was filtered while washing with pet-ether, and dried in a vacuum oven to obtain a compound 15b (0.87 g, 80%).

15-C. Synthesis of Compound 69

The compound 4c (2.1 mmol, 1.07 g) synthesize in the step of 4-C in Example 4, the compound 15b (2.1 mmol, 0.76 g) synthesize in Example 15-B, 2M potassium carbonate (15 ml), tetrakis(triphenyl phosphine)palladium(0) (0.06 mmol, 0.07 g), and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 69 (1.23 g, 79%).

Example 16

Synthesis of Compound 70

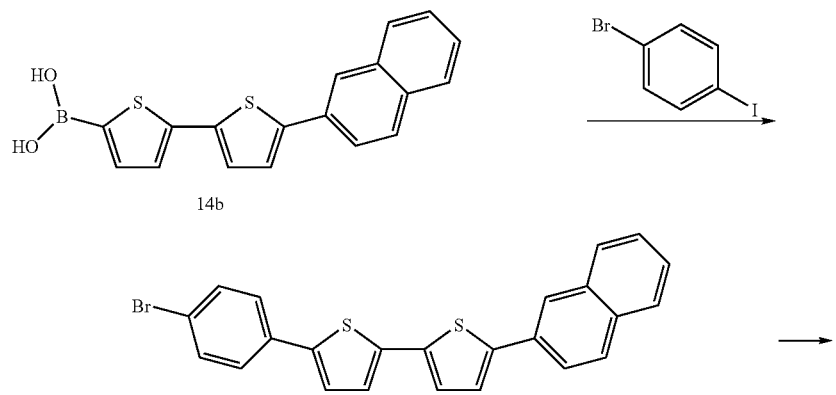

-continued

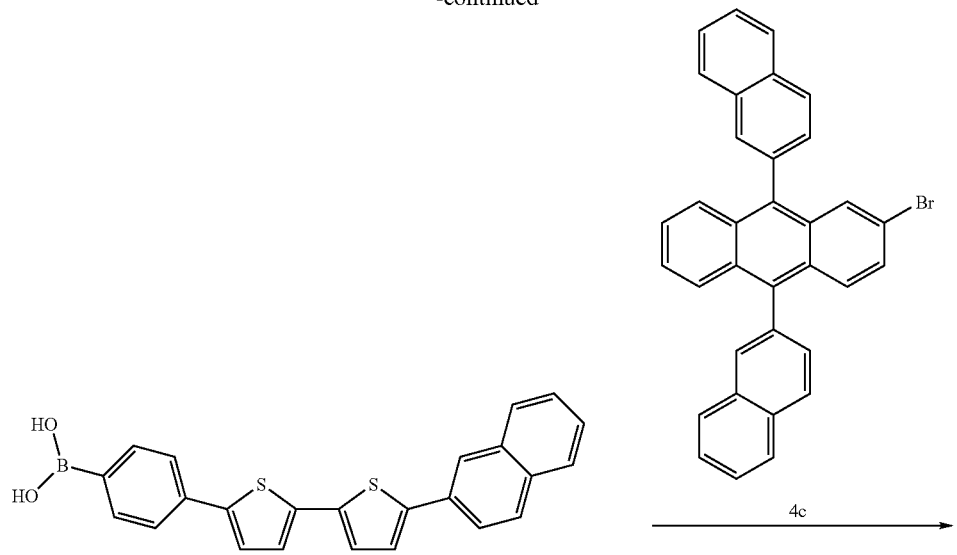

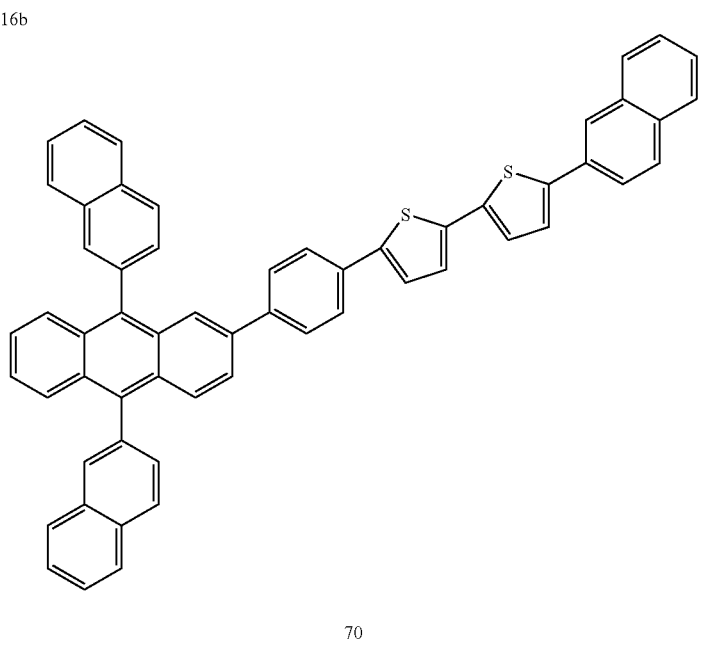

16-A. Synthesis of Compound 16a

1-Bromo-4-iodobenzene (3.77 mmol, 1.06 g), the compound 14b (3.77 mmol, 1.27 g) synthesized in the step of 14-b in Example 14, 2 M potassium carbonate (15 ml), tetrakis(triphenyl phosphine)palladium(0) (0.11 mmol, 0.13 g) and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 16a (1.47 g, 87%).

16-B. Synthesis of Compound 16b

The compound 16a (3.01 mmol, 1.35 g) prepared in Example 16-A was dissolved in anhydrous THF (50 ml), and a 1.7 M solution of t-butyllithium (4.5 mmol, 2.65 ml) was very slowly added thereto at −78° C. One hour later, trimethyl borate (6.02 mmol, 7.3 ml) was added thereto. 30 minutes later, dry ice was removed, and the mixture was reacted at normal temperature for 3 hours. After completion of the reaction, the resultant was quenched with HCl, ethyl ether was added thereto, and the mixture was stirred for about 1 hour. Thus, a solid was generated, and this solid was filtered while washing with pet-ether, and dried in a vacuum oven to obtain a compound 16b (1.01 g, 82%).

16-C. Synthesis of Compound 70

The compound 4c (2.1 mmol, 1.07 g) prepared in the step of 4-C in Example 4, the compound 16b (2.1 mmol, 0.86 g) peppered in Example 16-b, 2 M potassium carbonate (15 ml), tetrakis(triphenyl phosphine)palladium(0) (0.06 mmol, 0.07 g), and THF (30 ml) were put into a 100-ml round flask, and the mixture was refluxed for 24 hours. After completion of the reaction, the mixture was cooled to normal temperature, extracted with chloroform, and washed with water several times. The mixture was dried over magnesium sulfate, and evaporated. The crude product was purified by column chromatography (n-hexane), evaporated, and then dried in a vacuum oven to obtain a compound 70 (1.42 g, 85%).

Experimental Example 1 to 4

A glass substrate (Corning 7059 glass) on which a thin film of ITO (indium tin oxide) was coated to a thickness of 1000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using isopropyl alcohol, acetone and methanol in this order as the solvents, followed by drying.

On the ITO electrode, 3,6-bis-2-naphthylphenylamino-N-[4-(2-naphthylphenyl) aminophenyl]carbazole (800 Å), 4,4'-bis[N-(1-naphthyl)-N-phenyl amino]biphenyl (NPB) (300 œ, host material (300 Å) as described in the following Table 2), and 9,10-bis-2-naphthyl-2-[4-(N-phenylbenzoimidazoyl)phenyl]anthracene (300 Å) were sequentially coated by thermal vacuum deposition to sequentially form a hole injecting layer, a hole transporting layer, a light emitting layer, and an electron transporting layer. In the light emitting layer, as the dopant material, a styrylamine compound (D1) and a compound (D2) were used.

Lithium fluoride (LiF) and aluminum were sequentially deposited on the electron transporting layer to thicknesses of 12 Å and 2000 Å respectively, to form a cathode, thereby obtaining an organic light emitting device.

In the above process, the deposition rate of the organic material was maintained at 0.4 to 0.7 Å/sec and the deposition rate of lithium fluoride was maintained at 0.3 ÅA/sec and the deposition rate of aluminum was maintained at 2 Å/sec, respectively. The degree of vacuum upon deposition was maintained at $2 \times 10^{-7}$ to $5 \times 10^{-8}$ torr.

TABLE 2

| Experimental Example No. | Host material | Dopant Material | Doping Concentration (wt %) |
|---|---|---|---|
| 1 | Compound 5 | None | 0 |
| 2 | Compound 5 | D1 | 8 |

TABLE 2-continued

| Experimental Example No. | Host material | Dopant Material | Doping Concentration (wt %) |
|---|---|---|---|
| 3 | Compound 7 | D1 | 8 |
| 4 | Compound 14 | D2 | 4 |

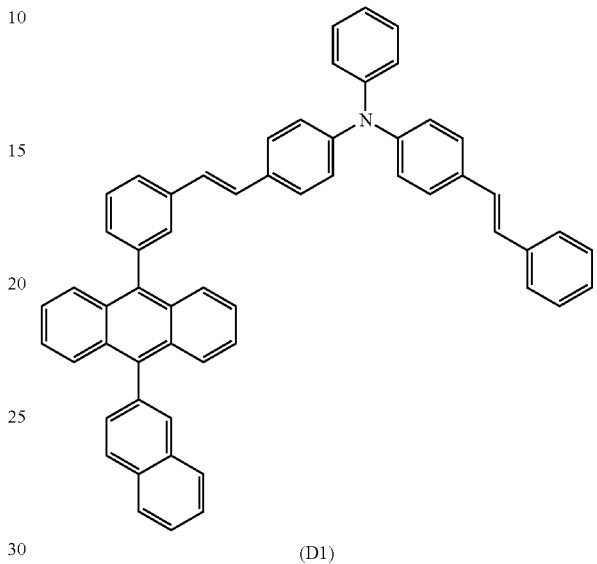

(D1)

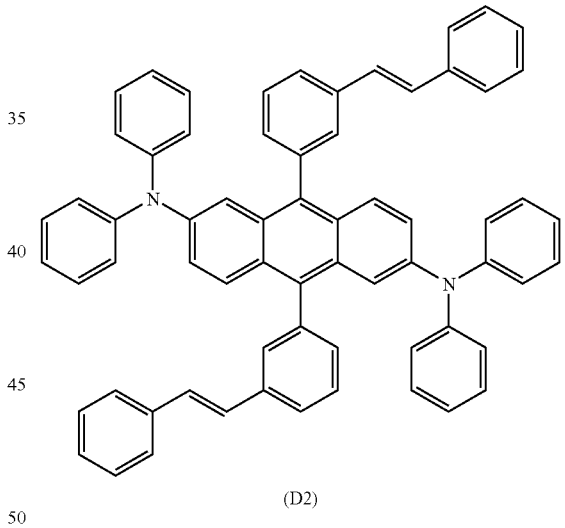

(D2)

In Experimental Example 1, when a forward electric field of 6 V was applied to the device as prepared above, 1700 nit of blue light emission was observed. When the current was applied to the devices prepared in Experimental Examples 2 to 4, the results as shown in the following Table 3 were obtained.

TABLE 3

| Experimental Example | Host material | Dopant material | Doping concentration(wt %) | Voltage (V) | Current efficiency (cd/A) | Luminous efficiency (lm/W) | Color coordinate (x, y) |
|---|---|---|---|---|---|---|---|
| 2 | Compound 5 | D1 | 8 | 8.2 | 3.4 | 1.4 | (0.148, 0.133) |
| 3 | Compound 7 | D1 | 8 | 7.9 | 4.0 | 1.5 | (0.147, 0.120) |
| 4 | Compound 14 | D2 | 4 | 8.0 | 19.4 | 7.7 | (0.321, 0.631) |

The invention claimed is:
1. A compound represented by the following formula 1:

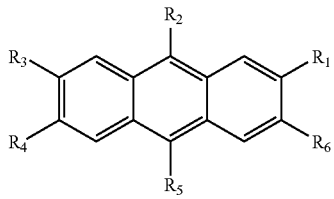

[Formula 1]

wherein $R_1$ to $R_6$ may be identical to or different from each other, and at least one thereof is represented by the following formula 2:

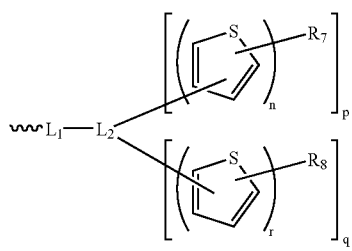

[Formula 2]

wherein n and p are each integers of 1 to 10, and q and r are each integers of 0 to 10, $L_1$ is a direct bond, a phenyl, a naphthyal, or a substituted or unsubstituted $C_5$ to $C_{20}$ heterocyclic group, $L_2$ is a $C_5$ to $C_{20}$ aryl group, and $R_1$ to $R_6$, which are not represented by the formula 2, in the formula 1, and $R_7$ and $R_8$ in the formula 2 are each independently the identical or different substituents, and each selected from the group consisting of hydrogen; halogen; hydroxyl; mercapto; cyano; nitro; carbonyl; carboxyl; formyl; substituted or unsubstituted $C_1$-$C_{20}$ alkyl; substituted or unsubstituted $C_2$-$C_{10}$ alkenyl; substituted or unsubstituted $C_2$-$C_7$ alkynyl; substituted or unsubstituted phenyl; substituted or unsubstituted naphthyl; substituted or unsubstituted biphenyl; substituted or unsubstituted terphenyl; substituted or unsubstituted double spiro; substituted or unsubstituted tetracenyl; substituted or unsubstituted pyrenyl; substituted or unsubstituted perylenyl; substituted or unsubstituted heteroaryl; substituted or unsubstituted $C_3$-$C_7$ cycloalkyl in which a carbon atom in the ring may be substituted by an oxygen, nitrogen, or sulfur atom; $C_4$-$C_7$ cycloalkenyl in which a carbon atom in the ring may be substituted by an oxygen, nitrogen, or sulfur atom; substituted or unsubstituted $C_1$-$C_{20}$ alkoxy; substituted or unsubstituted $C_2$-$C_{10}$ alkenyloxy; substituted or unsubstituted $C_2$-$C_7$ alkynyloxy; substituted or unsubstituted aryloxy; substituted or unsubstituted $C_1$-$C_{20}$ alkylamine; substituted or unsubstituted $C_2$-$C_{10}$ alkenylamine; substituted or unsubstituted $C_2$-$C_7$ alkynylamine; substituted or unsubstituted arylamine; substituted or unsubstituted alkylarylamine; substituted or unsubstituted $C_1$-$C_{20}$ alkylsilyl; substituted or unsubstituted $C_2$-$C_{10}$ alkenylsilyl; substituted or unsubstituted $C_2$-$C_7$ alkynylsilyl; substituted or unsubstituted arylsilyl; substituted or unsubstituted alkylarylsilyl; substituted or unsubstituted $C_1$-$C_{20}$ alkylboranyl; substituted or unsubstituted $C_2$-$C_{10}$ alkenylboranyl; substituted or unsubstituted $C_2$-$C_7$ alkynylboranyl; substituted or unsubstituted arylboranyl; substituted or unsubstituted alkylarylboranyl; substituted or unsubstituted $C_1$-$C_{20}$ alkylthio; substituted or unsubstituted $C_2$-$C_{10}$ alkenylthio; substituted or unsubstituted $C_2$-$C_7$ alkynylthio; and substituted or unsubstituted arylthio groups.

2. The compound according to claim 1, wherein $R_1$ to $R_6$, which are not represented by the formula 2, in the formula 1, and $R_7$ and $R_8$ in the formula 2 are each independently the identical or different substituents, and each can be selected from the group consisting of hydrogen, cyano, nitro, substituted or unsubstituted $C_1$-$C_{20}$ alkyl, substituted or unsubstituted $C_2$-$C_{10}$ alkenyl, substituted or unsubstituted $C_3$-$C_7$ cycloalkyl, substituted or unsubstituted $C_4$-$C_7$ cycloalkenyl, substituted or unsubstituted heteroaryl, substituted or unsubstituted $C_1$-$C_{20}$ alkoxy, substituted or unsubstituted aryloxy, substituted or unsubstituted $C_1$-$C_{20}$ alkylamine, substituted or unsubstituted arylamine, substituted or unsubstituted alkylarylamine, substituted or unsubstituted $C_1$-$C_{20}$ alkylsilyl; substituted or unsubstituted $C_1$-$C_{20}$ alkylboranyl, substituted or unsubstituted arylboranyl, substituted or unsubstituted alkylarylboranyl, substituted or unsubstituted $C_1$-$C_{20}$ alkylthio, and substituted or unsubstituted arylthio groups.

3. The compound according to claim 1, wherein $R_1$ to $R_6$, which are not represented by the formula 2, in the formula 1, and $R_7$ and $R_8$ in the formula 2 are each independently mono- or poly-substituted with the identical or different substituents selected from the group consisting of:

halogen, hydroxyl, mercapto, cyano, nitro, amino, carbonyl, carboxyl, formyl, $C_1$-$C_{20}$ alkyl, $C_2$-$C_{10}$ alkenyl, $C_2$-$C_7$ alkynyl, heteroaryl, $C_3$-$C_7$ cycloalkyl, a saturated or unsaturated 3- to 7-membered heterocyclic ring, acryl, $C_1$-$C_{20}$ alkoxy, $C_2$-$C_{10}$ alkenyloxy, $C_2$-$C_7$ alkynyloxy, $C_1$-$C_{20}$ alkylamine, $C_2$-$C_{10}$ alkenylamine, $C_2$-$C_7$ alkynylamine, arylamine, alkylarylamine, $C_1$-$C_{20}$ alkylsilyl, $C_2$-$C_{10}$ alkenylsilyl, $C_2$-$C_7$ alkynylsilyl, alkoxysilyl, arylsilyl, alkylarylsilyl, $C_1$-$C_{20}$ alkylboranyl, $C_2$-$C_{10}$ alkenylboranyl, $C_2$-$C_7$ alkynylboranyl, arylboranyl, alkylarylboranyl, $C_1$-$C_{20}$ alkylthio, $C_2$-$C_{10}$ alkenylthio, $C_2$-$C_7$ alkynylthio, and arylthio groups.

4. The compound according to claim 1, wherein $R_1$ to $R_6$, which are not represented by the formula 2, in the formula 1, and $R_7$ and $R_8$ in the formula 2 are each independently mono- or poly-substituted with the identical or different substituents selected from the group consisting of:

cyano, nitro, formyl, methyl, ethyl, propyl, phenyl, naphthyl, biphenyl, imidazolyl, thiazolyl, oxazolyl, thiophenyl, pyridyl, pyrimidyl, pyrrolyl, cyclobutenyl, cyclopentenyl, methoxy, ethoxy, propoxy, phenoxy, napththoxy, methylamine, ethylamine, propylamine, phenylamine, naphthylamine, methylphenylamine, ethylphenylamine, ethylnaphthylamine, dimethylboranyl, diethylboranyl, dipropylboranyl, diphenylboranyl, dinaphthylboranyl, phenyl naphthylboranyl, phenyl methylboranyl, naphthylmethylboranyl, naphthylethylboranyl, trimethylsilyl, triethylsilyl, tripropylsilyl, triphenyl silyl, trinaphthylsilyl, dimethylphenyl silyl, diethylphenyl silyl, diphenyl methylsilyl, methylthio, ethylthio, propylthio, butylthio, phenylthio and naphthylthio groups.

5. The compound according to claim 1, wherein the substituted or unsubstituted $C_3$-$C_7$ cycloalkyl in which a carbon atom in the ring may be substituted by an oxygen, nitrogen, or sulfur atom, or the $C_4$-$C_7$ cycloalkenyl in which a carbon atom in the ring may be substituted by an oxygen, nitrogen, or sulfur atom, is a 5- or 6-membered substituted or unsubstituted, saturated and unsaturated ring.

6. The compound according to claim 1, wherein $R_1$ to $R_6$, which are not represented by the formula 2, in the formula 1, and $R_7$ and $R_8$ in the formula 2 are each independently the identical or different substituent, and each can be selected from the group consisting of methyl, ethyl, propyl, butyl, isopropyl, n-butyl, t-butyl, isobutyl, n-pentyl, neo-pentyl, n-hexyl, ethenyl, propenyl, butenyl, pentenyl, hexenyl, 2-methyl-ethenyl, 2-methyl-propenyl, 2-methyl-butenyl, 2-methyl-pentenyl, 2-methyl-hexenyl, imidazolyl, thiazolyl, oxazolyl, thiophenyl, pyridyl, pyrimidyl, pyrrolyl, 2-methylimidazolyl, 2-methylthiazolyl, 2-methyloxazolyl, phenyl, naphthyl, biphenyl, terphenyl, double spiro, tetracenyl, 3-methyl-phenyl, 4-methyl-naphthyl, 4 methyl-tetracenyl, 2-methyl-imidazolyl, 2-methyl-oxazolyl, 2-methyl-thiazolyl, 2-methyl-furanyl, 2-methyl-thiophenyl, 2-methyl-pyrazolyl, 2-methyl-pyridyl, 2-methyl-pyrimidinyl, methoxy, ethoxy, propoxy, butoxy, pentoxy, hexoxy, isopropoxy, isobutoxy, t-butoxy, neo-pentoxy, phenoxy, napththoxy, biphenoxy, 3-methyl-phenoxy, 4-methyl-napththoxy, 2-methyl-biphenoxy, methylamine, ethylamine, propylamine, butylamine, pentylamine, hexylamine, heptylamine, isopropylamine, isobutylamine, t-butylamine, 2-pentylamine, neo-pentylamine, phenylamine, naphthylamine, biphenylamine, anthracenylamine, 3-methyl-phenylamine, 4-methyl-naphthylamine, 2-methyl-biphenylamine, 9-methyl-anthracenylamine, phenyl methylamine, phenyl ethylamine, naphthylmethylamine, naphthylethylamine, biphenyl methylamine, 3-methyl-phenyl methylamine, phenyl isopropylamine, naphthylisopropylamine, naphthylisobutylamine, biphenyl isopropylamine, trimethylsilyl, triethylsilyl, tributylsilyl, tri(isopropyl)silyl, tri(isobutyl)silyl, tri(t-butyl)silyl, tri(2-butyl)silyl, triphenyl silyl, trinaphthylsilyl, tribiphenyl silyl, tri(3-methylphenyl)silyl, tri(4-methylnaphthyl)silyl, tri(2-methylbiphenyl)silyl, phenyl methylsilyl, phenyl ethylsilyl, naphthylmethylsilyl, naphthylethylsilyl, biphenyl methylsilyl, 3-methyl-phenyl methylsilyl, phenyl isopropylsilyl, naphthylisopropylsilyl, naphthylisobutylsilyl, biphenyl isopropylsilyl, dimethylboranyl, diethylboranyl, dipropylamine, dibutylamine, dipentylamine, diisopropylboranyl, diisobutylboranyl, di(t-butyl)boranyl, isopropylisobutylamine, diphenylboranyl, dinaphthylboranyl, dibiphenylboranyl, di(3-methylphenyl)boranyl, di(4-methylnaphthyl)boranyl, di(2-methylbiphenyl)boranyl, phenyl methylboranyl, phenyl ethylboranyl, naphthylmethylboranyl, naphthylethylboranyl, biphenyl methylboranyl, 3-methyl-phenyl methylboranyl, phenyl isopropylboranyl, methylthio, ethylthio, propylthio, butylthio, pentylthio, hexylthio, tri(isopropyl)thio, tri(isobutyl)thio, tri(t-butyl)thio, tri(2-butyl)thio, phenylthio, naphthylthio, biphenylthio, (3-methylphenyl)thio, (4-methylnaphthyl)thio and (2-methylbiphenyl)thio groups.

7. The compound according to claim 1, wherein $R_1$ to $R_6$, which are not represented by the formula 2, in the formula 1, and $R_7$ and $R_8$ in the formula 2 are each independently the identical or different substituent, and each can be selected from the group consisting of methyl, ethyl, isopropyl, t-butyl, ethenyl, propenyl, 2-methyl-ethenyl, 2-methyl-propenyl, imidazolyl, thiazolyl, oxazolyl, 2-methylimidazolyl, 2-methylthiazolyl, 2-methyloxazolyl, phenyl, naphthyl, biphenyl, terphenyl, 3-methyl-phenyl, 4-methyl-naphthyl, methoxy, ethoxy, isopropoxy, isobutoxy, phenoxy, napththoxy, 3-methyl-phenoxy, 4-methyl-napththoxy, methylamine, ethylamine, isopropylamine, isobutylamine, t-butylamine, phenylamine, naphthylamine, 3-methyl-phenylamine, 4-methyl-naphthylamine, phenyl methylamine, phenyl ethylamine, naphthylmethylamine, 3-methyl-phenyl methylamine, phenyl isopropylamine, trimethylsilyl, triethylsilyl, tri(isopropyl)silyl, tri(isobutyl)silyl, triphenyl silyl, trinaphthylsilyl, tri(3-methylphenyl)silyl, tri(4-methylnaphthyl)silyl, phenyl methylsilyl, phenyl ethylsilyl, 3-methyl-phenyl methylsilyl, phenyl isopropylsilyl, dimethylboranyl, diethylboranyl, diisopropylboranyl, diisobutylboranyl, diphenylboranyl, dinaphthylboranyl, di(3-methylphenyl)boranyl, di(4-methylnaphthyl)boranyl, phenyl methylboranyl, phenyl ethylboranyl, 3-methyl-phenyl methylboranyl, phenyl isopropylboranyl, methylthio, ethylthio, tri(isopropyl)thio, tri(isobutyl)thio, phenylthio, naphthylthio, (3-methylphenyl)thio and (4-methylnaphthyl)thio groups.

8. The compound according to claim 1, wherein $R_1$ to $R_6$, which are not represented by the formula 2, in the formula 1, and $R_7$ and $R_8$ in the formula 2 are each independently the identical or different substituent, and each can be selected from the group consisting of substituted or unsubstituted phenyl, substituted or unsubstituted naphthyl, substituted or unsubstituted biphenyl, and substituted or unsubstituted terphenyl.

9. The compound according to claim 8, wherein the substituted phenyl, naphthyl, biphenyl, and terphenyl are substituted with at least one selected from the group consisting of cyano, nitro, formyl, substituted or unsubstituted $C_1$-$C_{20}$ alkyl, aryl, heteroaryl, $C_4$-$C_7$ cycloalkenyl, substituted or unsubstituted $C_1$-$C_{20}$ alkoxy, aryloxy, $C_1$-$C_{20}$ alkylamine, arylamine, alkylarylamine, $C_1$-$C_{20}$ silyl, arylsilyl, alkylarylsilyl, $C_1$-$C_{20}$ alkylboranyl, arylboranyl, alkylarylboranyl, $C_1$-$C_{20}$ alkylthio and arylthio groups.

10. The compound according to claim 1, wherein at least one of R2 and R5 in the formula 1 is a group represented by the formula 2.

11. The compound according to claim 10, wherein R2 and R5 in the formula 1 are the same substituents represented by the formula 2.

12. The compound according to claim 10, wherein R2 and R5 in the formula 1 are the different substituents represented by the formula 2, and one of R2 and R5 is a substituent represented by the formula 2 with L1 being a direct bond, phenyl, naphthyl or carbazole.

13. The compound according to claim 1, wherein at least one of R1, R3, R4 and R6 in the formula 1 is a group represented by the formula 2.

14. The compound according to claim 13, wherein in the formula 1, one of R1 and R6 and one of R3 and R4 are the same substituents represented by the formula 2.

15. The compound according to claim 13, wherein in the formula 1, one of R1 and R6 and one of R3 and R4 are the different substituents represented by the formula 2, and one among them is a substituent represented by the formula 2 with $L_1$ being a direct bond, phenyl, naphthyl or carbazole.

16. The compound according to claim 1, wherein at least one of $R_1$ to $R_6$ is represented by the formula 2, and the remaining $R_1$ to $R_6$ can be selected from the group consisting of:

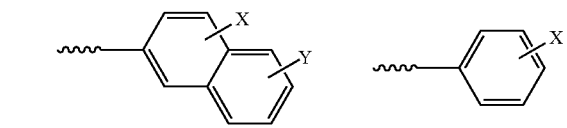

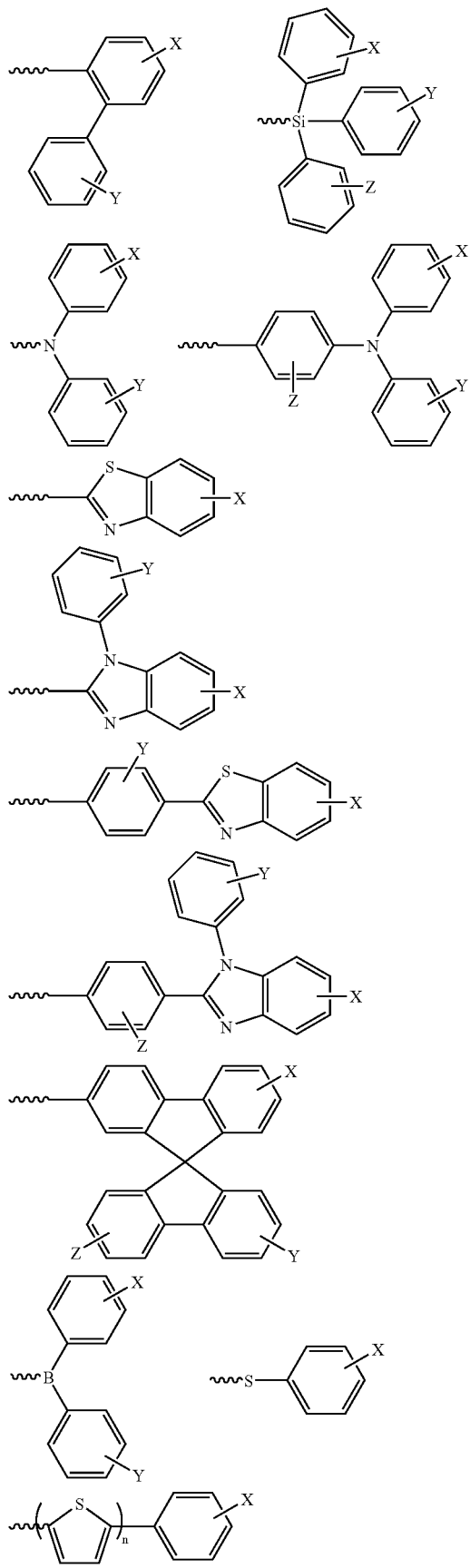
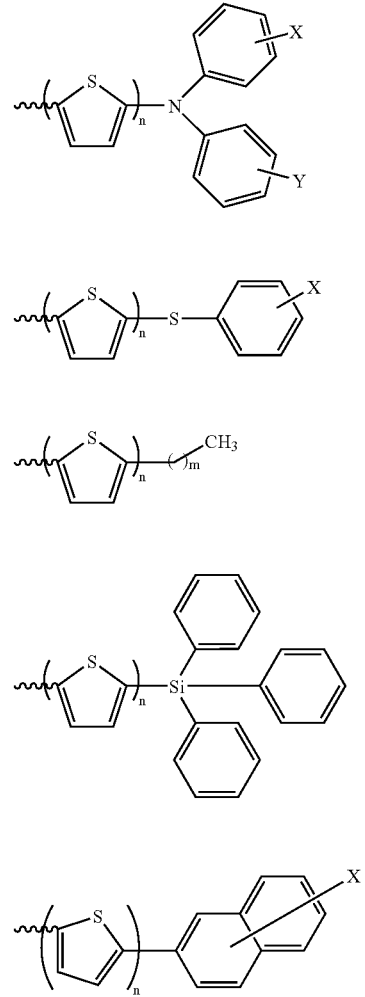

wherein X, Y and Z are each independently the identical or different substituents and each ring moiety to which X, Y or Z can be attached can be substituted with one or more of the identical or different substituents, such as X, Y and Z, and X, Y and Z are each independently selected from the group consisting of cyano, nitro, formyl, substituted or unsubstituted $C_1$-$C_{20}$ alkyl, aryl, heteroaryl, $C_4$-$C_7$ cycloalkenyl, substituted or unsubstituted $C_1$-$C_{20}$ alkoxy, aryloxy, $C_1$-$C_{20}$ alkylamine, arylamine, alkylarylamine, $C_1$-$C_{20}$ silyl, arylsilyl, alkylarylsilyl, $C_1$-$C_{20}$ alkylboranyl, arylboranyl, alkylarylboranyl, $C_1$-$C_{20}$ alkylthio and arylthio.

17. The compound according to claim 16, wherein

X, Y and Z are each independently selected from the group consisting of cyano, nitro, methyl, ethyl, isopropyl, t-butyl, methoxy, ethoxy, propoxy, methylthio, imidazolyl, pyridyl, thiazolyl, oxazolyl, furanyl, thiophenyl, pyrrolyl, pyridyl and pyrimidyl.

18. The compound according to claim 1, wherein in the formula 2, $L_1$ is a direct bond, or phenyl, naphthyl or carbazole, and $L_2$ is phenyl, naphthyl or anthracenyl.

19. The compound according to claim 1, wherein the compound is selected from the group consisting of:

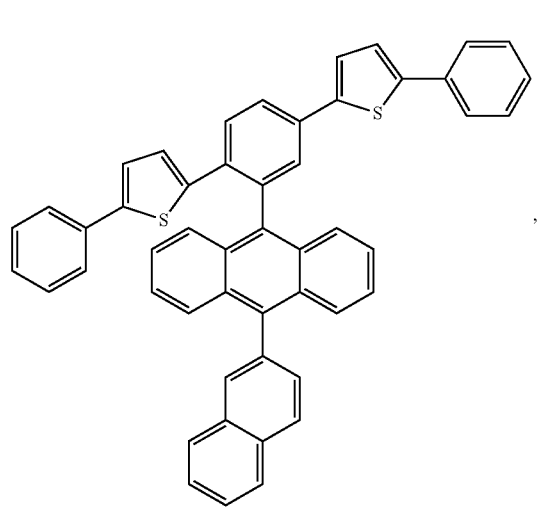
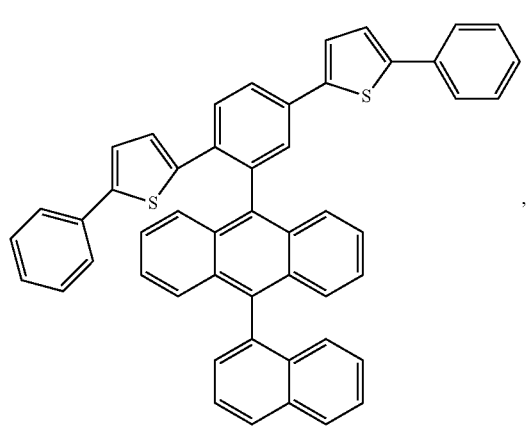
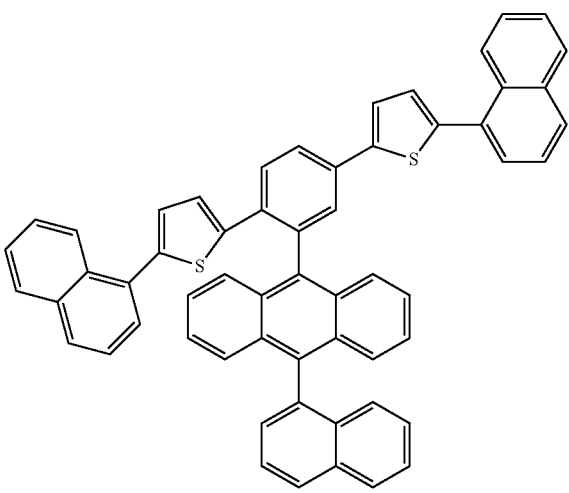

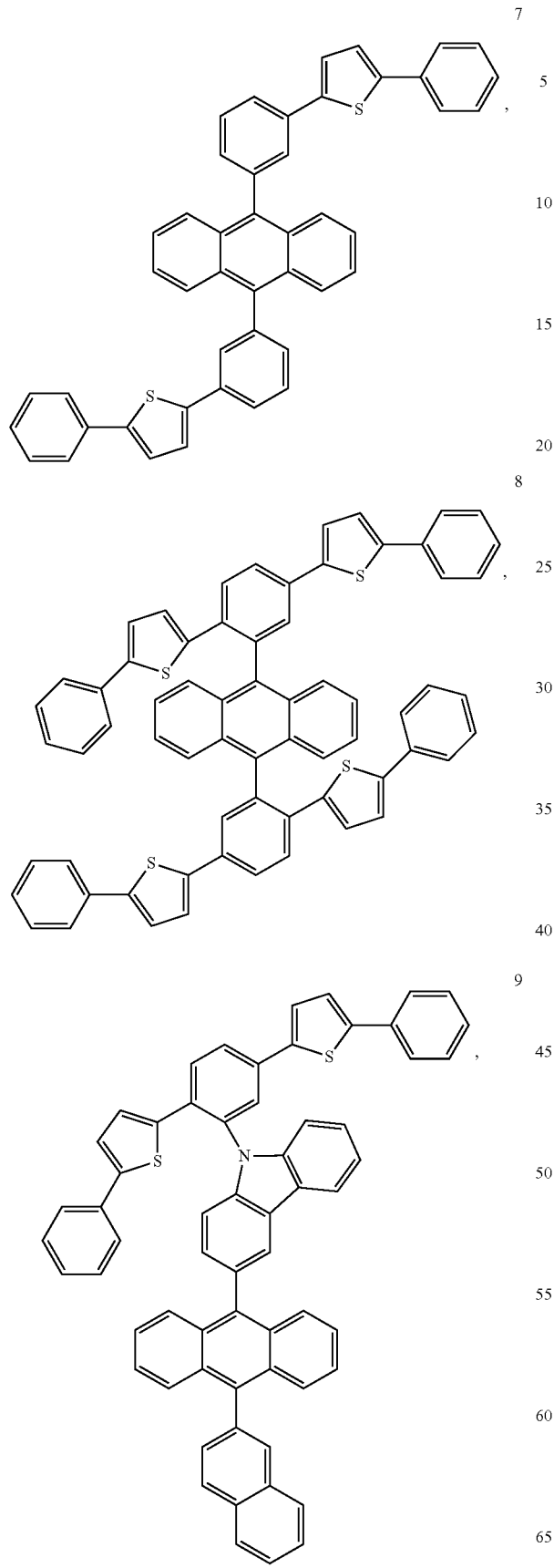
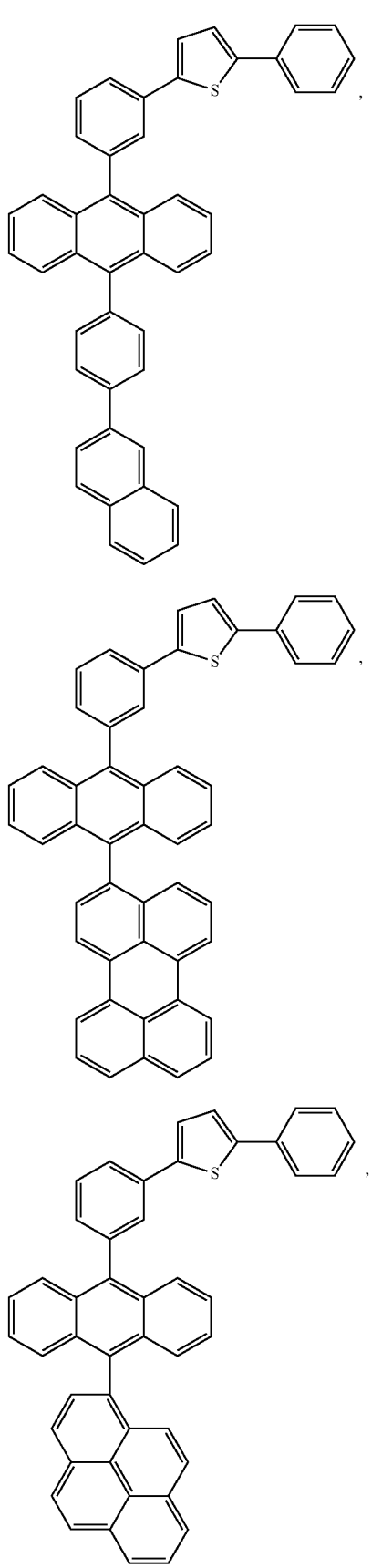

-continued
13
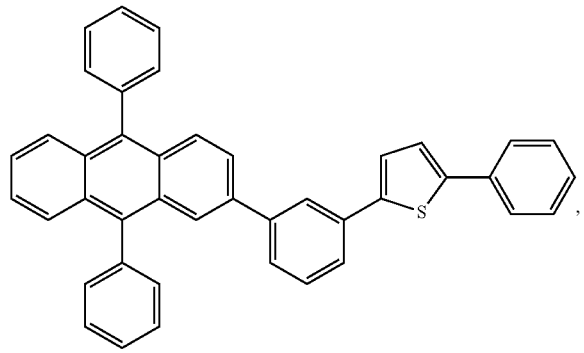
14
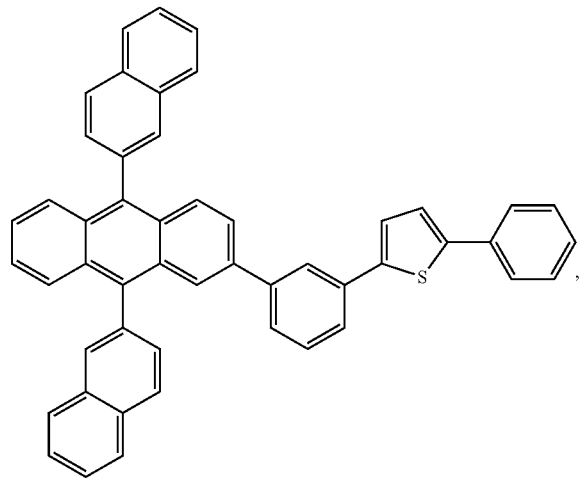
15
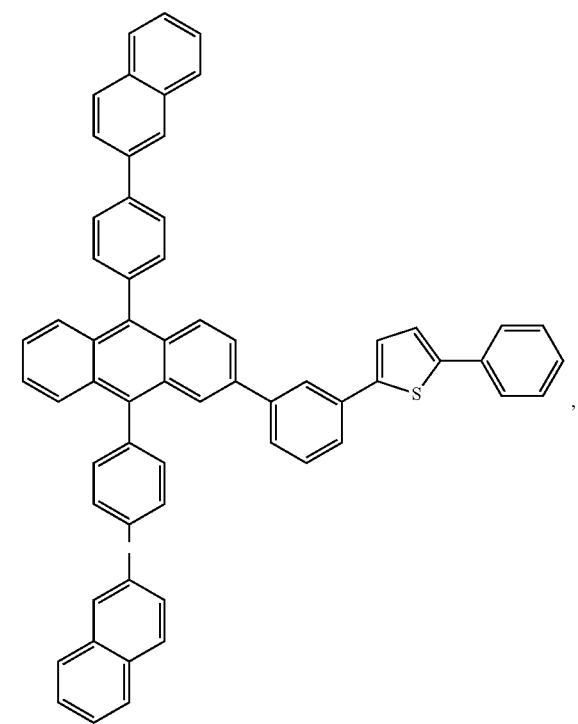
-continued
16
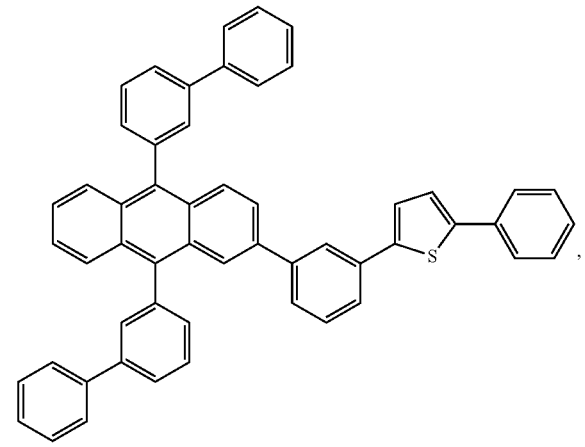
17
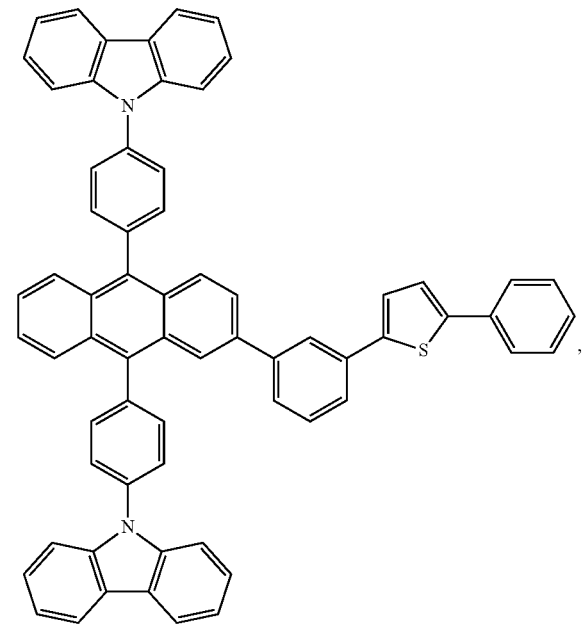
18
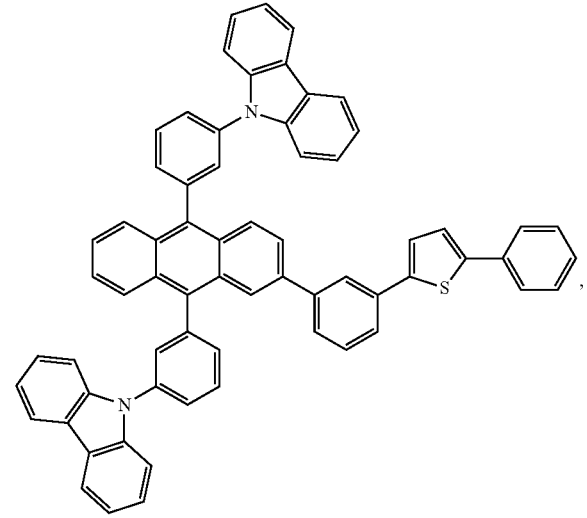

19
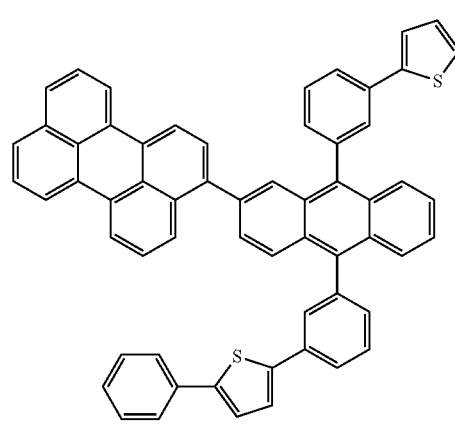
20
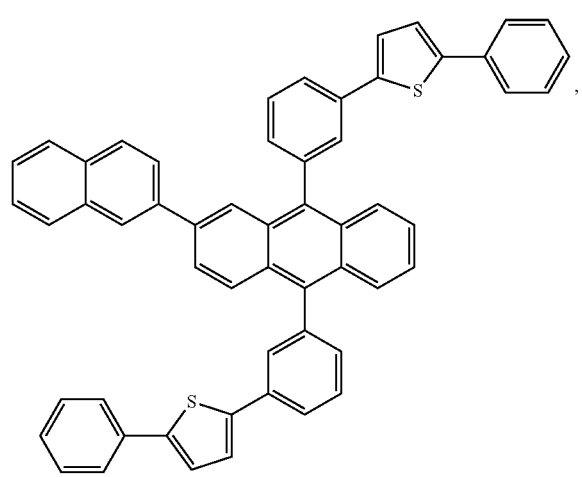
21
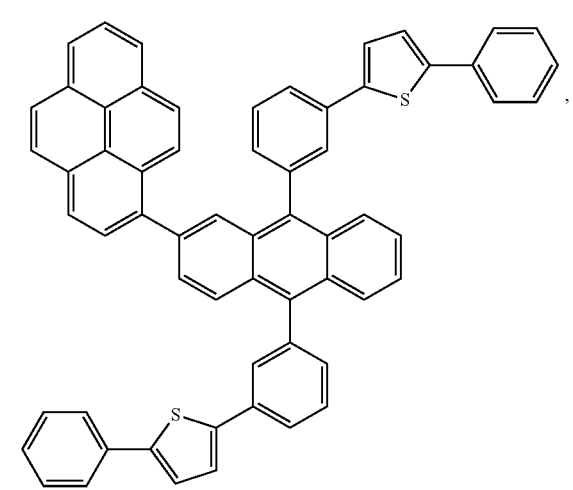
22
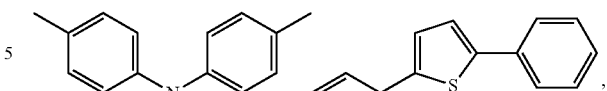
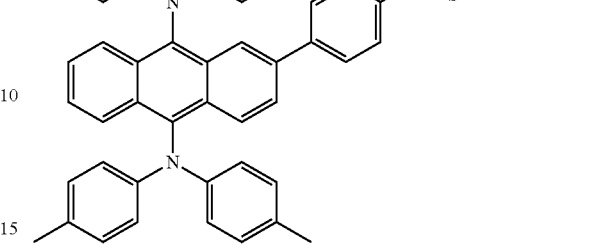
23
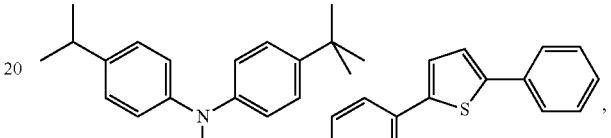
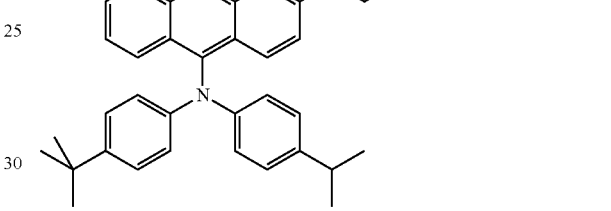
24
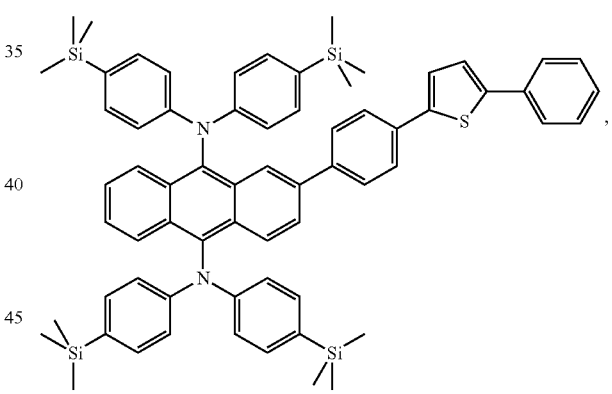
25
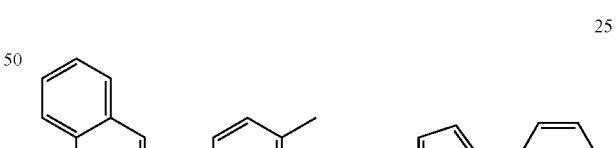
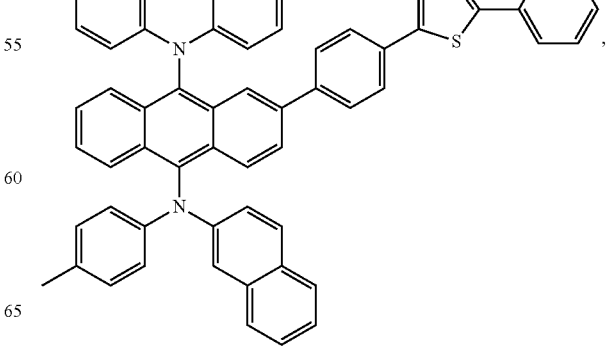

26
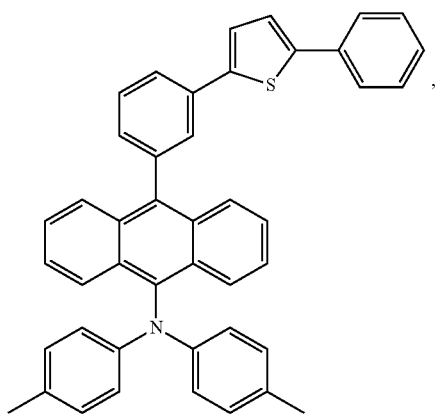
27
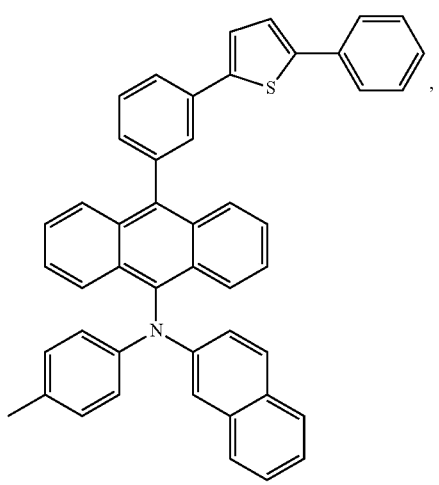
28
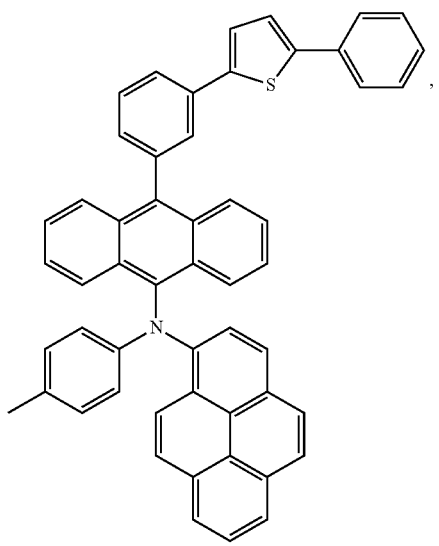
29
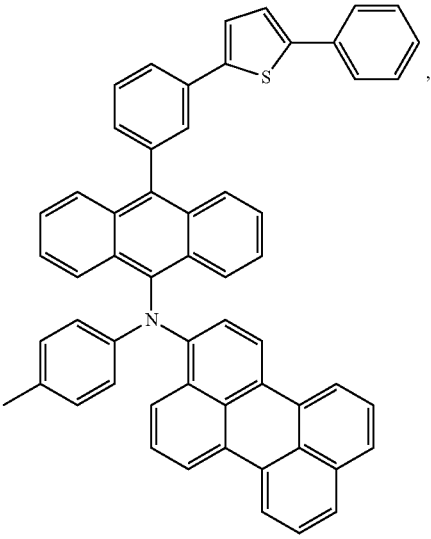
30
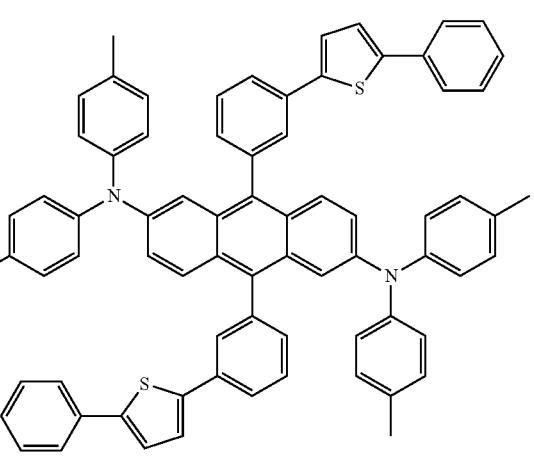
31
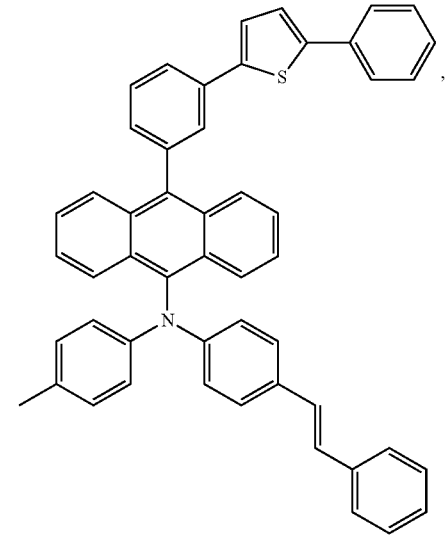

131
-continued
32
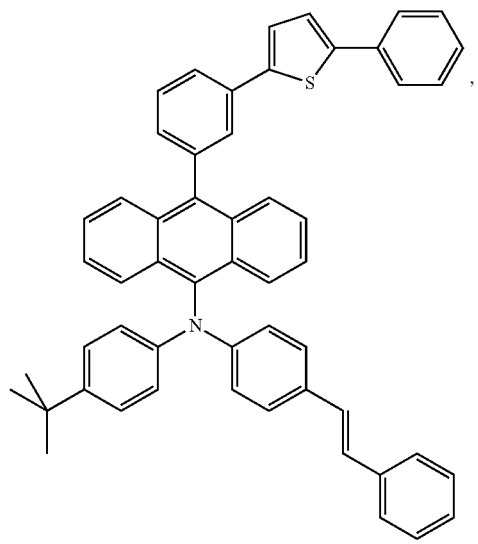
33
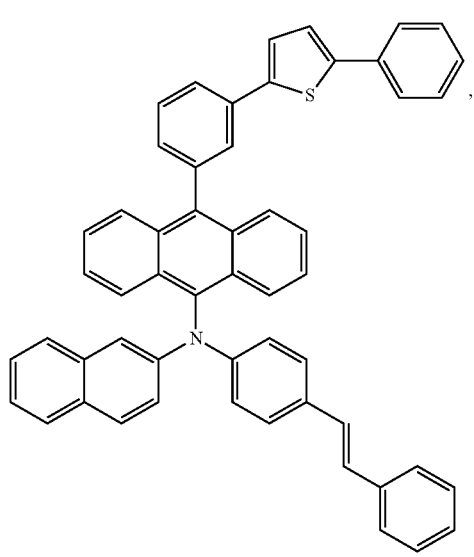
34
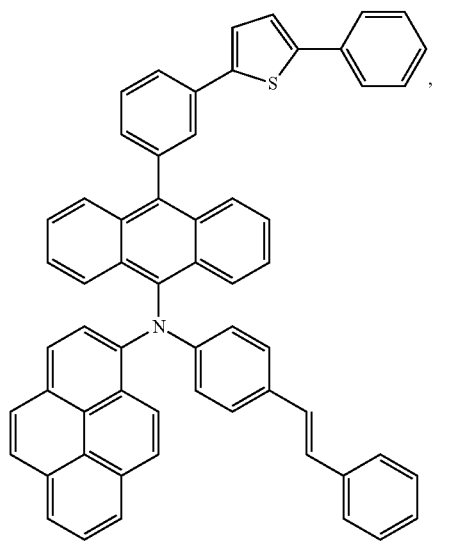
132
-continued
35
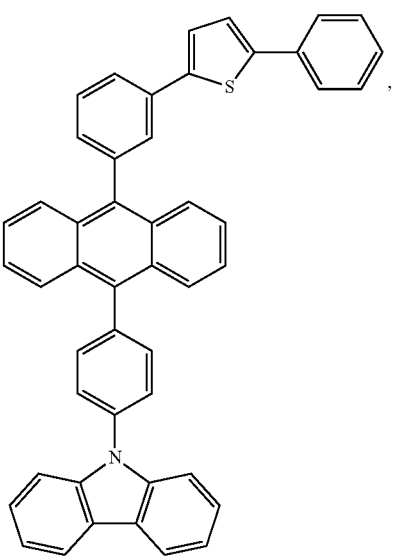
36
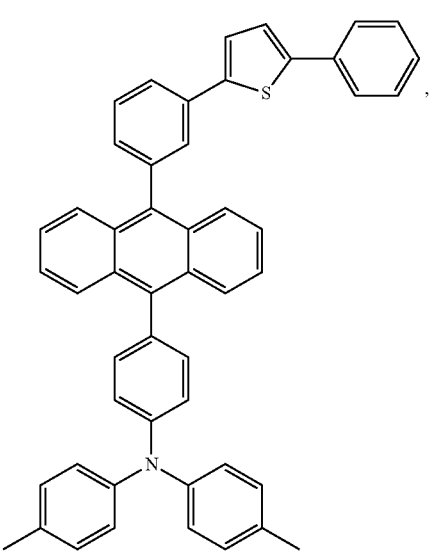
37
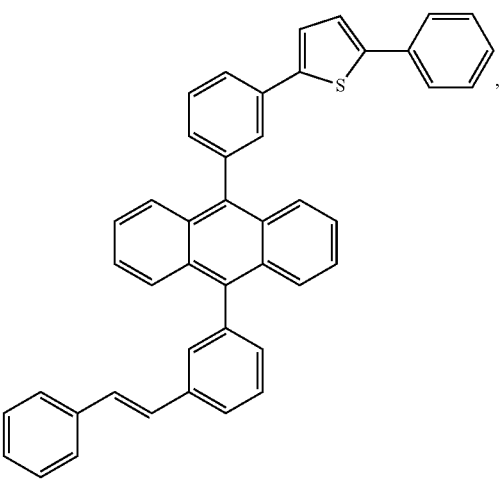

133
38
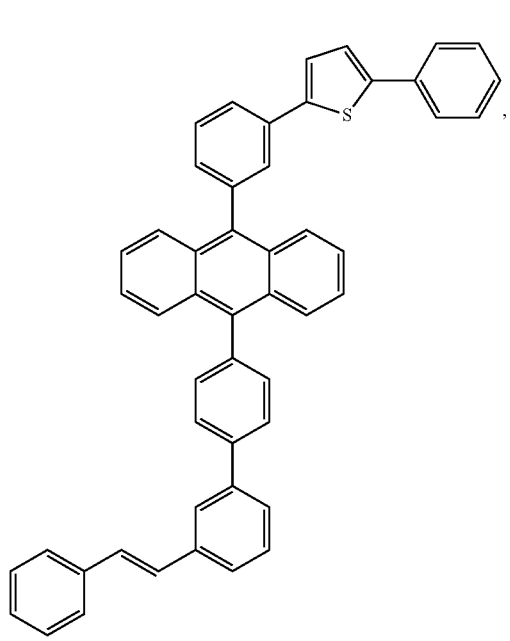
39
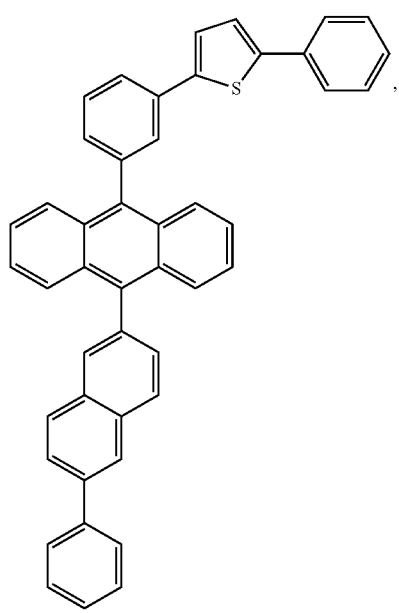
134
40
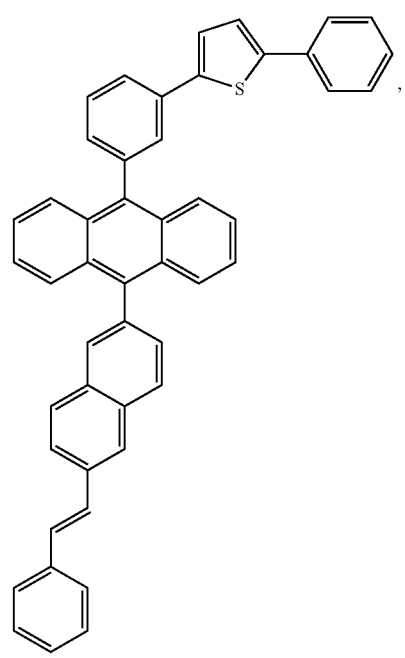
41
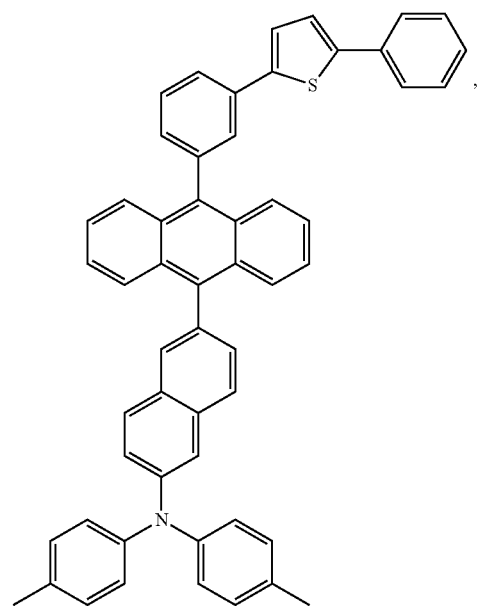

42
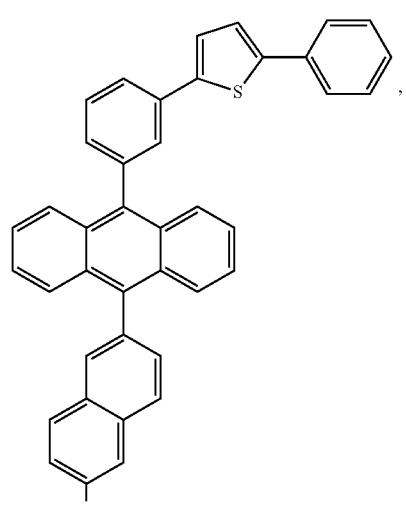
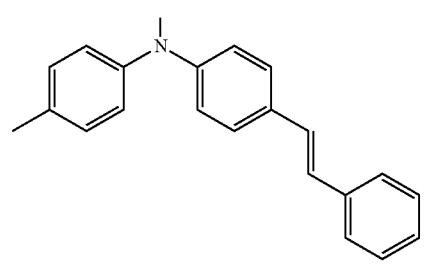
44
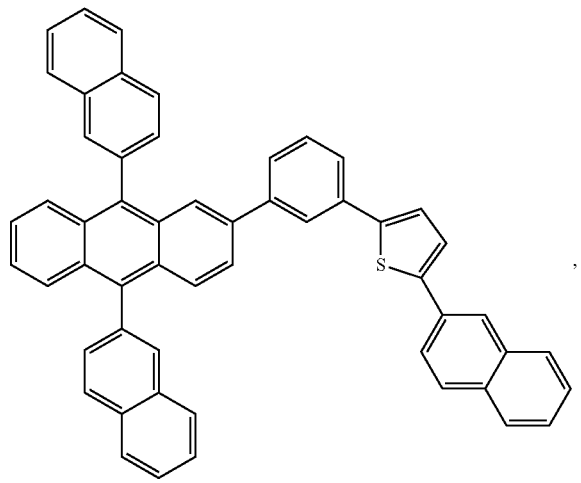
45
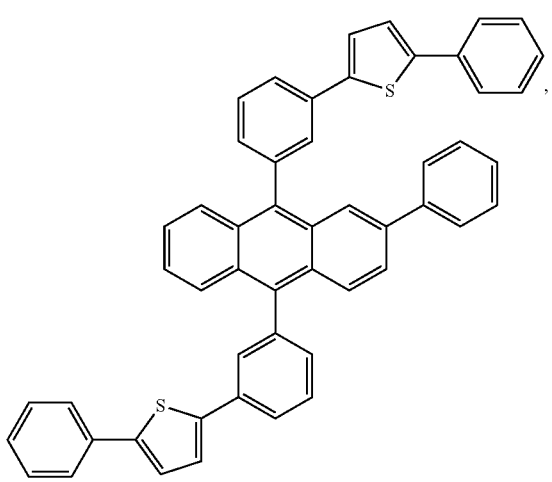
43
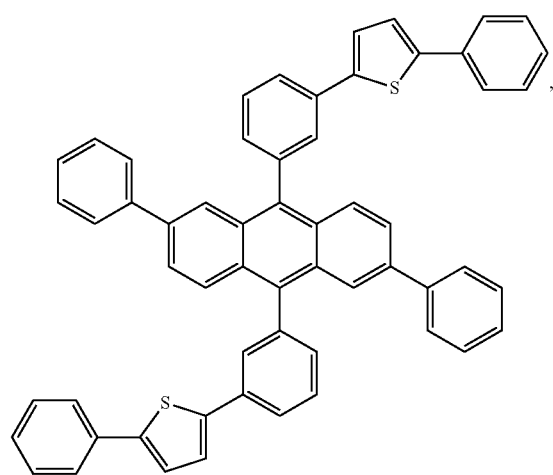
46

-continued
47
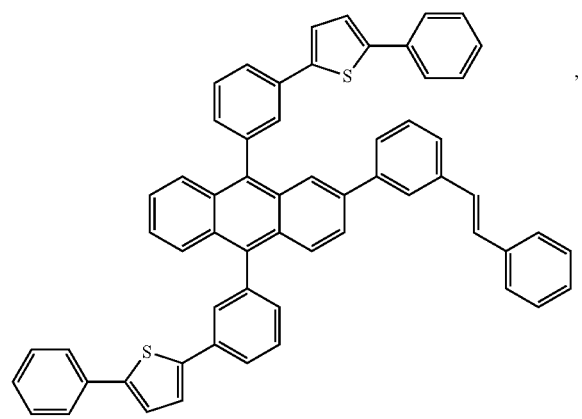
48
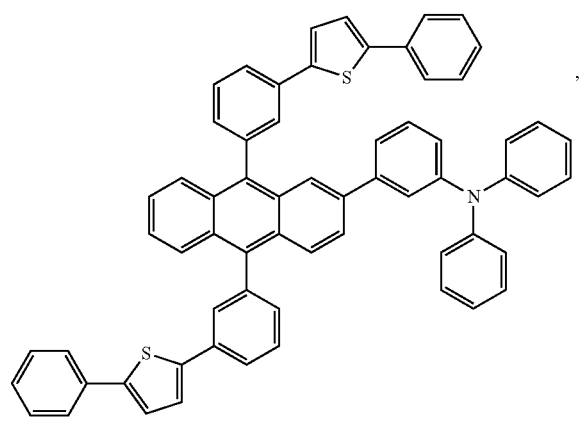
49
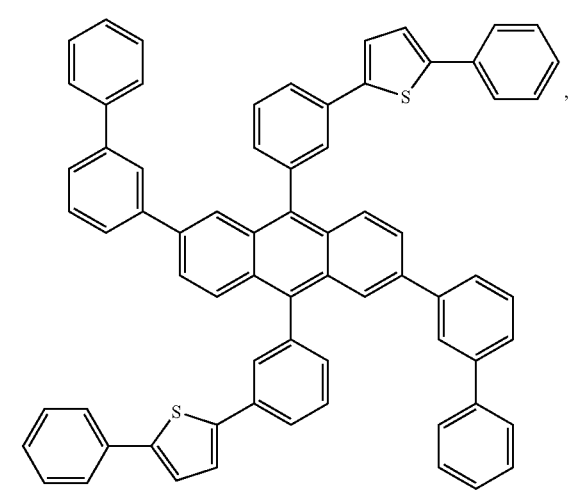
-continued
50
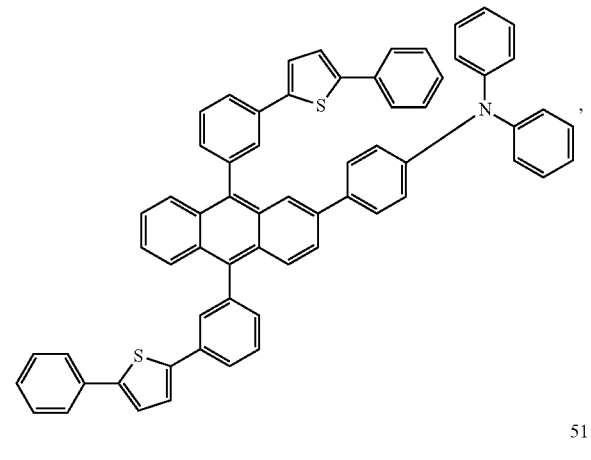
51
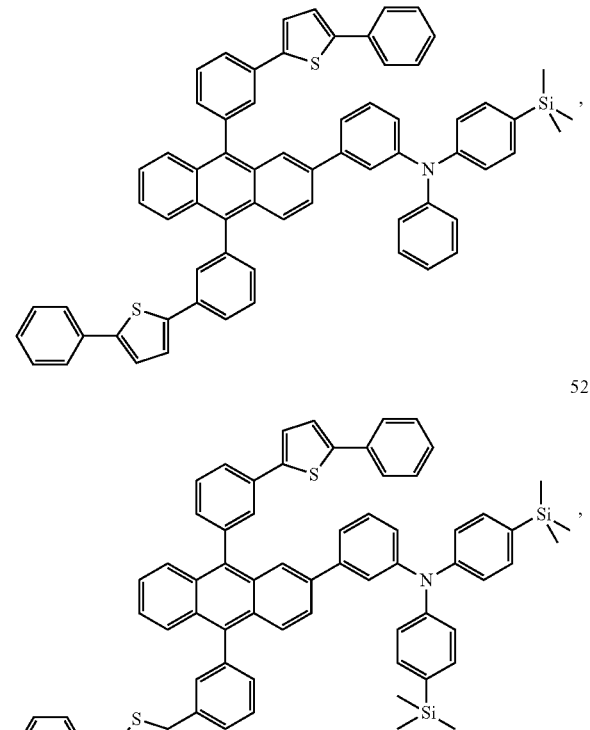
52
53
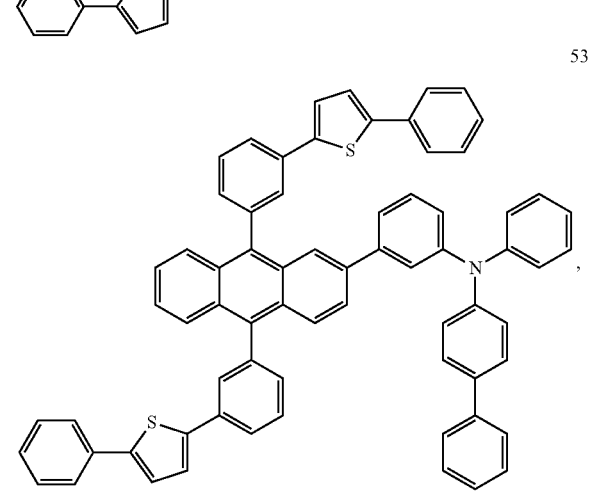

54
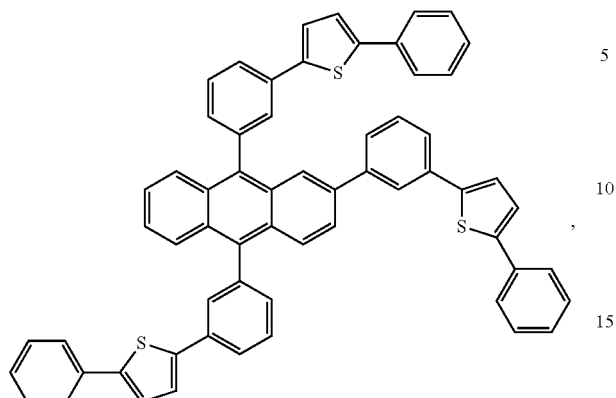
55
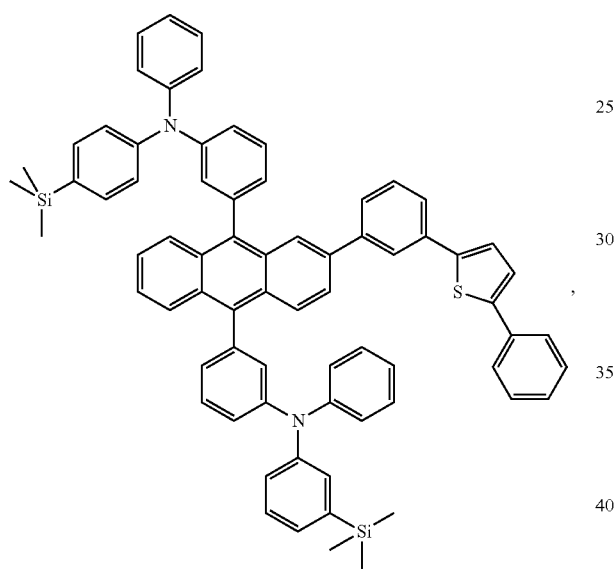
56
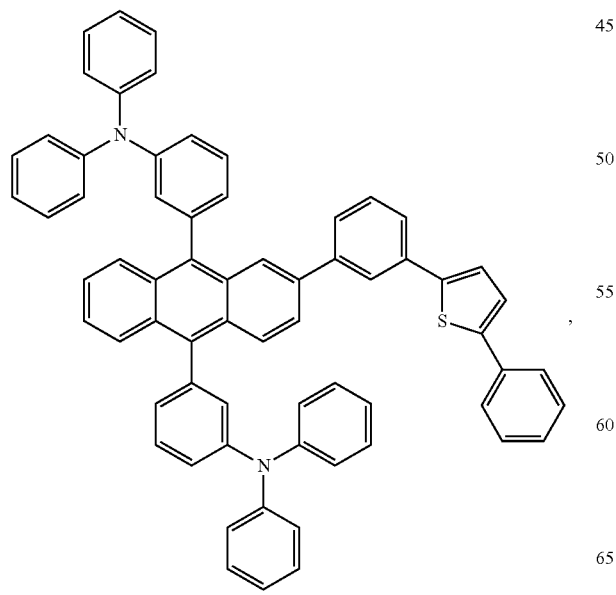
57
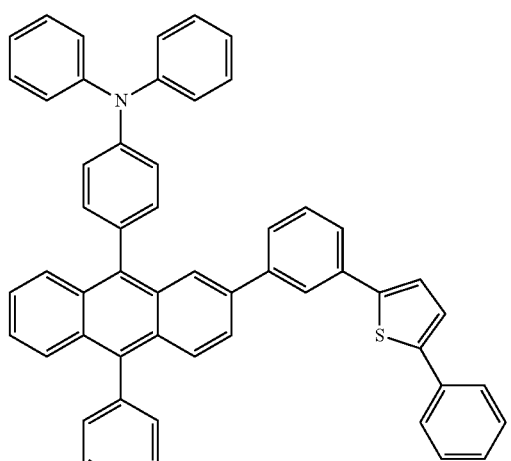
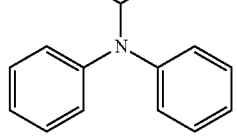
58
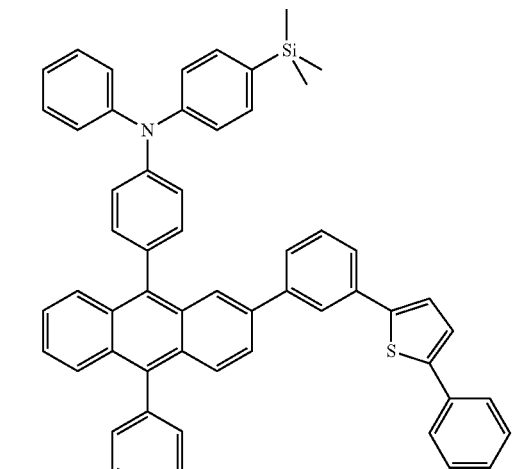
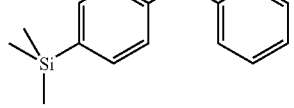

141
-continued
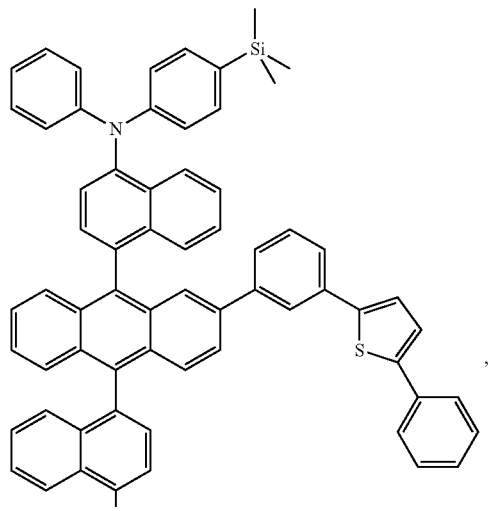
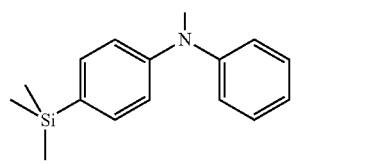
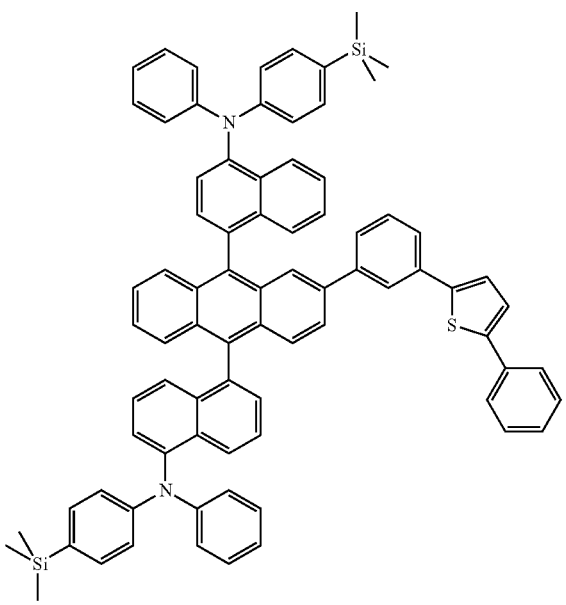
142
-continued
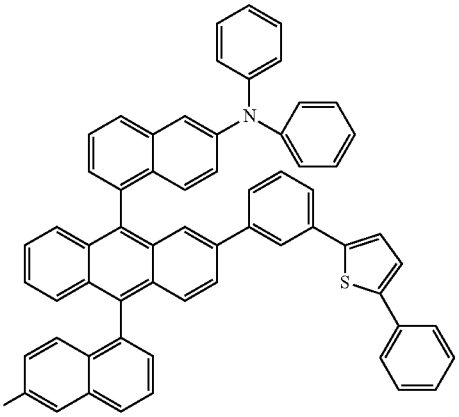
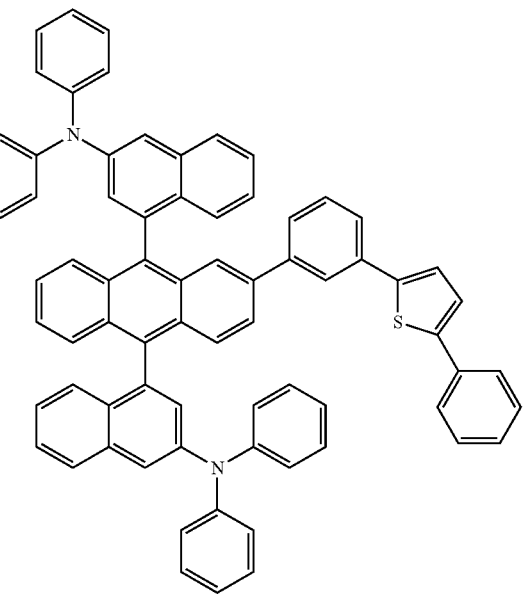

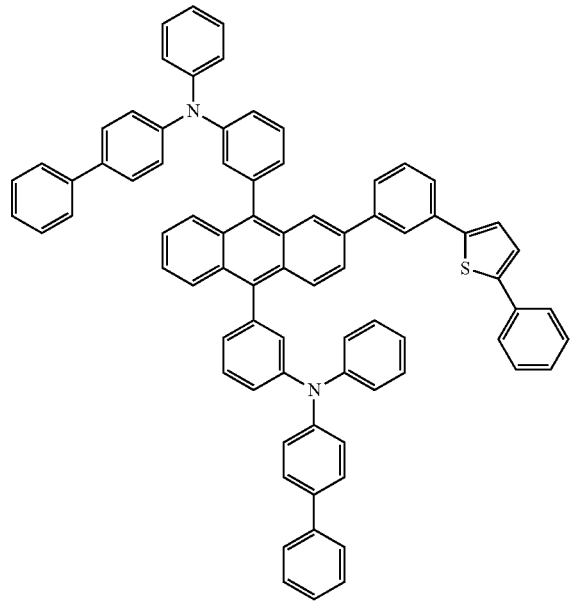
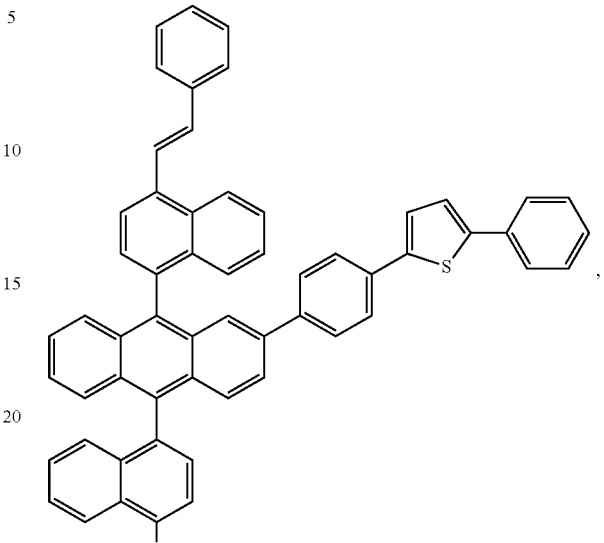
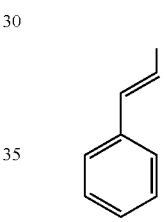
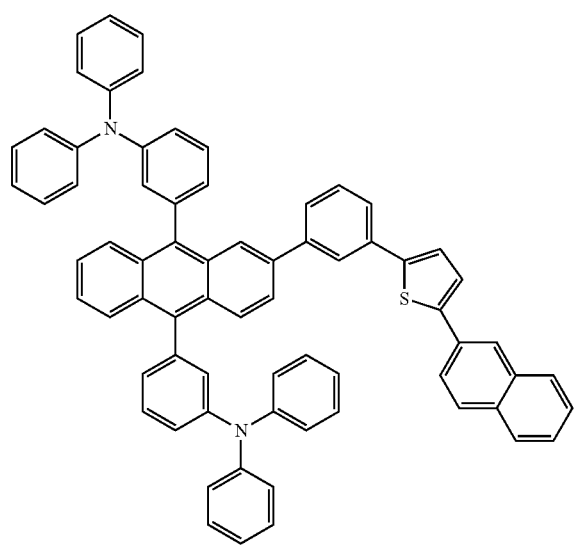
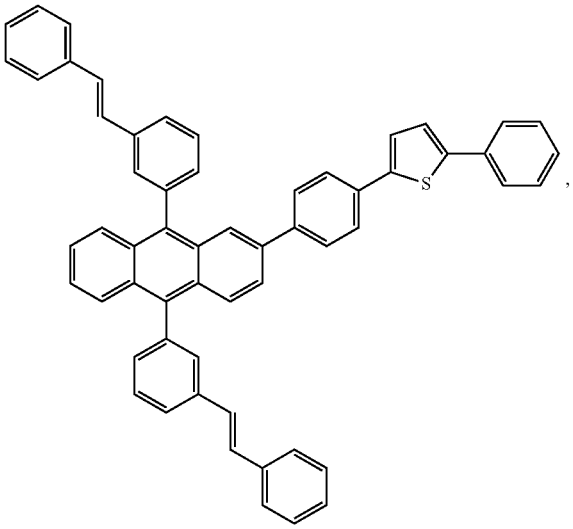

20. An organic light emitting device comprising a first electrode, a second electrode, and at least one organic material layer interposed between the first electrode and the second electrode, wherein at least one layer of the organic material layers Comprises the compound represented by formula 1 according to claim 1.

21. The organic light emitting device according to claim 20, wherein the organic material layers include a light emitting layer comprising the compound represented by formula 1.

22. The organic light emitting device according to claim 20, wherein the organic material layers include at least one selected from the group consisting of a hole injecting layer, a hole transporting layer, and an electron transporting layer.

* * * * *